(12) United States Patent
Yashiro et al.

(10) Patent No.: US 8,593,715 B2
(45) Date of Patent: Nov. 26, 2013

(54) ELECTROCHROMIC COMPOUND, ELECTROCHROMIC COMPOSITION, AND DISPLAY ELEMENT

(75) Inventors: Tohru Yashiro, Kanagawa (JP); Shigenobu Hirano, Kanagawa (JP); Yousuke Manabe, Kyoto (JP); Satoshi Hayashi, Kyoto (JP)

(73) Assignee: Ricoh Company, Ltd., Tokyo (JP)

( * ) Notice: Subject to any disclaimer, the term of this patent is extended or adjusted under 35 U.S.C. 154(b) by 40 days.

(21) Appl. No.: 13/501,007

(22) PCT Filed: Oct. 8, 2010

(86) PCT No.: PCT/JP2010/068220
§ 371 (c)(1),
(2), (4) Date: Apr. 9, 2012

(87) PCT Pub. No.: WO2011/046222
PCT Pub. Date: Apr. 21, 2011

(65) Prior Publication Data
US 2012/0194894 A1 Aug. 2, 2012

(30) Foreign Application Priority Data

| Oct. 16, 2009 | (JP) | 2009-238879 |
| Oct. 16, 2009 | (JP) | 2009-238880 |
| Oct. 16, 2009 | (JP) | 2009-239891 |
| Oct. 16, 2009 | (JP) | 2009-239892 |
| Jul. 30, 2010 | (JP) | 2010-172094 |
| Jul. 30, 2010 | (JP) | 2010-172866 |
| Jul. 30, 2010 | (JP) | 2010-172867 |

(51) Int. Cl.
*G02F 1/153* (2006.01)

(52) U.S. Cl.
USPC ........................................... 359/273

(58) Field of Classification Search
USPC .................................. 359/270, 273
See application file for complete search history.

(56) References Cited

U.S. PATENT DOCUMENTS

| 4,039,255 | A | 8/1977 | Yamashita |
| 6,301,038 | B1 | 10/2001 | Fitzmaurice et al. |
| 7,006,277 | B2 | 2/2006 | Mizuno |
| 7,333,259 | B2 | 2/2008 | Hirano et al. |
| 7,489,432 | B2 | 2/2009 | Shibuya et al. |
| 7,570,412 | B2 | 8/2009 | Shibuya et al. |
| 7,663,797 | B2 | 2/2010 | Hirano et al. |
| 2001/0030794 | A1 | 10/2001 | Berneth et al. |
| 2002/0167480 | A1 | 11/2002 | Johnson et al. |
| 2009/0002802 | A1* | 1/2009 | Shibuya et al. ............... 359/273 |
| 2009/0231663 | A1 | 9/2009 | Hirano et al. |
| 2009/0231664 | A1 | 9/2009 | Shibuya et al. |
| 2012/0050838 | A1 | 3/2012 | Hirano et al. |

FOREIGN PATENT DOCUMENTS

| JP | 50-57627 | 5/1975 |
| JP | 5-70455 | 3/1993 |
| JP | 2001-510590 | 7/2001 |
| JP | 2001-235770 | 8/2001 |

(Continued)

OTHER PUBLICATIONS

International Search Report and Written Opinion in PCT/JP2010/068220.

(Continued)

*Primary Examiner* — James Jones
(74) *Attorney, Agent, or Firm* — Cooper & Dunham LLP

(57) ABSTRACT

Disclosed are electrochromic compounds represented by the formulas defined in the specification.

6 Claims, 37 Drawing Sheets

(56) References Cited

FOREIGN PATENT DOCUMENTS

| JP | 2003-121883 | 4/2003 |
|---|---|---|
| JP | 2003-161964 | 6/2003 |
| JP | 2003-270671 | 9/2003 |
| JP | 2004-151265 | 5/2004 |
| JP | 2004-520621 | 7/2004 |
| JP | 2004-361514 | 12/2004 |
| JP | 2004-536344 | 12/2004 |
| JP | 2006-106669 | 4/2006 |
| JP | 2007-121418 | 5/2007 |
| JP | 2007-171781 | 7/2007 |
| JP | 2007-219271 | 8/2007 |
| JP | 2007-219272 | 8/2007 |
| JP | 2007-241238 | 9/2007 |
| JP | 2007-279570 | 10/2007 |
| JP | 2007-279571 | 10/2007 |
| JP | 2008-116665 | 5/2008 |
| JP | 2008-116716 | 5/2008 |
| JP | 2008-116718 | 5/2008 |
| JP | 2008-122578 | 5/2008 |
| JP | 2008-179725 | 8/2008 |
| JP | 2009-48142 | 3/2009 |
| JP | 2010-33016 | 2/2010 |
| WO | WO03/009059 A1 | 1/2003 |

OTHER PUBLICATIONS

European Search Report dated Feb. 25, 2013 in connection with counterpart.
European patent application No. 10 82 3490.7.
Takahashi et al., "Synthesis and Characterization of New Conjugation-extended Viologens Involving a Central Aromatic Linking Group", J. Chem. Soc., 1992.

\* cited by examiner

ELECTROCHROMIC COMPOUND, ELECTROCHROMIC COMPOSITION, AND DISPLAY ELEMENT

TECHNICAL FIELD

The present invention relates to an electrochromic compound, an electrochromic composition, a display element, and a display device.

The present invention relates to an electrochromic compound and electrochromic composition providing yellow, cyan, or black color development at the time of its color development and a display element using the electrochromic compound or electrochromic composition.

The present invention relates to an electrochromic compound and electrochromic composition providing magenta color development at the time of its color development and a display element using the electrochromic compound or electrochromic composition.

BACKGROUND ART

An electronic paper is known as an electronic medium replacing a paper, and recently, an electronic paper has been developed actively.

Because an electronic paper is characterized in that a display device is used like a paper, a characteristic is required which is different from that of a conventional apparatus such as a CRT (Cathode Ray Tube) or a liquid crystal display. For example, a characteristic is required such that it is a reflection-type display device, has a high white reflectance or high contrast ratio, is capable of providing a highly fine display, providing a display with a memory effect, is capable of operating at a low voltage, is thin and light, and is inexpensive. Among these, in particular, there is a high need for a white reflectance or contrast ratio comparable to that of a paper, and further a color display, as a characteristic associated with a display quality.

Until now, for example, a reflection-type liquid crystal display device using a reflection-type liquid crystal, an electrophoretic display device using electrophoresis, a device using a toner migration, and the like are proposed and known as display devices for an electronic paper application. However, it may be very difficult for any of the above-mentioned devices to conduct multicolor display while a white reflectance and a contrast ratio are retained. Generally, a color filter is provided to conduct multicolor display, but when a color filter is provided, such a color filter absorbs light to degrade its reflectance. In addition, a color filter divides one picture element into three parts, for example, red (R), green (G), and blue (B), whereby a white reflectance of a display device is degraded and accordingly, a contrast ratio thereof is degraded. When a white reflectance and a contrast ratio are considerably degraded, a visibility may be deteriorated significantly and its use as an electronic paper may be difficult.

Japanese Patent Application Publication No. 2003-161964 and Japanese Patent Application Publication No. 2004-361514 disclose reflection-type color display media in which a color filter is formed on an electrophoretic element, but it is clear that no good image quality may be obtained when a color filter is formed on a display medium with a low white reflectance and a low contrast ratio.

Furthermore, Japanese Patent Application Publication No. 2004-520621 and Japanese Patent Application Publication No. 2004-536344 disclose electrophoretic elements in which each of particles colored with plural colors is moved to attain coloring, but, even though these methods are used, the above-mentioned problem of a reflectance or contrast ratio may not be solved in principle, and it may not be possible to attain a high white reflectance and a high contrast ratio simultaneously.

Meanwhile, an electrochromic display device is known as a reflection-type display device provided with no color filter. Herein, a device using an electrochromic phenomenon is a promising technique for realizing a reflection-type display device without providing a color filter as mentioned above. An electrochromic display device is expected as a multicolor display device, because it may be possible to develop a wide variety of colors depending on a structure of an electrochromic compound.

A phenomenon such that an oxidation-reduction reaction is caused reversibly by application of an electric voltage whereby a color is changed reversibly is referred to as electrochromism. An electrochromic display device is a display device utilizing color development/color erasing (color development/erasing, below) of an electrochromic compound which causes such an electrochromism phenomenon. Study and development of such an electrochromic display device, such as material development and device designing, have been conducted widely for a potential candidate of a display device technique for an electronic paper application, because it is a reflection-type display device, has a memory effect, and is capable of operating at a low voltage.

However, an electrochromic display device may have a drawback of a slow response speed for color development/erasing due to color development/erasing conducted by utilizing an oxidation reduction reaction in principle. Japanese Patent Application Publication No. 2001-510590 discloses an example contemplated to improve a response speed of color development/erasing by fixing an electrochromic compound near an electrode. As the disclosure of Japanese Patent Application Publication No. 2001-510590 is referred to, a period of time required for color development/erasing, which was about 10 seconds conventionally, is improved so that both a period of time of color development from colorless to a blue color and a period of time of color erasing from a blue color to colorless are about 1 second. However, this may not be sufficient and further improvement of a response speed of color development/erasing is required in study and development of an electrochromic display device.

An electrochromic display device may be capable of developing a wide variety of colors depending on the structure of an electrochromic compound, and hence, expected as a multicolor display device. In particular, a colorless state and a color development state are exchanged reversibly, and hence, a laminated layer multicolor structure may be attained. In a color display with such a laminated layer structure, it is not necessary to divide one picture element into three, i.e., red (R), green (G), and blue (B) as a conventional technique, and accordingly, a reflectance and contrast ratio of a display device are not degraded.

Some examples of a multicolor display device are publicly known which utilizes such an electrochromic display device. For example, Japanese Patent Application Publication No. 2003-121883 discloses a multicolor display device using an electrochromic compound in which fine particles of plural kinds of electrochromic compounds are stacked. Herein, Japanese Patent Application Publication No. 2003-121883 discloses an example of a multicolor display device in which plural kinds of electrochromic compounds are stacked, which are a plurality of polymer compounds having a functional group and exhibiting cooler development at a different voltage, so as to provide multicolor display electrochromic compounds.

Japanese Patent Application Publication No. 2006-106669 discloses a multicolor display element characterized by including a display electrode, an opposing electrode provided to oppose and separate from the display electrode, an electrolyte arranged between both electrodes, and a display layer formed by stacking or mixing two or more kinds of electrochromic compositions developing different colors on a surface of the display electrode at an opposing electrode side, wherein at least either of threshold voltages for providing a color development state, threshold voltages for providing a color erasing state, amounts of electric charge required to develop a color with a sufficient color density, or amounts of electric charge required to erase a color sufficiently are different therefrom.

However, a viologen compound included in an electrochromic composition develops a color such as a blue color or a green color, and it may not be possible to develop a color of cyan required for attainment of full color.

Furthermore, Japanese Patent Application Publication No. 2006-106669 discloses a display device in which a multilayer of electrochromic layers are formed on an electrode and multicolor is color-developed by utilizing a difference between electric voltage values or electric current values required for color development. Herein, Japanese Patent Application Publication No. 2006-106669 discloses an example of a multicolor display device having a display layer formed by stacking or mixing plural kinds of electrochromic compounds developing different colors and having different threshold voltages for color development and amounts of electric charge required for color development.

Moreover, Japanese Patent Application No. 2003-270671 discloses an example of a multicolor display device provided by laminating a plurality of structural units in which an electrochromic layer and an electrolyte are interposed between a pair of transparent electrodes. Furthermore, Japanese Patent Application Publication No. 2004-151265 discloses an example of a multicolor display device corresponding to three colors of RGB in which a passive matrix panel and an active matrix panel are formed by a structural unit described in Japanese Patent Application No. 2003-270671.

However, viologen-based organic electrochromic compounds illustrated in Japanese Patent Application Publication No. 2001-510590, Japanese Patent Application Publication No. 2003-121883, and Japanese Patent Application Publication No. 2006-106669 develop a blue color or a green color and may not develop three primary colors of yellow, magenta, and cyan required for attainment of a full color. In order to the above-mentioned three primary colors, it may be necessary to have a sharp absorption at the time of color development, in particular, it may be necessary to have a sharp absorption in a short wavelength range with respect to yellow color development but no electrochromic compound capable of developing a yellow color and capable of developing or erasing a color stably has been obtained until now.

Furthermore, it may be necessary to have a sharp absorption in a long wavelength range with respect to cyan color development and no electrochromic compound capable of developing a cyan color and capable of developing or erasing a color stably has been obtained until now.

Moreover, no electrochromic compound having absorption all over the wavelength range of visible light and developing a black color has also been obtained until now. If an electrochromic compound developing a black color is provided, it may be possible to manufacture a monochromatic display element with a high contrast.

In addition, a styryl-type coloring agent is used in Japanese Patent Application Publication No. 2003-270671, Japanese Patent Application Publication No. 2004-151265, Japanese Patent Application Publication No. 2008-122578, whereby it may be possible to develop a color in an YMC-system and there is a problem in a color development or erasing stability or repetition durability.

Meanwhile, Japanese Patent Application Publication No. 2007-241238 discloses that a structure with a furan ring, thiophene ring, selenophene ring or alkylpyrrole ring introduced into between two pyridine rings as illustrated therein develops a good magenta color. However, this structure may be yellowish colored at a color erasing state and reduction of its coloring at a color erasing state may be problematic.

DISCLOSURE OF THE INVENTION

Problems to be Solved by the Invention

The present invention aims at providing an electrochromic compound and electrochromic composition capable of providing cyan color development or color erasing and a display element and display device having the electrochromic compound and electrochromic composition, while a problem held by the above-mentioned conventional technique is taken into consideration.

The present invention aims at providing an electrochromic compound and electrochromic composition capable of providing yellow color development and color erasing, and a display element and display device having the electrochromic compound and electrochromic composition, while a problem held by the above-mentioned conventional technique is taken into consideration.

The present invention aims at providing an electrochromic compound and electrochromic composition exhibiting a sharp light absorption spectrum characteristic at the time of color development and providing one of yellow-type, cyan-type and black-type color development, and a display element using the electrochromic compound or electrochromic composition, while a problem held by the above-mentioned conventional technique is taken into consideration.

The present invention aims at providing an electrochromic compound and electrochromic composition exhibiting a sharp light absorption spectrum characteristic at the time of color development, providing magenta-type color development, and having less coloring at the time of color erasing, and a display element using the electrochromic compound or electrochromic composition, while a problem held by the above-mentioned conventional technique is taken into consideration.

Means for Solving the Problem

The inventor(s) of the present invention has/have actively and repeatedly investigated, and as a result, it is found that the above-mentioned problem may be solved by at least a particular electrochromic compound, whereby the present invention could be completed.

That is, an electrochromic compound and electrochromic composition according to the present invention for solving the above-mentioned problem and a display element using the electrochromic compound or electrochromic composition specifically include at least one of technical features as described in the following (1) to (23).

The invention as described in (1) is an electrochromic compound characterized by being represented by a general formula of

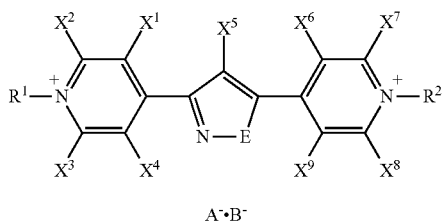

A⁻·B⁻

(in the formula, each of $X^1, X^2, X^3, X^4, X^5, X^6, X^7, X^8$, and $X^9$ is independently a hydrogen atom, a halogen group, a hydroxyl group, a nitro group, a cyano group, a carboxyl group, a substituted or non-substituted alkoxycarbonyl group, a substituted or non-substituted aryloxycarbonyl group, a substituted or non-substituted alkylcarbonyl group, a substituted or non-substituted arylcarbonyl group, an aminocarbonyl group, a substituted or non-substituted monoalkylaminocarbonyl group, a substituted or non-substituted dialkylaminocarbonyl group, a substituted or non-substituted monoarylaminocarbonyl group, a substituted or non-substituted diarylaminocarbonyl group, a sulfonate group, a substituted or non-substituted alkoxysulfonyl group, a substituted or non-substituted aryloxysulfonyl group, a substituted or non-substituted alkylsulfonyl group, a substituted or non-substituted arylsulfonyl group, an aminosulfonyl group, a substituted or non-substituted monoalkylaminosulfonyl group, a substituted or non-substituted dialkylaminosulfonyl group, a substituted or non-substituted monoarylaminosulfonyl group, a substituted or non-substituted diarylaminosulfonyl group, an amino group, a substituted or non-substituted monoalkylamino group, a substituted or non-substituted dialkylamino group, a substituted or non-substituted alkyl group, a substituted or non-substituted alkenyl group, a substituted or non-substituted alkynyl group, a substituted or non-substituted aryl group, a substituted or non-substituted alkoxy group, a substituted or non-substituted aryloxy group, a substituted or non-substituted alkylthio group, a substituted or non-substituted arylthio group, or a substituted or non-substituted heterocyclic group, each of $R^1$ and $R^2$ is independently a substituted or non-substituted alkyl group, a substituted or non-substituted alkenyl group, a substituted or non-substituted alkynyl group, or a substituted or non-substituted aryl group, E is an oxy group, a thio group, or a seleno group, each of $A^-$ and $B^-$ is independently a monovalent anion, and $R^1$ and/or $R^2$ may be substituted with one or more kinds of functional groups selected from the group composed of a sulfonate group, a phosphonate group, a phosphate group, and a carboxyl group).

The invention as described in (2) is the electrochromic compound as described in (1), characterized in that each of $R^1$ and $R^2$ is independently a substituted or non-substituted alkyl group with a carbon number of 2 or more and 20 or less or a substituted or non-substituted aryl group.

The invention as descried in (3) is an electrochromic composition characterized in that the electrochromic compound as described in (1) or (2) is bonded or adsorbed to an electrically conductive or semi-conductive nano-structure.

The invention as described in (4) is an electrochromic composition characterized by being obtained by reacting a compound represented by a general formula of

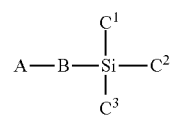

(in the formula, A is a halogen group, B is an alkylene group, $C^1$ is a halogen group or an alkoxy group, and each of $C^2$ and $C^3$ is independently a halogen group, an alkoxy group, or an alkyl group.)

with an electrically conductive or semi-conductive nano-structure and subsequently reacting a compound represented by a general formula of

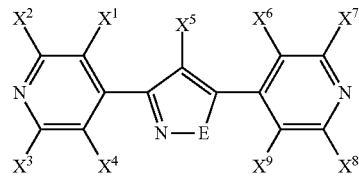

(in the formula, each of $X^1, X^2, X^3, X^4, X^5, X^6, X^7, X^8$, and $X^9$ is independently a hydrogen atom, a halogen group, a hydroxyl group, a nitro group, a cyano group, a carboxyl group, a substituted or non-substituted alkoxycarbonyl group, a substituted or non-substituted aryloxycarbonyl group, a substituted or non-substituted alkylcarbonyl group, a substituted or non-substituted arylcarbonyl group, an aminocarbonyl group, a substituted or non-substituted monoalkylaminocarbonyl group, a substituted or non-substituted dialkylaminocarbonyl group, a substituted or non-substituted monoarylaminocarbonyl group, a substituted or non-substituted diarylaminocarbonyl group, a sulfonate group, a substituted or non-substituted alkoxysulfonyl group, a substituted or non-substituted aryloxysulfonyl group, a substituted or non-substituted alkylsulfonyl group, a substituted or non-substituted arylsulfonyl group, an aminosulfonyl group, a substituted or non-substituted monoalkylaminosulfonyl group, a substituted or non-substituted dialkylaminosulfonyl group, a substituted or non-substituted monoarylaminosulfonyl group, a substituted or non-substituted diarylaminosulfonyl group, an amino group, a substituted or non-substituted monoalkylamino group, a substituted or non-substituted dialkylamino group, a substituted or non-substituted alkyl group, a substituted or non-substituted alkenyl group, a substituted or non-substituted alkynyl group, a substituted or non-substituted aryl group, a substituted or non-substituted alkoxy group, a substituted or non-substituted aryloxy group, a substituted or non-substituted alkylthio group, a substituted or non-substituted arylthio group, or a substituted or non-substituted heterocyclic group, and E is an oxy group, a thio group, or a seleno group.) therewith.

The invention as described in (5) is a display element including a display electrode, an opposing electrode provided to oppose and separate from the display electrode with a predetermined space, and an electrolyte interposed between the display electrode and the opposing electrode, characterized in that a display layer containing the electrochromic compound as described in (1) or (2) or the electrochromic composition as described in (3) or (4) is formed on a surface of the display electrode at an opposing electrode side.

The invention as described in (6) is a display device characterized by including the display element as described in (5) and a part configured to drive the display element.

The invention as described in (7) is an electrochromic compound characterized by being represented by a general formula of

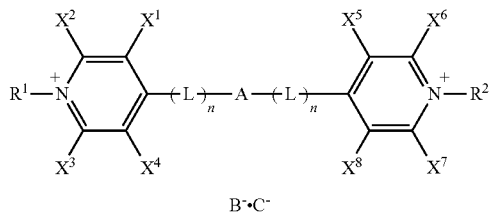

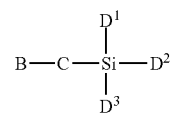

(in the formula, each of $X^1$, $X^2$, $X^3$, $X^4$, $X^5$, $X^6$, $X^7$, and $X^8$ is independently a hydrogen atom, a halogen group, a hydroxyl group, a nitro group, a cyano group, a carboxyl group, a substituted or non-substituted alkoxycarbonyl group, a substituted or non-substituted aryloxycarbonyl group, a substituted or non-substituted alkylcarbonyl group, a substituted or non-substituted arylcarbonyl group, an aminocarbonyl group, a substituted or non-substituted monoalkylaminocarbonyl group, a substituted or non-substituted dialkylaminocarbonyl group, a substituted or non-substituted monoarylaminocarbonyl group, a substituted or non-substituted diarylaminocarbonyl group, a sulfonate group, a substituted or non-substituted alkoxysulfonyl group, a substituted or non-substituted aryloxysulfonyl group, a substituted or non-substituted alkylsulfonyl group, a substituted or non-substituted arylsulfonyl group, an aminosulfonyl group, a substituted or non-substituted monoalkylaminosulfonyl group, a substituted or non-substituted dialkylaminosulfonyl group, a substituted or non-substituted monoarylaminosulfonyl group, a substituted or non-substituted diarylaminosulfonyl group, an amino group, a substituted or non-substituted monoalkylamino group, a substituted or non-substituted dialkylamino group, a substituted or non-substituted alkyl group, a substituted or non-substituted alkenyl group, a substituted or non-substituted alkynyl group, a substituted or non-substituted aryl group, a substituted or non-substituted alkoxy group, a substituted or non-substituted aryloxy group, a substituted or non-substituted alkylthio group, a substituted or non-substituted arylthio group, or a substituted or non-substituted heterocyclic group, each of $R^1$ and $R^2$ is independently a substituted or non-substituted alkyl group, a substituted or non-substituted alkenyl group, a substituted or non-substituted alkynyl group, or a substituted or non-substituted aryl group, A is a substituted or non-substituted 5-membered heterocyclic ring group containing one or more of N, O, S, or Se and containing C bonding to L, L is a substituted or non-substituted arylene group, each of $B^-$ and $C^-$ is independently a monovalent anion, n is 1, 2, or 3, and $R^1$ and/or $R^2$ may be substituted with one or more kinds of functional groups selected from the group composed of a sulfonate group, a phosphonate group, a phosphate group, and a carboxyl group).

The invention as described in (8) is the electrochromic compound as described in (7), characterized in that each of $R^1$ and $R^2$ is independently a substituted or non-substituted alkyl group with a carbon number of 2 or more and 20 or less or a substituted or non-substituted aryl group.

The invention as described in (9) is an electrochromic composition characterized in that the electrochromic compound as described in (7) or (8) is bonded or adsorbed to an electrically conductive or semi-conductive nano-structure.

The invention as described in (10) is an electrochromic composition characterized by being obtained by reacting a compound represented by a general formula of $$B-C-\underset{\underset{D^3}{|}}{\overset{\overset{D^1}{|}}{Si}}-D^2$$

(in the formula, B is a halogen group, C is an alkylene group, $D^1$ is a halogen group or an alkoxy group, each of $D^2$ and $D^3$ is independently a halogen group, an alkoxy group, or an alkyl group.)

with an electrically conductive or semi-conductive nano-structure and subsequently reacting a compound represented by a general formula of

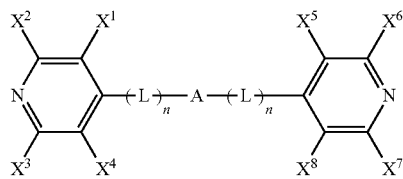

(in the formula, each of $X^1$, $X^2$, $X^3$, $X^4$, $X^5$, $X^6$, $X^7$, and $X^8$ is independently a hydrogen atom, a halogen group, a hydroxyl group, a nitro group, a cyano group, a carboxyl group, a substituted or non-substituted alkoxycarbonyl group, a substituted or non-substituted aryloxycarbonyl group, a substituted or non-substituted alkylcarbonyl group, a substituted or non-substituted arylcarbonyl group, an aminocarbonyl group, a substituted or non-substituted monoalkylaminocarbonyl group, a substituted or non-substituted dialkylaminocarbonyl group, a substituted or non-substituted monoarylaminocarbonyl group, a substituted or non-substituted diarylaminocarbonyl group, a sulfonate group, a substituted or non-substituted alkoxysulfonyl group, a substituted or non-substituted aryloxysulfonyl group, a substituted or non-substituted alkylsulfonyl group, a substituted or non-substituted arylsulfonyl group, an aminosulfonyl group, a substituted or non-substituted monoalkylaminosulfonyl group, a substituted or non-substituted dialkylaminosulfonyl group, a substituted or non-substituted monoarylaminosulfonyl group, a substituted or non-substituted diarylaminosulfonyl group, an amino group, a substituted or non-substituted monoalkylamino group, a substituted or non-substituted dialkylamino group, a substituted or non-substituted alkyl group, a substituted or non-substituted alkenyl group, a substituted or non-substituted alkynyl group, a substituted or non-substituted aryl group, a substituted or non-substituted alkoxy group, a substituted or non-substituted aryloxy group, a substituted or non-substituted alkylthio group, a substituted or non-substituted arylthio group, or a substituted or non-substituted heterocyclic group, A is a substituted or non-substituted 5-membered heterocyclic ring group containing one or more of N, O, S, or Se and containing C bonding to L, L is a substituted or non-substituted arylene group, and n is 1, 2, or 3.) therewith.

The invention as described in (11) is a display element including a display electrode, an opposing electrode provided to oppose and separate from the display electrode with a predetermined space, and an electrolyte interposed between the display electrode and the opposing electrode, characterized in that a display layer containing the electrochromic compound as described in (7) or (8) or the electrochromic composition as described in (9) or (10) is formed on a surface of the display electrode at an opposing electrode side.

The invention as described in (12) is a display device characterized by including the display element as described in (11) and a part configured to drive the display element.

The invention as described in (13) is an electrochromic compound characterized by being represented by the following general formula [3-1]

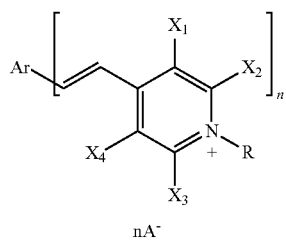

(in the general formula [3-1], each of $X_1$, $X_2$, $X_3$, and $X_4$ independently represents a hydrogen atom or a monovalent substitute, each of R independently represents a monovelent substitute, n represents an integer of 1 to 6, Ar represents a benzene ring which may have a substituent if n is 1 to 5 and simply represents a benzene ring if n is 6, and $A^-$ represents a monovalent anion).

The invention as described in (14) is the electrochromic compound as described in (13), characterized by containing a structure represented by the following general formula [3-2]

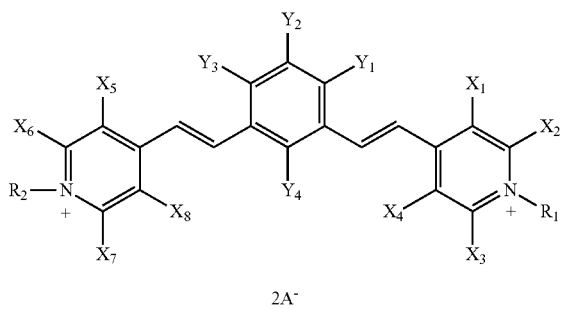

(in the general formula [3-2], each of $X_1$, $X_2$, $X_3$, $X_4$, $X_5$, $X_6$, $X_7$, $X_8$, $Y_1$, $Y_2$, $Y_3$, and $Y_4$ independently represents a hydrogen atom or a monovalent substituent, each of $R_1$ and $R_2$ independently represents a monovalent substitutent, and $A^-$ represents a monovalent anion).

The invention as described in (15) is the electrochromic compound as described in (13), characterized by containing a structure represented by the following general formula [3-3]

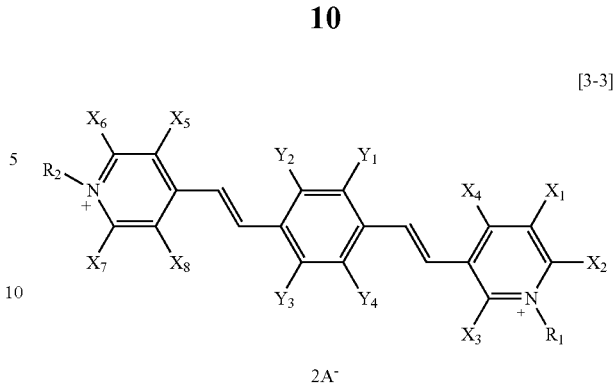

(in the general formula [3-3], each of $X_1$, $X_2$, $X_3$, $X_4$, $X_5$, $X_6$, $X_7$, $X_8$, $Y_1$, $Y_2$, $Y_3$, and $Y_4$ independently represents a hydrogen atom or a monovelent substituent, each of $R_1$ and $R_2$ independently represents a monovelent substitutent, and $A^-$ represents a monovalent anion).

The invention as described in (16) is the electrochromic compound as described in (15), characterized by containing a structure represented by the following general formula [3-4]

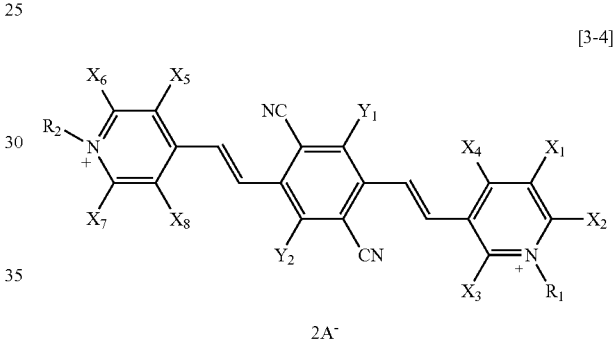

(in the general formula [3-4], each of $X_1$, $X_2$, $X_3$, $X_4$, $X_5$, $X_6$, $X_7$, $X_8$, $Y_1$, and $Y_2$ independently represents a hydrogen atom or a monovelent substituent, each of $R_1$ and $R_2$ independently represents a monovelent substitutent, and $A^-$ represents a monovalent anion).

The invention as described in (17) is the electrochromic compound as described in any of (13) to (16), characterized in that at least one of R or at least one of $R_1$ and $R_2$ is a functional group capable of bonding to a hydroxyl group directly or indirectly.

The invention as described in (18) is an electrochromic composition characterized by including an electrically conductive or semi-conductive nano-structure and the electrochromic compound as described in (17) being bonded or adsorbed to the nano-structure.

The invention as described in (19) is a display element including a display electrode, an opposing electrode provided to oppose and separate from the display electrode, and an electrolyte arranged between the display electrode and the opposing electrode, and having a display layer on a surface of the display electrode which opposes the opposing electrode, characterized in that the display layer contains at least the electrochromic compound as described in any of (13) to (17) or the electrochromic composition as described in (18).

The invention as described in (20) is an electrochromic compound characterized by being represented by the following structural formula [4-1]

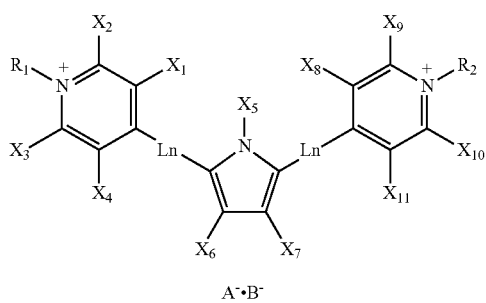

[4-1]

(in the structural formula [4-1], each of $X_1$-$X_4$ and $X_6$-$X_{11}$ independently a hydrogen atom or a monovalent substituent, $X_5$ represents an aryl group which may have a substituent or a heterocyclic group which may have a substituent, each of $R_1$ and $R_2$ independently represents a monovelent substituent, L represents an aromatic hydrocarbon group which may have a substituent, n is an integer of 0 to 3, and each of $A^-$ and $B^-$ independently represents a monovelent anion).

The invention as described in (21) is the electrochromic compound as described in (20), characterized in that at least one of $R_1$ and $R_2$ is a functional group capable of bonding to a hydroxyl group directly or indirectly.

The invention as described in (22) is an electrochromic composition characterized by including an electrically conductive or semi-conductive nano-structure and the electrochromic compound as described in (21) which is bonded or adsorbed to the nano-structure.

The invention as described in (23) is a display element including a display electrode, an opposing electrode provided to oppose and separate from the display electrode, and an electrolyte arranged between the display electrode and the opposing electrode, and having a display layer on a surface of the display electrode which opposes the opposing electrode, characterized in that the display layer contains at least the electrochromic compound as described in (20) or (21) or the electrochromic composition as descried in (22).

Advantageous Effect of the Invention

According to the present invention, it may be possible to provide an electrochromic compound and electrochromic composition capable of providing cyan color development or color erasing and a display element and display device having the electrochromic compound and electrochromic composition.

According to the present invention, it may be possible to provide an electrochromic compound and electrochromic composition capable of providing yellow color development and color erasing, and a display element and display device having the electrochromic compound and electrochromic composition.

According to the present invention, it may be possible to provide an electrochromic compound and electrochromic composition providing yellow-type color development, cyan-type color development and black-type color development. Furthermore, according to the present invention, it may be possible to provide a display element capable of providing a full color display, because the electrochromic compound or electrochromic composition is used.

According to the present invention, it may be possible to provide an electrochromic compound and electrochromic composition exhibiting a sharp light absorption spectrum characteristic at the time of color development, providing magenta-type color development, and having less coloring at the time of color erasing. Furthermore, according to the present invention, it may be possible to provide a display element capable of providing a full color display, because the electrochromic compound or electrochromic composition is used.

BRIEF DESCRIPTION OF THE DRAWINGS

FIGS. 18A and 18B are schematic diagrams illustrating an example of a configuration of a general display element using an electrochromic compound according to the present invention, wherein FIG. 18A and FIG. 18B illustrate a case of an electrochromic compound having no adsorption group and a case of an electrochromic compound having an adsorption group, respectively.

EXPLANATION OF LETTERS OR NUMERALS

Figure 1:
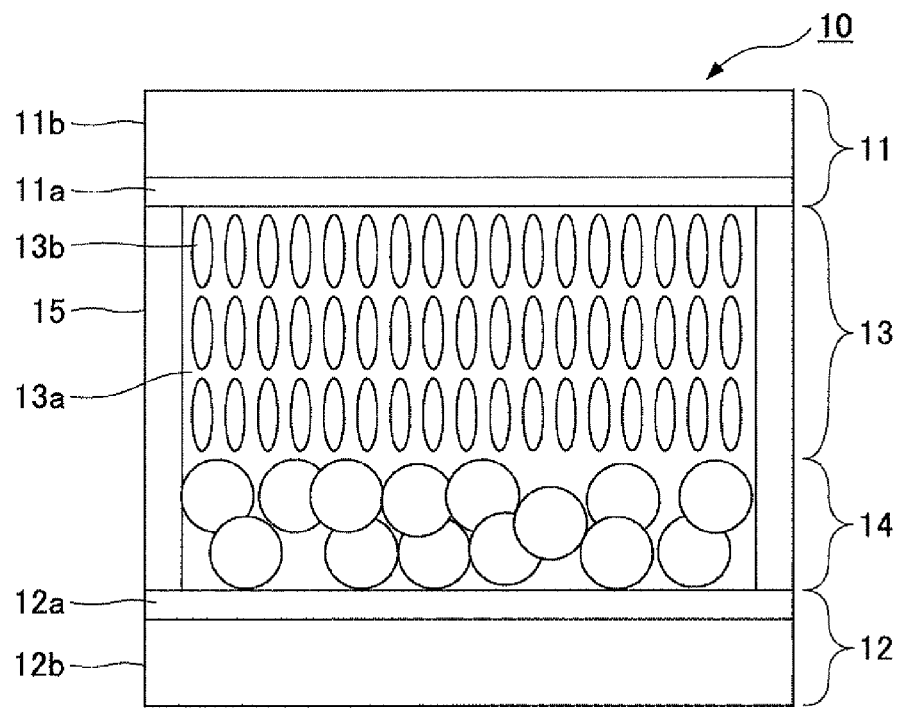
FIG. 1 is a diagram illustrating one example of a display element according to the present invention.

1 Display electrode
2 Opposing electrode
3 Electrolyte
4a, 4b Display layer
5a Organic electrochromic compound
5b Oxidation reduction color development part
5c Adsorption group (bonding group)
5d Spacer part
5e Organic electrochromic composition
6 White Color Reflective Layer
10, 20, 30 Display element
11 Display substrate
11a Display electrode
11b Transparent substrate
12 Opposing substrate
12a Opposing electrode
12b Substrate
13, 23 Display layer
13a Electrolyte liquid
13b Electrochromic compound
14 White color reflective layer
15 Spacer
33 Display layer
33b Electrochromic composition

BEST MODE FOR CARRYING OUT THE INVENTION

Next, an embodiment for implementing the present invention will be described in conjunction with the drawings.

An electrochromic compound according to the present invention is represented by a general formula of

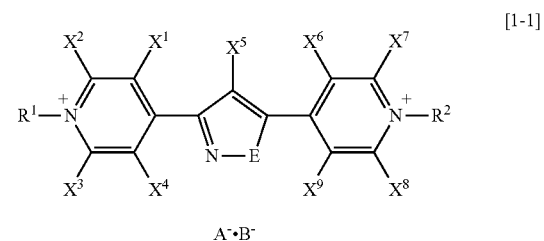

[1-1]

(in the formula, each of $X^1$, $X^2$, $X^3$, $X^4$, $X^5$, $X^6$, $X^7$, $X^8$, and $X^9$ is independently a hydrogen atom, a halogen group, a hydroxyl group, a nitro group, a cyano group, a carboxyl group, a substituted or non-substituted alkoxycarbonyl group, a substituted or non-substituted aryloxycarbonyl group, a substituted or non-substituted alkylcarbonyl group, a substituted or non-substituted arylcarbonyl group, an aminocarbonyl group, a substituted or non-substituted monoalkylaminocarbonyl group, a substituted or non-substituted dialkylaminocarbonyl group, a substituted or non-substituted monoarylaminocarbonyl group, a substituted or non-substituted diarylaminocarbonyl group, a sulfonate group, a substituted or non-substituted alkoxysulfonyl group, a substituted or non-substituted aryloxysulfonyl group, a substituted or non-substituted alkylsulfonyl group, a substituted or non-substituted arylsulfonyl group, an aminosulfonyl group, a substituted or non-substituted monoalkylaminosulfonyl group, a substituted or non-substituted dialkylaminosulfonyl group, a substituted or non-substituted monoarylaminosulfonyl group, a substituted or non-substituted diarylaminosulfonyl group, an amino group, a substituted or non-substituted monoalkylamino group, a substituted or non-substituted dialkylamino group, a substituted or non-substituted alkyl group, a substituted or non-substituted alkenyl group, a substituted or non-substituted alkynyl group, a substituted or non-substituted aryl group, a substituted or non-substituted alkoxy group, a substituted or non-substituted aryloxy group, a substituted or non-substituted alkylthio group, a substituted or non-substituted arylthio group, or a substituted or non-substituted heterocyclic group, each of $R^1$ and $R^2$ is independently a substituted or non-substituted alkyl group, a substituted or non-substituted alkenyl group, a substituted or non-substituted alkynyl group, or a substituted or non-substituted aryl group, E is an oxy group, a thio group, or a seleno group, each of $A^-$ and $B^-$ is independently a monovalent anion, and $R^1$ and/or $R^2$ may be substituted with one or more kinds of functional groups selected from the group consisting of a sulfonate group, a phosphonate group, a phosphate group, and a carboxyl group).

It may be possible for $X^1$, $X^2$, $X^3$, $X^4$, $X^5$, $X^6$, $X^7$, $X^8$, and $X^9$ to provide a solubility of an electrochromic compound in a solvent. Thereby, a process for preparing an electrochromic composition or a display element may become easier. Furthermore, it may be possible for an electrochromic compound according to the present invention to develop a cyan color, and when $X^1$, $X^2$, $X^3$, $X^4$, $X^5$, $X^6$, $X^7$, $X^8$, and $X^9$ are controlled, it may also be possible to develop a yellow or magenta color.

Additionally, when a stability such as a heat resistance or a light resistance is taken into consideration, it is preferable that each of $X^1$, $X^2$, $X^3$, $X^4$, $X^5$, $X^6$, $X^7$, $X^8$, and $X^9$ is independently a hydrogen atom, a halogen group, or a group with a carbon number of 1 to 6.

Furthermore, it is preferable that each of $R^1$ and $R^2$ is independently a substituted or non-substituted alkyl group with a carbon number of 2 to 20 or a substituted or non-substituted aryl group. Thereby, it may be possible to improve a solubility of an electrochromic compound according to the present invention. As a result, synthesis of an electrochromic compound according to the present invention may become easier whereby a yield is improved and further it may become easier to form a display layer. Furthermore, it may be possible for steric hindrance of $R^1$ and $R^2$ to suppress association of an electrochromic compound according to the present invention in a display layer, and it may be possible to reduce a defect in an oxidation-reduction reaction which is caused by such association. An alkyl group may be any of linear, branched, and cyclic, and a branched one is preferable when steric hindrance is taken into consideration.

A substituent in an alkyl group, alkenyl group, alkynyl group, or aryl group for $R^1$ and $R^2$ is not particularly limited and there is provided an alkyl group, an aryl group, an alkoxy group, a sulfonate group, a phosphonate group, a phosphate group, a carboxyl group, a trichlorosilyl group, a trialkoxysilyl group, a monochlorosilyl group, a monoalkoxysilyl group, or the like, wherein two or more kinds thereof may be used in combination. Among these, an alkyl group with a carbon number of 1 to 4; a halogen group such as a fluoro group, a chloro group, or a bromo group; a halogenated alkyl group such as a trifluoromethyl group, 2,2,2-trifluoroethyl group, or a pentafluoroethyl group is preferable.

A monovalent anion is not particularly limited and there is provided $Br^-$, $Cl^-$, $ClO_4^-$, $PF_6^-$, $BF_4^-$, or the like.

Additionally, it is preferable that an electrochromic compound according to the present invention has a symmetric structure from the viewpoint of facility of synthesis and stability.

An electrochromic compound according to the present invention is not particularly limited and there are provided electrochromic compounds (1-1) to (1-11).

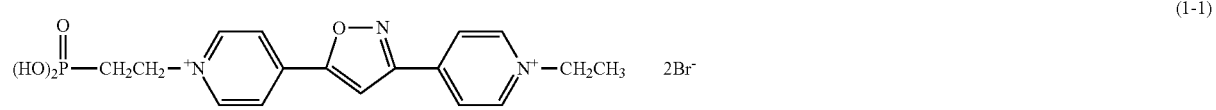

(1-1)

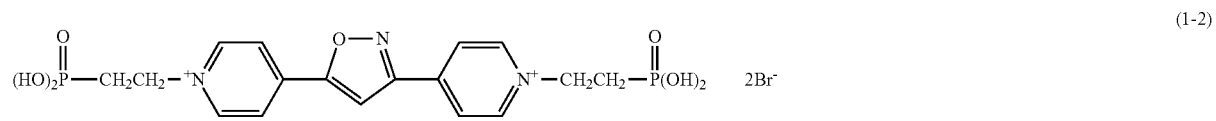

(1-2)

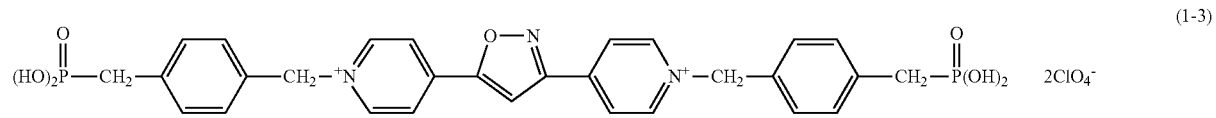

(1-3)

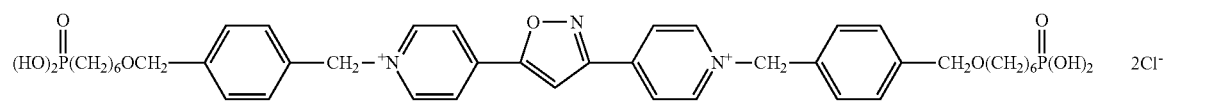

(1-4)

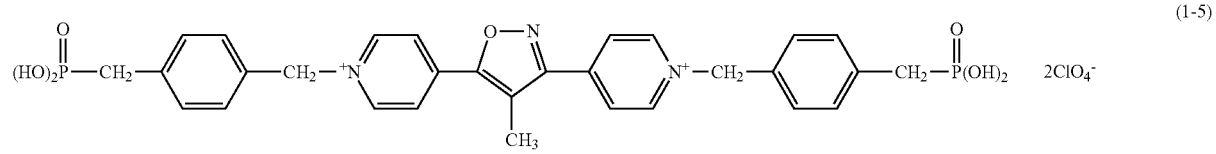

(1-5)

-continued

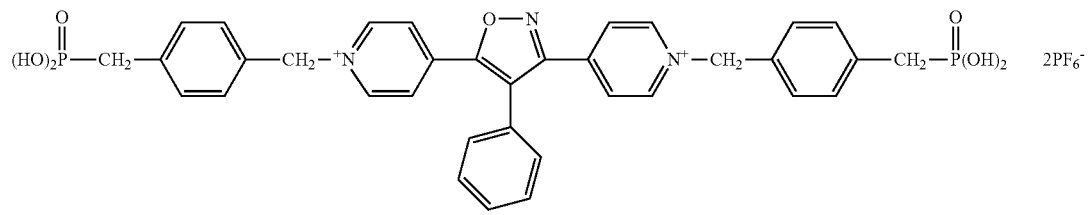
(1-6)

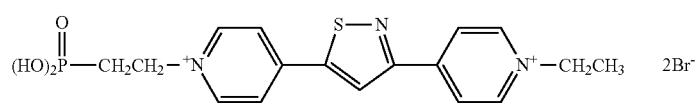
(1-7)

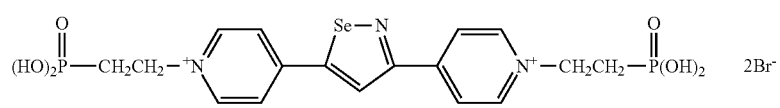
(1-8)

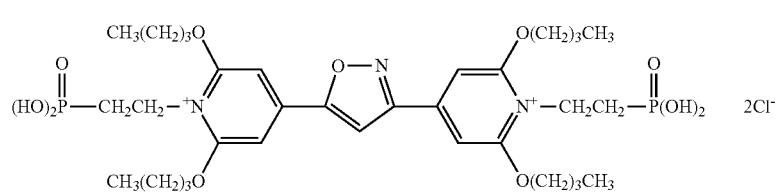
(1-9)

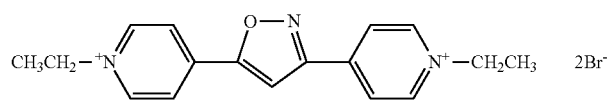
(1-10)

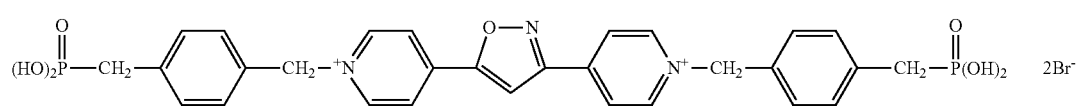
(1-11)

For example, when at least one of $X^1$, $X^2$, $X^3$, $X^4$, $X^5$, $X^6$, $X^7$, $X^8$, and $X^9$ is a carboxyl group or a sulphonate group and when $R^1$ and/or $R^2$ is substituted with one or more kinds of functional groups selected from the group composed of a sulfonate group, a phosphonate group, a phosphate group, and a carboxyl group, it may be possible for an electrochromic compound according to the present invention to bond or adsorb to an electrically conductive or semi-conductive nanostructure via hydrogen bonding or the like whereby it may be possible to obtain an electrochromic composition according to the present invention. Herein, it is preferable that $R^1$ and/or $R^2$ is/are substituted with a phosphonate group because a bonding force to an electrically conductive or semi-conductive structure may become larger.

Furthermore, an electrochromic composition according to the present invention is obtained by reacting a compound represented by a general formula of

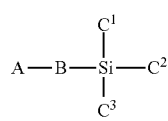

[1-2]

(in the formula, A is a halogen group, B is an alkylene group, $C^1$ is a halogen group or an alkoxy group, and each of $C^2$ and $C^3$ is independently a halogen group, an alkoxy group, or an alkyl group.)

with an electrically conductive or semi-conductive nanostructure and subsequently reacting a compound represented by a general formula of

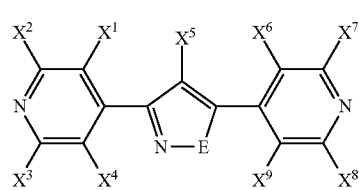

[1-3]

(in the formula, each of $X^1$, $X^2$, $X^3$, $X^4$, $X^5$, $X^6$, $X^7$, $X^8$, and $X^9$ is independently a hydrogen atom, a halogen group, a hydroxyl group, a nitro group, a cyano group, a carboxyl group, a substituted or non-substituted alkoxycarbonyl group, a substituted or non-substituted aryloxycarbonyl group, a substituted or non-substituted alkylcarbonyl group, a substituted or non-substituted arylcarbonyl group, an aminocarbonyl group, a substituted or non-substituted monoalkylaminocarbonyl group, a substituted or non-substituted dialkylaminocarbonyl group, a substituted or non-substituted monoarylaminocarbonyl group, a substituted or non-substituted diarylaminocarbonyl group, a sulfonate group, a substituted or non-substituted alkoxysulfonyl group, a substituted or non-substituted aryloxysulfonyl group, a substituted or non-substituted alkylsulfonyl group, a substituted or non-substituted arylsulfonyl group, an aminosulfonyl group, a substituted or non-substituted monoalkylaminosulfonyl group, a substituted or non-substituted dialkylaminosulfonyl group, a substituted or non-substituted monoarylaminosulfonyl group, a substituted or non-substituted diarylaminosulfonyl group, an amino group, a substituted or non-substituted monoalkylamino group, a substituted or non-substituted dialkylamino group, a substituted or non-substituted alkyl group, a substituted or non-substituted alkenyl group, a substituted or non-substituted alkynyl group, a substituted or non-substituted aryl group, a substituted or non-substituted alkoxy group, a substituted or non-substituted aryloxy group, a substituted or non-substituted alkylthio group, a substituted or non-substituted arylthio group, or a substituted or non-substituted heterocyclic group, and E is an oxy group, a thio group, or a seleno group.) therewith.

It may be possible for a compound represented by general formula [1-2] to react with a hydroxyl group on a surface of an electrically conductive or semi-conductive nano-structure and bond thereto via siloxane bonding. Herein, it is preferable that any of $C^1$, $C^2$, and $C^3$ is an alkoxy group such as an ethoxy group or a methoxy group or a chloro group because a bonding force to an electrically conductive or semi-conductive nano-structure may be larger. Furthermore, it is preferable that A is a bromo group and it is preferable that B is an alkylene group with a carbon number of 1 to 6.

It may be possible for $X^1$, $X^2$, $X^3$, $X^4$, $X^5$, $X^6$, $X^7$, $X^8$, and $X^9$ to provide a solubility of a compound represented by general formula [1-3] in a solvent. Thereby, a process for preparing an electrochromic composition or a display element may become easier. Furthermore, it may be possible for an electrochromic composition according to the present invention to develop a cyan color, and when $X^1$, $X^2$, $X^3$, $X^4$, $X^5$, $X^6$, $X^7$, $X^8$, and $X^9$ are controlled, it may also be possible to develop a yellow or magenta color.

Additionally, it is preferable that each of $X^1$, $X^2$, $X^3$, $X^4$, $X^5$, $X^6$, $X^7$, $X^8$, and $X^9$ is independently a hydrogen atom, a halogen group, or a group with a carbon number of 1 to 6, when a stability such as a heat resistance or a light resistance is taken into consideration.

Furthermore, it is preferable that a compound represented by general formula [1-3] has a symmetric structure, from the viewpoint of facility of synthesis and stability.

An electrochromic compound according to the present invention is represented by a general formula of

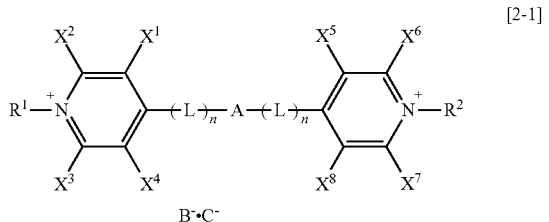

[2-1]

(in the formula, each of $X^1$, $X^2$, $X^3$, $X^4$, $X^5$, $X^6$, $X^7$, and $X^8$ is independently a hydrogen atom, a halogen group, a hydroxyl group, a nitro group, a cyano group, a carboxyl group, a substituted or non-substituted alkoxycarbonyl group, a substituted or non-substituted aryloxycarbonyl group, a substituted or non-substituted alkylcarbonyl group, a substituted or non-substituted arylcarbonyl group, an aminocarbonyl group, a substituted or non-substituted monoalkylaminocarbonyl group, a substituted or non-substituted dialkylaminocarbonyl group, a substituted or non-substituted monoarylaminocarbonyl group, a substituted or non-substituted diarylaminocarbonyl group, a sulfonate group, a substituted or non-substituted alkoxysulfonyl group, a substituted or non-substituted aryloxysulfonyl group, a substituted or non-substituted alkylsulfonyl group, a substituted or non-substituted arylsulfonyl group, an aminosulfonyl group, a substituted or non-substituted monoalkylaminosulfonyl group, a substituted or non-substituted dialkylaminosulfonyl group, a substituted or non-substituted monoarylaminosulfonyl group, a substituted or non-substituted diarylaminosulfonyl group, an amino group, a substituted or non-substituted monoalkylamino group, a substituted or non-substituted dialkylamino group, a substituted or non-substituted alkyl group, a substituted or non-substituted alkenyl group, a substituted or non-substituted alkynyl group, a substituted or non-substituted aryl group, a substituted or non-substituted alkoxy group, a substituted or non-substituted aryloxy group, a substituted or non-substituted alkylthio group, a substituted or non-substituted arylthio group, or a substituted or non-substituted heterocyclic group, each of $R^1$ and $R^2$ is independently a substituted or non-substituted alkyl group, a substituted or non-substituted alkenyl group, a substituted or non-substituted alkynyl group, or a substituted or non-substituted aryl group, A is a substituted or non-substituted 5-membered heterocyclic ring group containing one or more of N, O, S, or Se and containing C bonding to L, L is a substituted or non-substituted arylene group, each of $B^-$ and $C^-$ is independently a monovalent anion, n is 1, 2, or 3, and $R^1$ and/or $R^2$ may be substituted with one or more kinds of functional groups selected from the group consisting of a sulfonate group, a phosphonate group, a phosphate group, and a carboxyl group).

It may be possible for $X^1$, $X^2$, $X^3$, $X^4$, $X^5$, $X^6$, $X^7$, and $X^8$ to provide a solubility of an electrochromic compound in a solvent. Thereby, a process for preparing an electrochromic composition or a display element may become easier. Furthermore, it may be possible for an electrochromic compound according to the present invention to develop a yellow color, and when $X^1$, $X^2$, $X^3$, $X^4$, $X^5$, $X^6$, $X^7$, and $X^8$ are controlled, it may also be possible to develop a magenta or cyan color.

Additionally, when a stability such as a heat resistance or a light resistance is taken into consideration, it is preferable that each of $X^1$, $X^2$, $X^3$, $X^4$, $X^5$, $X^6$, $X^7$, and $X^8$ is independently a hydrogen atom, a halogen group, or a group with a carbon number of 1 to 6.

Furthermore, it is preferable that each of $R^1$ and $R^2$ is independently a substituted or non-substituted alkyl group with a carbon number of 2 to 20 or a substituted or non-substituted aryl group. Thereby, it may be possible to improve a solubility of an electrochromic compound according to the present invention. As a result, synthesis of an electrochromic compound according to the present invention may become easier whereby a yield is improved and further it may become easier to form a display layer. Furthermore, it may be possible for steric hindrance of $R^1$ and $R^2$ to suppress association of an electrochromic compound according to the present invention in a display layer, and it may be possible to reduce a defect in an oxidation-reduction reaction which is caused by such association. An alkyl group may be any of linear, branched, and cyclic, and a branched one is preferable when steric hindrance is taken into consideration.

A substituent in an alkyl group, alkenyl group, alkynyl group, or aryl group for $R^1$ and $R^2$ is not particularly limited and there is provided an alkyl group, an aryl group, an alkoxy group, a sulfonate group, a phosphonate group, a phosphate group, a carboxyl group, a trichlorosilyl group, a trialkoxysilyl group, a monochlorosilyl group, a monoalkoxysilyl group, or the like, wherein two or more kinds thereof may be used in combination. Among these, an alkyl group with a carbon number of 1 to 4; a halogen group such as a fluoro group, a chloro group, or a bromo group; a halogenated alkyl group such as a trifluoromethyl group, 2,2,2-trifluoroethyl group, or a pentafluoroethyl group is preferable.

A substituent in a heterocyclic group for A is not particularly limited and there is provided a halogen group such as a fluoro group, a chloro group, or a bromo group, a substituted or non-substituted alkyl group, aryl group, or alkoxy group, or the like.

For an arylene group for L, there is provided a phenylene group, a naphthylene group, or the like.

A substituent in an arylene group for L is not particularly limited and there is provided a halogen group such as a fluoro group, a chloro group, or a bromo group, a substituted or non-substituted alkyl group, aryl group, or alkoxy group, or the like, wherein two or more kinds thereof may be used in combination.

It may be possible for L to provide a solubility of an electrochromic compound in a solvent. Thereby, a process for preparing an electrochromic composition or a display element may become easier. Furthermore, it may be possible for an electrochromic compound according to the present invention to develop a yellow color, and when L is controlled, it may also be possible to develop a magenta or cyan color.

A monovalent anion is not particularly limited and there is provided $Br^-$, $Cl^-$, $ClO_4^-$, $PF_6^-$, $BF_4^-$, or the like.

Additionally, when a stability such as a heat resistance or a light resistance is taken into consideration, it is preferable that n is 1 or 2.

It is preferable that an electrochromic compound according to the present invention has a symmetric structure from the viewpoint of facility of synthesis and stability.

An electrochromic compound according to the present invention is not particularly limited and there are provided electrochromic compounds (2-1) to (2-15).

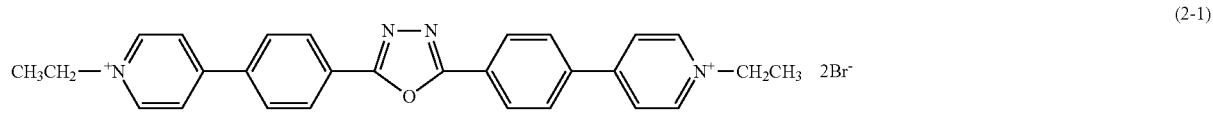

(2-1)

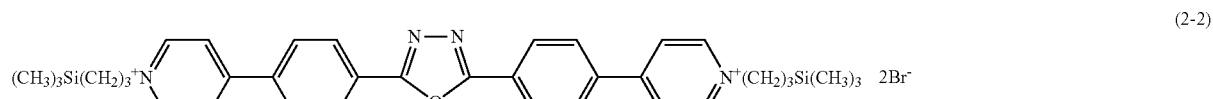

(2-2)

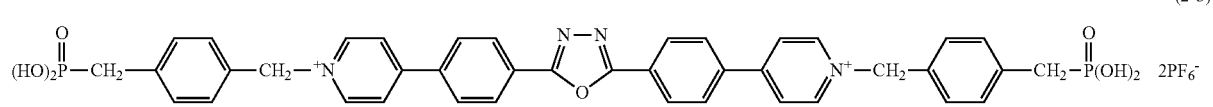

(2-3)

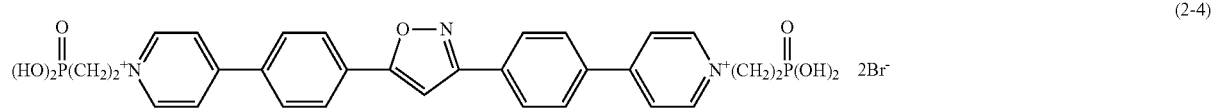

(2-4)

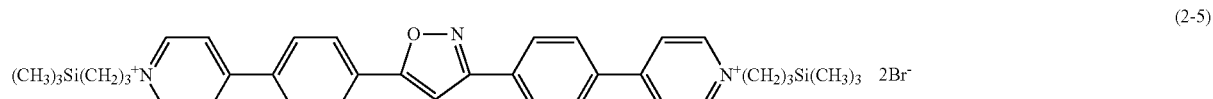

(2-5)

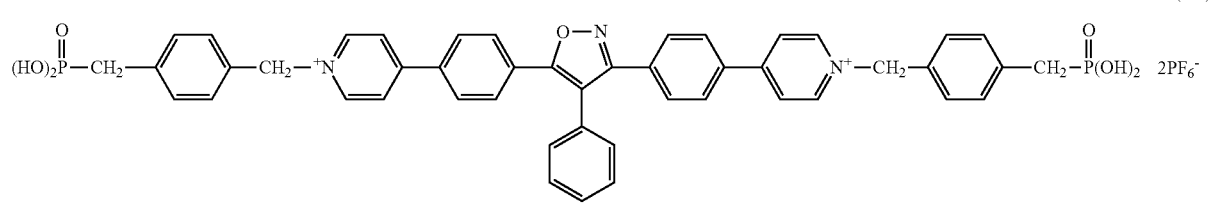

(2-6)

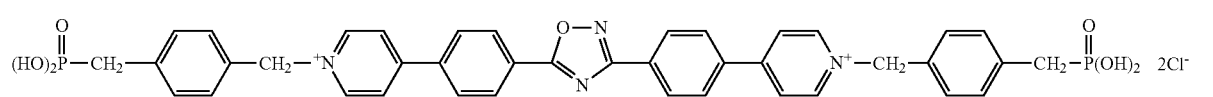

(2-7)

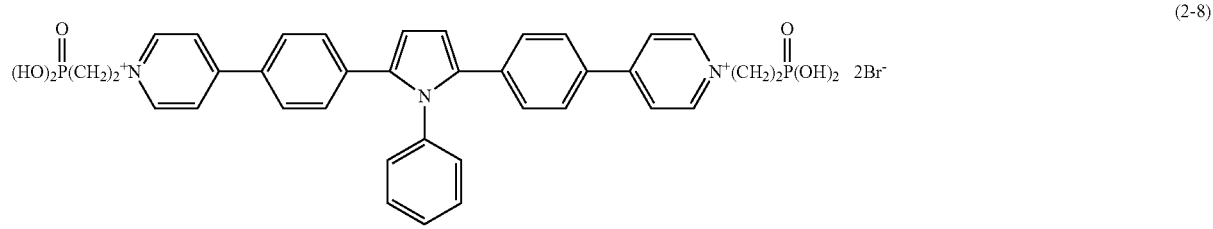

(2-8)

-continued (2-9)
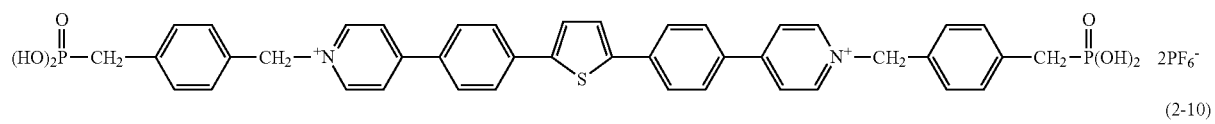

(2-10)
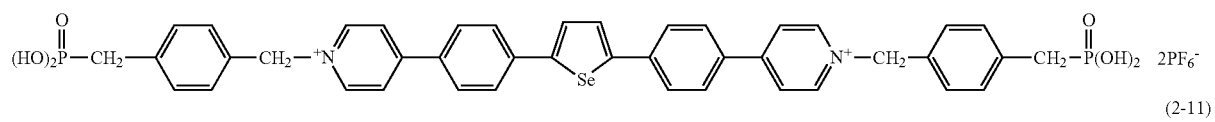

(2-11)
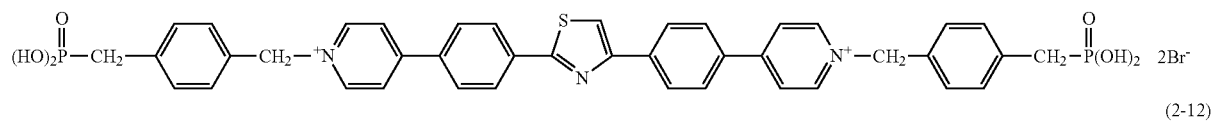

(2-12)
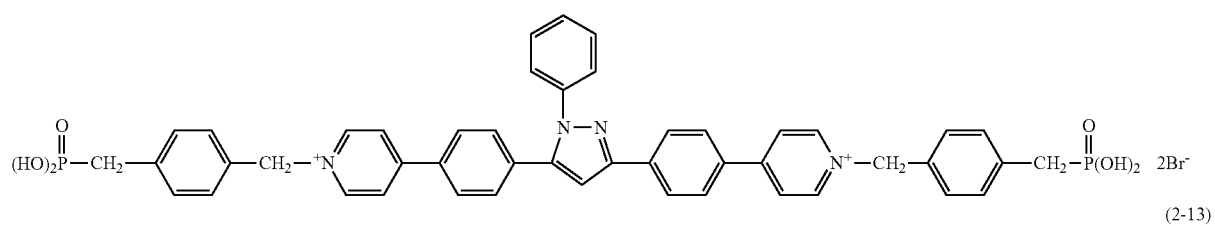

(2-13)
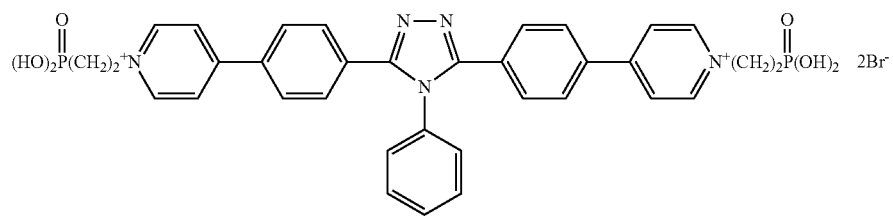

(2-14)
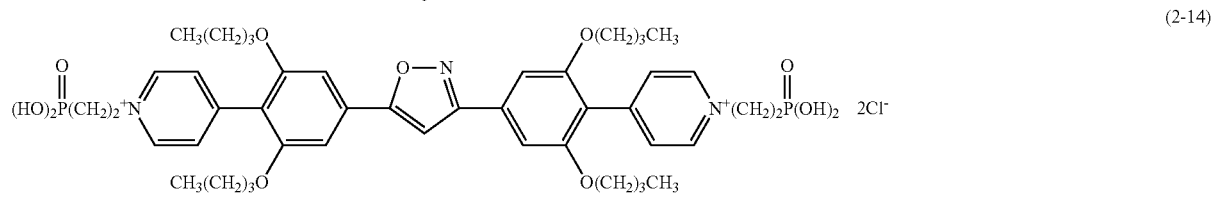

(2-15)
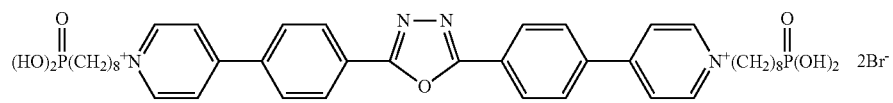

For example, when at least one of $X^1$, $X^2$, $X^3$, $X^4$, $X^5$, $X^6$, $X^7$, and $X^8$ is a carboxyl group or a sulphonate group and when $R^1$ and/or $R^2$ is substituted with one or more kinds of functional groups selected from the group composed of a sulfonate group, a phosphonate group, a phosphate group, and a carboxyl group, it may be possible for an electrochromic compound according to the present invention to bond or adsorb to an electrically conductive or semi-conductive nanostructure via hydrogen bonding or the like whereby it may be possible to obtain an electrochromic composition according to the present invention. Herein, it is preferable that $R^1$ and/or $R^2$ is/are substituted with a phosphonate group because a bonding force to an electrically conductive or semi-conductive structure may be larger.

Furthermore, an electrochromic composition according to the present invention is obtained by reacting a compound represented by a general formula of (2-2)
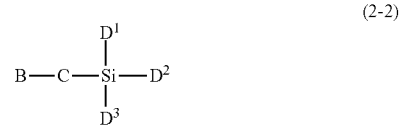

(in the formula, B is a halogen group, C is an alkylene group, $D^1$ is a halogen group or an alkoxy group, each of $D^2$ and $D^3$ is independently a halogen group, an alkoxy group, or an alkyl group.)
with an electrically conductive or semi-conductive nanostructure and subsequently reacting a compound represented by a general formula of

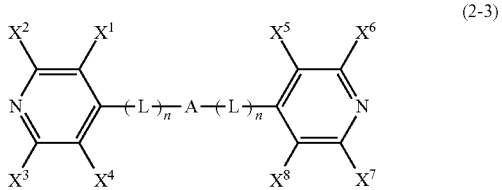

(2-3)

(in the formula, each of $X^1$, $X^2$, $X^3$, $X^4$, $X^5$, $X^6$, $X^7$, and $X^8$ is independently a hydrogen atom, a halogen group, a hydroxyl group, a nitro group, a cyano group, a carboxyl group, a substituted or non-substituted alkoxycarbonyl group, a substituted or non-substituted aryloxycarbonyl group, a substituted or non-substituted alkylcarbonyl group, a substituted or non-substituted arylcarbonyl group, an aminocarbonyl group, a substituted or non-substituted monoalkylaminocarbonyl group, a substituted or non-substituted dialkylaminocarbonyl group, a substituted or non-substituted monoarylaminocarbonyl group, a substituted or non-substituted diarylaminocarbonyl group, a sulfonate group, a substituted or non-substituted alkoxysulfonyl group, a substituted or non-substituted aryloxysulfonyl group, a substituted or non-substituted alkylsulfonyl group, a substituted or non-substituted arylsulfonyl group, an aminosulfonyl group, a substituted or non-substituted monoalkylaminosulfonyl group, a substituted or non-substituted dialkylaminosulfonyl group, a substituted or non-substituted monoarylaminosulfonyl group, a substituted or non-substituted diarylaminosulfonyl group, an amino group, a substituted or non-substituted monoalkylamino group, a substituted or non-substituted dialkylamino group, a substituted or non-substituted alkyl group, a substituted or non-substituted alkenyl group, a substituted or non-substituted alkynyl group, a substituted or non-substituted aryl group, a substituted or non-substituted alkoxy group, a substituted or non-substituted aryloxy group, a substituted or non-substituted alkylthio group, a substituted or non-substituted arylthio group, or a substituted or non-substituted heterocyclic group, A is a substituted or non-substituted 5-membered heterocyclic ring group containing one or more of N, O, S, or Se and containing C bonding to L, L is a substituted or non-substituted arylene group, and n is 1, 2, or 3.) therewith.

It may be possible for a compound represented by general formula [2-2] to react with a hydroxyl group on a surface of an electrically conductive or semi-conductive nano-structure and bond thereto via siloxane bonding. Herein, it is preferable that any of $D^1$, $D^2$, and $D^3$ is an alkoxy group such as an ethoxy group or a methoxy group or a chloro group because a bonding force to an electrically conductive or semi-conductive nano-structure may be larger. Furthermore, it is preferable that B is a bromo group and it is preferable that C is an alkylene group with a carbon number of 1 to 6.

It may be possible for $X^1$, $X^2$, $X^3$, $X^4$, $X^5$, $X^6$, $X^7$, and $X^8$ to provide a solubility of a compound represented by general formula [2-3] in a solvent. Thereby, a process for preparing an electrochromic composition or a display element may become easier. Furthermore, it may be possible for an electrochromic composition according to the present invention to develop a yellow color, and when $X^1$, $X^2$, $X^3$, $X^4$, $X^5$, $X^6$, $X^7$, and $X^8$ are controlled, it may also be possible to develop a magenta or cyan color.

Additionally, it is preferable that each of $X^1$, $X^2$, $X^3$, $X^4$, $X^5$, $X^6$, $X^7$, and $X^8$ is independently a hydrogen atom, a halogen group, or a group with a carbon number of 1 to 6, when a stability such as a heat resistance or a light resistance is taken into consideration.

A substituent in a heterocyclic group for A is not particularly limited and there is provided a halogen group such as a fluoro group, a chloro group, or a bromo group, a substituted or non-substituted alkyl group, aryl group, or alkoxy group, or the like.

For an arylene group for L, there is provided a phenylene group, a naphthylene group, or the like.

A substituent in an arylene group for L is not particularly limited and there is provided a halogen group such as a fluoro group, a chloro group, or a bromo group, a substituted or non-substituted alkyl group, aryl group, or alkoxy group, or the like, wherein two or more kinds thereof may be used in combination.

It may be possible for L to provide a solubility of a compound represented by general formula [2-3] in a solvent. Thereby, a process for preparing an electrochromic composition or a display element may become easier. Furthermore, it may be possible for an electrochromic composition according to the present invention to develop a yellow color, and when L is controlled, it may also be possible to develop a magenta or cyan color.

Additionally, when a stability such as a heat resistance or a light resistance is taken into consideration, it is preferable that n is 1 or 2.

It is preferable that a compound represented by general formula [2-3] has a symmetric structure from the viewpoint of facility of synthesis and stability.

A display element having a display layer containing thus obtained electrochromic composition according to the present invention may be excellent in an image memory characteristic, that is, an image retention characteristic.

It is preferable that a specific surface area of an electrically conductive or semi-conductive nano-structure is 100 $m^2$/g or more. Thereby, it may be possible to conduct surface treatment with an electrochromic compound efficiently and it may become possible to provide a multicolor display excellent in a contrast of a display at a color erasing state.

An electrically conductive or semi-conductive nano-structure is not particularly limited and there is provided a body having a convex-concave structure on a nano-scale such as a nano-particle accumulation or a nano-porous structure. It is preferable that an average primary particle diameter of a nano particle is 30 nm or less. Thereby, transmittance of light may be improved and a specific surface area may be larger.

It is preferable that an electrically conductive or semi-conductive nano-structure contains a metal oxide from the viewpoint of transparency or electrical conductivity. A metal oxide is not particularly limited and there is provided titanium oxide, zinc oxide, tin oxide, alumina, zirconium oxide, cerium oxide, silica, yttrium oxide, boron oxide, magnesium oxide, strontium titanate, potassium titanate, barium titanate, calcium titanate, calcium oxide, ferrite, hafnium oxide, tungsten oxide, iron oxide, copper oxide, nickel oxide, cobalt oxide, barium oxide, strontium oxide, vanadium oxide, calcium phosphate, aluminosilicate, or the like, wherein two or more kinds thereof may be used in combination. Among these, titanium oxide, zinc oxide, tin oxide, alumina, zirconium oxide, iron oxide, magnesium oxide, indium oxide, or tungsten oxide is more preferable, and titanium oxide is particularly preferable, because it may be possible to provide a multicolor image excellent in a response speed of color development or erasing.

FIG. 1 illustrates one example of a display element according to the present invention. A display element 10 includes a display substrate 11 on which a display electrode 11a is formed, an opposing substrate 12 on which an opposing electrode 12a is formed which is provided to oppose and separate from the display electrode 11a with a predetermined space, and a display layer 13 interposed between the display substrate 11 and the opposing substrate 12. Herein, the display layer 13 is provided such that an electrochromic compound 13b according to the present invention is dissolved in an electrolyte fluid 13a. Herein, an electrochromic compound 13b is subjected to an oxidation-reduction reaction on a surface of the display electrode 11 to conduct color development or erasing. Furthermore, the display element 10 is a reflection-type display element because a white color reflective layer 14 containing a white color particle is formed on a surface of the opposing electrode 12 at a side of the display electrode 11. Additionally, the display substrate 11 and the opposing substrate 12 are bonded via a spacer 15.

Figure 2:
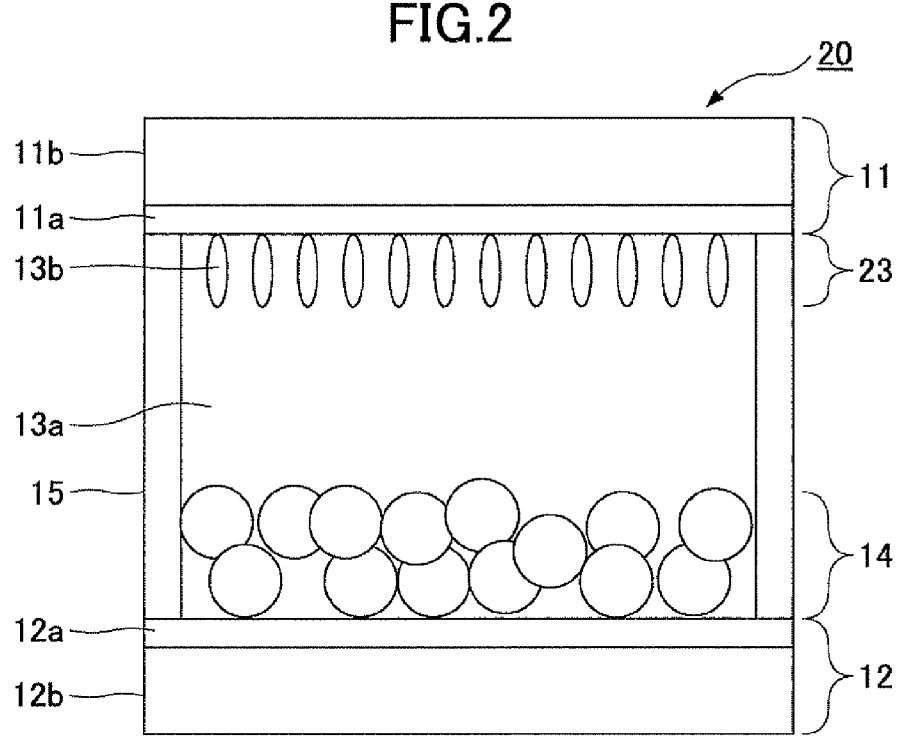
FIG. 2 is a diagram illustrating a variation of a display element in FIG. 1.

FIG. 2 illustrates a variation of a display element 10. A display element 20 has a configuration identical to that of the display element 10 except that a display layer 23 containing an electrochromic compound 13b, instead of the display layer 13, is formed on a surface of a display electrode 11a at a side of an opposing electrode 12. It may be possible to form the display layer 23 by using a dipping method, a vapor deposition method, a spin-coat method, a printing method, an ink jet method, or the like. Additionally, when $R^1$ and/or $R^2$ is/are substituted with one or more kinds of functional groups selected from the group composed of a sulfonate group, a phosphonate group, a phosphate group, a carboxyl group, a trichlorosilyl group, a trialkoxysilyl group, a monochlorosilyl group, and a monoalkoxysilyl group, it may be possible to subject the display electrode 11a having a hydroxyl group on a surface thereof to surface treatment with the electrochromic compound 13b.

Figure 3:
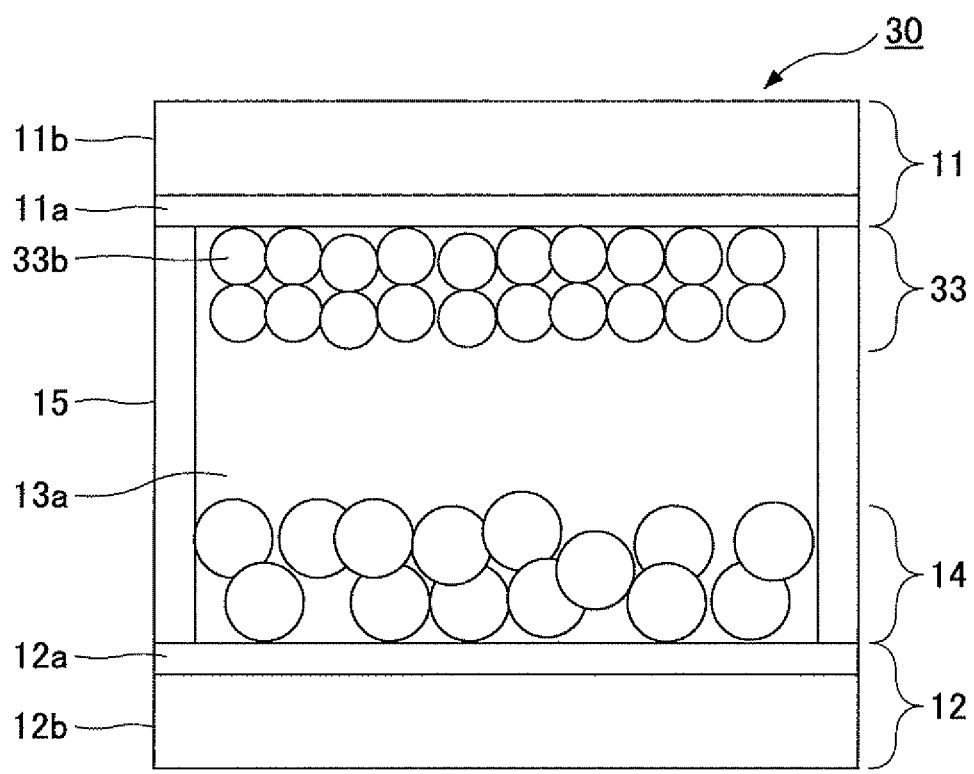
FIG. 3 is a diagram illustrating a variation of a display element in FIG. 1.

FIG. 3 illustrates a variation of a display element 10. A display element 30 has a configuration identical to that of the display element 10 except that a display layer 33 containing an electrochromic composition 33b according to the present invention, instead of the display layer 13, is formed on a surface of the display electrode 11a at a side of the opposing electrode 12b. It may be possible to form the display layer 33 by using a dipping method, a vapor deposition method, a spin-coat method, a printing method, an ink jet method, or the like.

The display substrate 11 is a transparent substrate 11b on which the display electrode 11a is formed.

A material for composing the display electrode 11a is not particularly limited as long as it is transparent, and there is provided an inorganic material such as tin-doped indium oxide (referred to as ITO below), fluorine-doped tin oxide (referred to as FTO below), or antimony-doped tin oxide (referred to as ATO below). Among these, an inorganic material including indium oxide, tin oxide, or zinc oxide is preferable, because it may be possible to form a thin film readily by using a sputter method, and InSnO, GaZnO, SnO, $In_2O_3$, or ZnO is particularly preferable.

For a material for composing the transparent substrate 11b, there is provided a glass, a plastic, or the like. Herein, when a plastic film is used for the transparent substrate 11b, it may be possible to manufacture a light-weight and flexible display element.

The opposing substrate 12 is a substrate 12b on which the opposing electrode 12a is formed.

A material composing the opposing electrode 12a is not particularly limited and there is provided ITO, FTO, zinc oxide, zinc, platinum, carbon, or the like. Herein, when the opposing electrode 12a includes a material which is reduced (or oxidized) when an electrochromic compound is oxidized (or reduced), it may be possible to obtain a display element capable of providing color development or color erasing stably.

For a material composing the substrate 12b, there is provided a glass, a plastic, or the like.

Additionally, a metal plate such as a zinc plate may be used instead of the opposing substrate 12.

For an electrolyte liquid 13a, a solution in which a supporting electrolyte is dissolved in a solvent, an ionic liquid, or the like is used. Hence, a higher ionic conductance may be provided.

A supporting electrolyte is not particularly limited and there is provided a metal salt such as $LiClO_4$, $LiBF_4$, $LiAsF_6$, $LiPF_6$, $CF_3SO_3Li$, $CF_3COOLi$, KCl, $NaClO_3$, NaCl, $NaBF_4$, NaSCN, $KBF_4$, $Mg(ClO_4)_2$, or $Mg(BF_4)_2$; a quaternary ammonium salt such as tetrabutylammonium perchlorate or tetrabutylammonium hexafluorophosphate; or the like.

A solvent is not particularly limited and there is provided propylene carbonate, acetonitrile, γ-butyrolactone, ethylene carbonate, sulfolane, dioxolane, tetrahydrofuran, 2-methyltetrahydrofuran, dimethyl sulfoxide, 1,2-dimethoxyethane, 1,2-ethoxymethoxyethane, polyethylene glycol, an alcohol, or the like.

Additionally, a gel-like electrolyte; or a solid electrolyte such as a polymer electrolyte may be used instead of the electrolyte 13a. For a polymer electrolyte, there is provided a perfluorosulfonate-type polymer or the like. Thereby, it may be possible to manufacture a display element excellent in a durability thereof.

It may be possible to form a white color reflective layer 14 by applying a coating liquid containing a white cooler pigment particle and a resin onto the opposing electrode 12.

A white color pigment particle is not particularly limited and there is provided a metal oxide such as titanium oxide, aluminum oxide, zinc oxide, silicon oxide, cesium oxide, or yttrium oxide.

It is preferable that an average particle diameter of a white color pigment particle is 50 to 400 nm, when a reflectance is taken into consideration. Additionally, a white color pigment particle may be dispersed in a polymer electrolyte instead of forming the white color reflective layer 14.

A method for driving a display element 10, 20, or 30 is not particularly limited as long as it is possible to apply a predetermined voltage between the display electrode 11a and the opposing electrode 12a. Herein, when a method of passive driving is used, it may be possible to obtain an inexpensive display device. Alternatively, when a method of active driving is used, it may be possible to obtain a display device capable of providing a highly fine display at a higher speed. Additionally, it may be possible to conduct active driving readily by providing an active driving element on the opposing substrate 12.

It may be possible to apply a display element 10, 20, or 30 to a display device such as an electronic book, an electronic signage, or an electronic inventory tag.

<Electrochromic Compound and Electrochromic Composition>

An electrochromic compound according to the present invention is characterized by being represented by any one of the following general formulas [3-1] to [3-4].

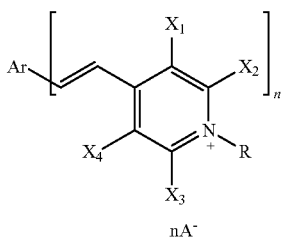

[3-1]

(In general formula [3-1], each of $X_1$, $X_2$, $X_3$, and $X_4$ independently represents a hydrogen atom or a monovalent substitute, each of R independently represents a monovelent substitute, n represents an integer of 1 to 6, Ar represents a benzene ring which may have a substituent if n is 1 to 5 and simply represents a benzene ring if n is 6, and $A^-$ represents a monovalent anion.)

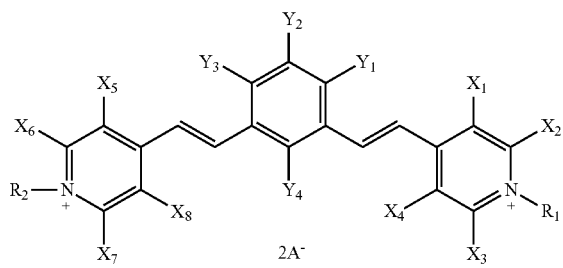

[3-2]

(In general formula [3-2], each of $X_1$, $X_2$, $X_3$, $X_4$, $X_5$, $X_6$, $X_7$, $X_8$, $Y_1$, $Y_2$, $Y_3$, and $Y_4$ independently represents a hydrogen atom or a monovalent substituent, each of $R_1$ and $R_2$ independently represents a monovalent substitutent, and $A^-$ represents a monovalent anion.)

An electrochromic compound represented by general formula [3-2] may exhibit a sharp light absorption spectrum characteristic at the time of color development thereof and provide a yellow-type color development thereof.

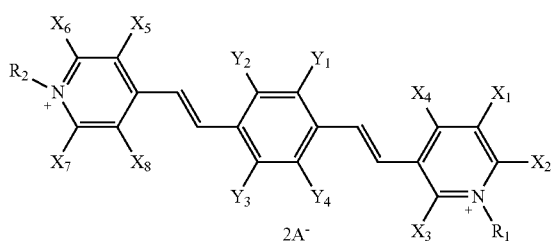

[3-3]

(In general formula [3-3], each of $X_1$, $X_2$, $X_3$, $X_4$, $X_5$, $X_6$, $X_7$, $X_8$, $Y_1$, $Y_2$, $Y_3$, and $Y_4$ independently represents a hydrogen atom or a monovelent substituent, each of $R_1$ and $R_2$ independently represents a monovelent substitutent, and $A^-$ represents a monovalent anion.)

An electrochromic compound represented by general formula [3-3] may exhibit a sharp light absorption spectrum characteristic at the time of color development thereof and provide a cyan-type color development thereof.

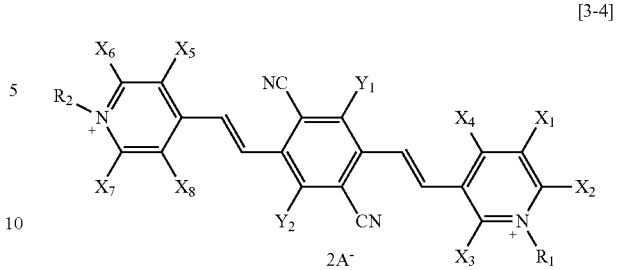

[3-4]

(In general formula [3-4], each of $X_1$, $X_2$, $X_3$, $X_4$, $X_5$, $X_6$, $X_7$, $X_8$, $Y_1$, and $Y_2$ independently represents a hydrogen atom or a monovelent substituent, each of $R_1$ and $R_2$ independently represents a monovelent substitutent, and $A^-$ represents a monovalent anion.)

An electrochromic compound represented by general formula [3-4] may exhibit a broad light absorption spectrum characteristic all over the wavelength region at the time of color development thereof and provide a black-type color development thereof.

For a specific example of $X_1$, $X_2$, $X_3$, $X_4$, $X_5$, $X_6$, $X_7$, $X_8$, $Y_1$, $Y_2$, $Y_3$, and $Y_4$, there is provided a hydrogen atom, a halogen group, a hydroxyl group, a nitro group, a cyano group, a carboxyl group, an alkoxycarbonyl group which may have a substituent, an aryloxycarbonyl group which may have a substituent, an alkylcarbonyl group which may have a substituent, an arylcarbonyl group which may have a substituent, an amide group, a monoalkylaminocarbonyl group which may have a substituent, a dialkylaminocarbonyl group which may have a substituent, a monoarylaminocarbonyl group which may have a substituent, a diarylaminocarbonyl group which may have a substituent, a sulfonate group, an alkoxysulfonyl group which may have a substituent, an aryloxysulfonyl group which may have a substituent, an alkylsulfonyl group which may have a substituent, an arylsulfonyl group which may have a substituent, a sulfonamide group, a monoalkylaminosulfonyl group which may have a substituent, a dialkylaminosulfonyl group which may have a substituent, a monoarylaminosulfonyl group which may have a substituent, a diarylaminosulfonyl group which may have a substituent, an amino group, a monoalkylamino group which may have a substituent, a dialkylamino group which may have a substituent, an alkyl group which may have a substituent, an alkenyl group which may have a substituent, an alkynyl group which may have a substituent, an aryl group which may have a substituent, an alkoxy group which may have a substituent, an aryloxy group which may have a substituent, an alkylthio group which may have a substituent, an arylthio group which may have a substituent, a heterocyclic group which may have a substituent, or the like.

It may be possible for groups represented by $X_1$, $X_2$, $X_3$, $X_4$, $X_5$, $X_6$, $X_7$, and $X_8$ to provide a solubility of an electrochromic compound in a solvent whereby a process manufacturing an element may be facilitated. Furthermore, it may become possible to control a color development spectrum (color) finely. On the other hand, these groups may readily degrade a stability such as a heat resistance or a light resistance, and a hydrogen atom, a halogen, or a substituent with a carbon number of 6 or less is preferable. Moreover, a hydrogen atom or a substituent with a carbon number of 3 or less is particularly preferable.

For a specific example of R, $R^1$, and $R^2$, there is provided an alkyl group which may have a substituent, an alkenyl group which may have a substituent, an alkynyl group which may have a substituent, an aryl group which may have a substituent, or the like. Furthermore, at least one of R, R$_1$, and R$_2$ may be a functional group capable of bonding to a hydroxyl group directly or indirectly. It may be only necessary for a functional group capable of bonding to a hydroxyl group directly or indirectly to be a functional group capable of bonding to a hydroxyl group directly or indirectly via hydrogen bonding, adsorption, chemical reaction, or the like, and its structure is not limited, wherein, for a preferable example, there is provided a phosphonate group, a phosphate group, a carboxyl group, a trichlorosilyl group, a trialkoxysilyl group, a monochlorosilyl group, a monoalkoxysilyl group, or the like. For a trialkoxysilyl group, a triethoxysilyl group, a trimethoxysilyl group, or the like is preferable.

Among these, a trialkoxysilyl group or a phosphonate group which may provide a higher bonding force to an electrically conductive or semi-conductive nano-structure (as described below) is particularly preferable.

A$^-$ represents a monovalent anion and is not particularly limited as long as it may be possible to provide a pair with a cationic part stably, and a Br ion, a Cl ion, a ClO$_4$ ion, a PF$_6$ ion, a BF$_4$ ion or the like is preferable. Furthermore, a Br ion or a Cl ion is particularly preferable.

Additionally, it is desirable that an electrochromic compound according to the present invention has X$_1$ to X$_8$ and R so as to provide a symmetric structure from the viewpoint of facility of synthesis thereof and improvement of stability thereof.

Specific structural formulas (3-5) to (3-58) of an electrochromic compound according to the present invention will be described below and an electrochromic compound according to the present invention is not limited to these examples.

[3-5]

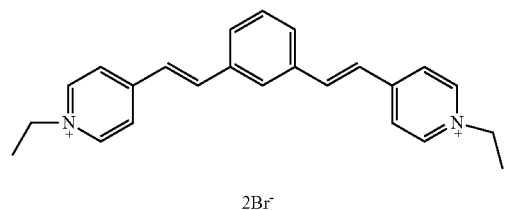

[3-6]

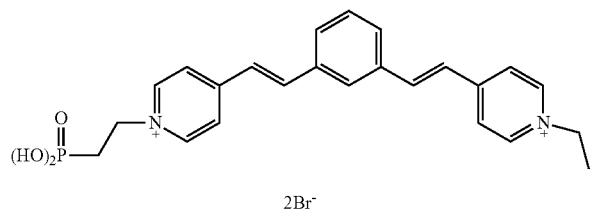

[3-7]

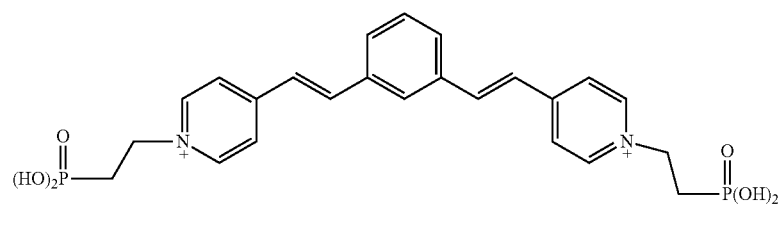

[3-8]

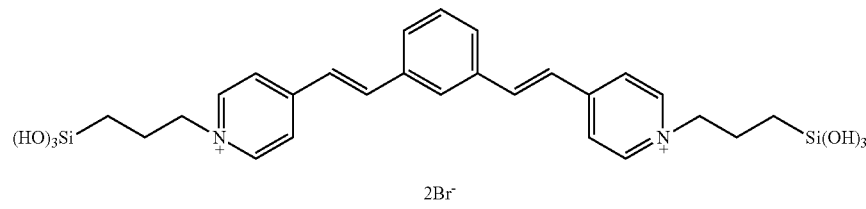

[3-9]

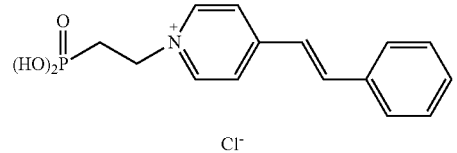

[3-10]

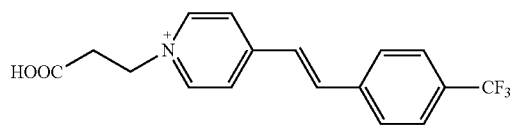

[3-11]

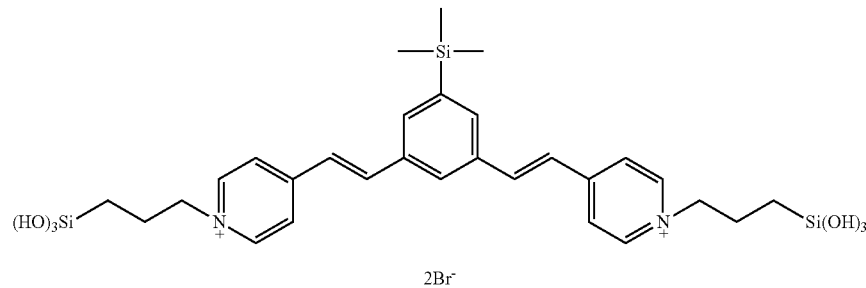

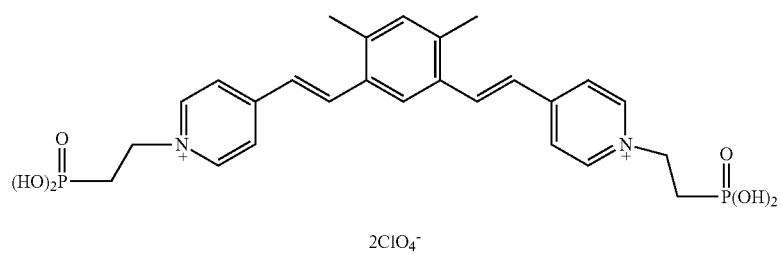
[3-12]
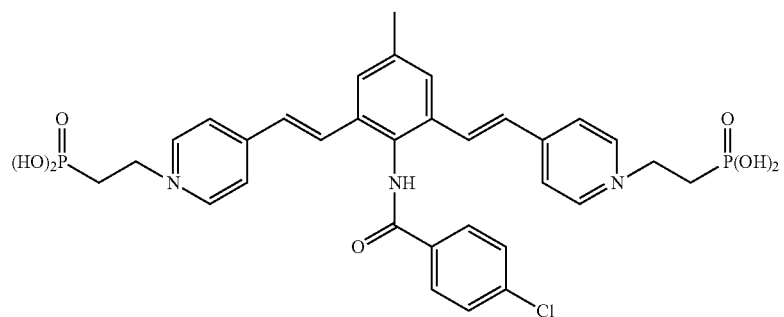
[3-13]
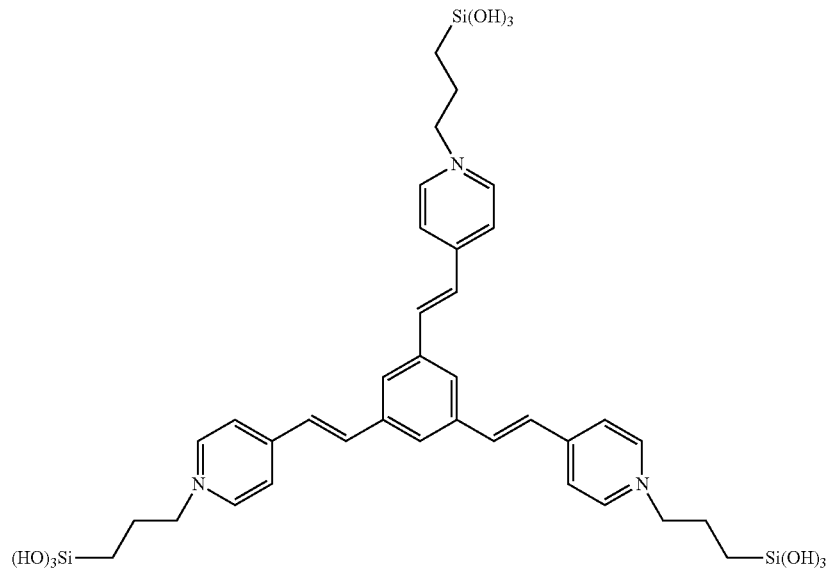
[3-14]
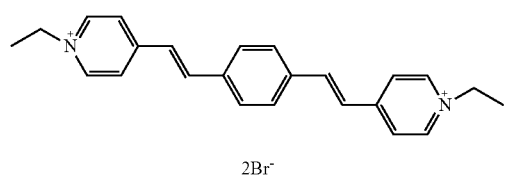
[3-15]
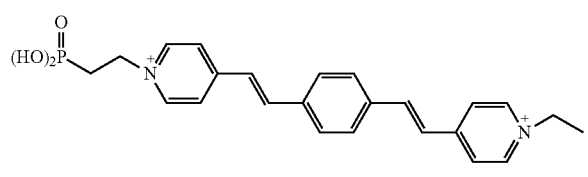
[3-16]

-continued

[3-26]
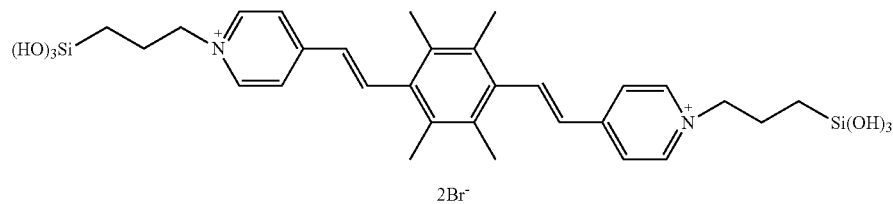
2Br⁻
[3-27]
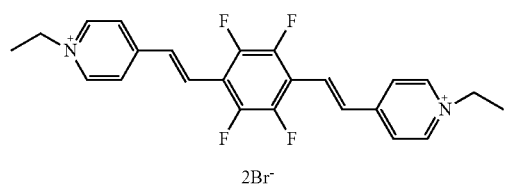
2Br⁻
[3-28]
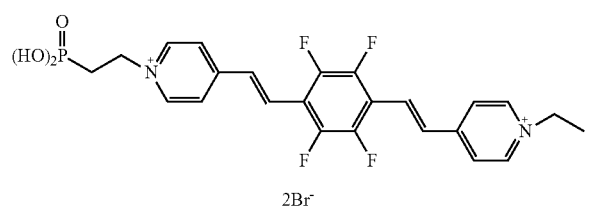
2Br⁻
[3-29]
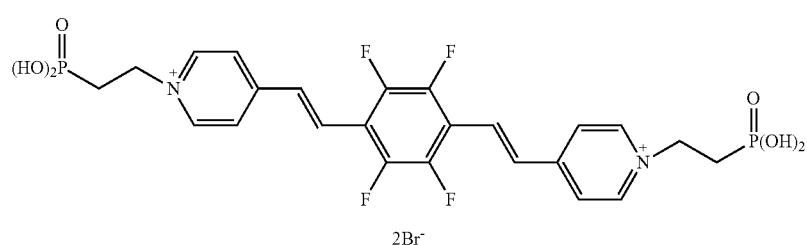
2Br⁻
[3-30]
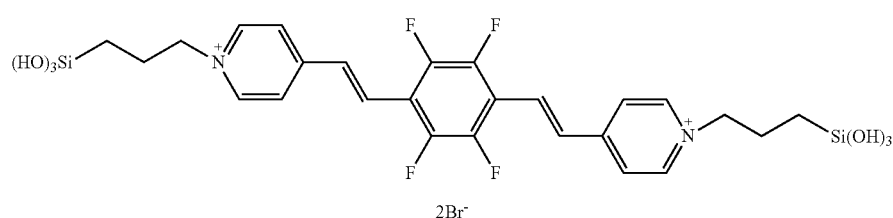
2Br⁻
[3-31]
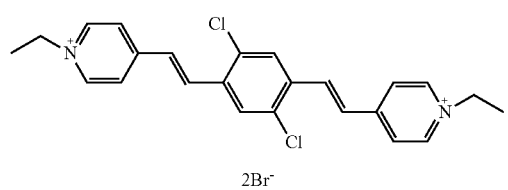
2Br⁻
[3-32]
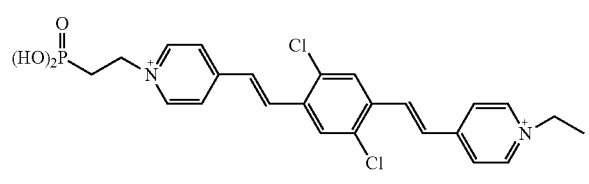
2Br⁻
[3-33]
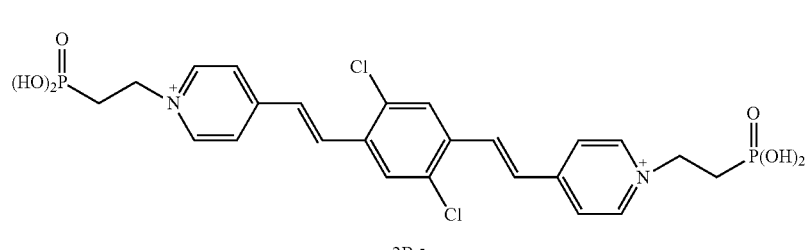
2Br⁻
[3-34]
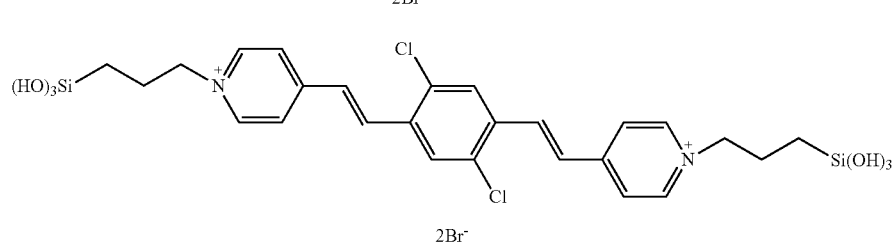
2Br⁻

[3-35]
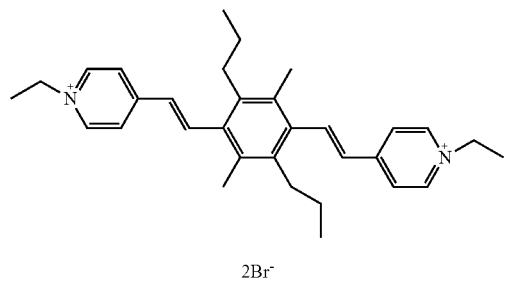
2Br⁻
[3-36]
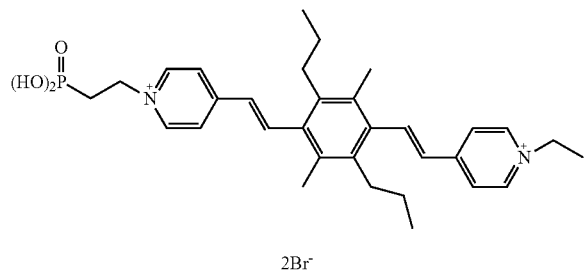
2Br⁻
[3-37]
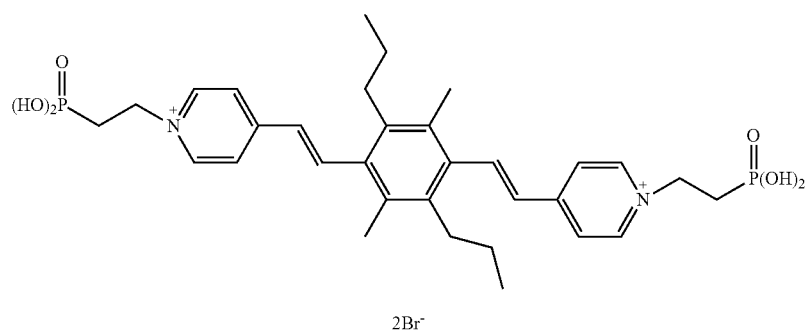
2Br⁻
[3-38]
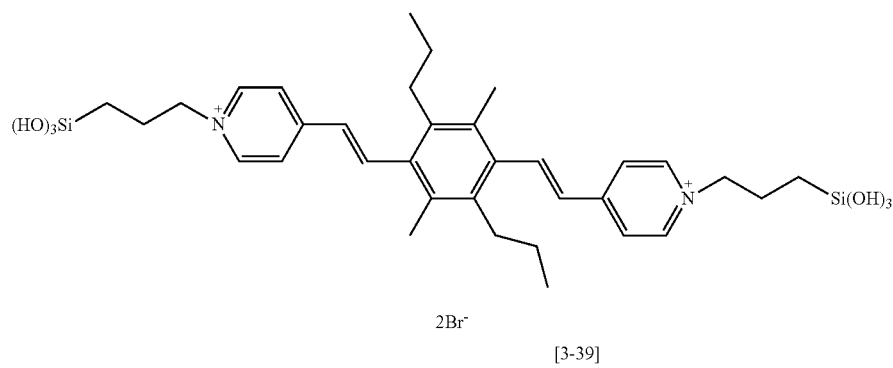
2Br⁻
[3-39]
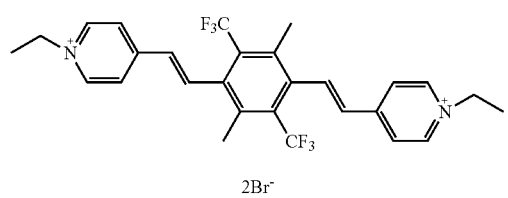
2Br⁻
[3-40]
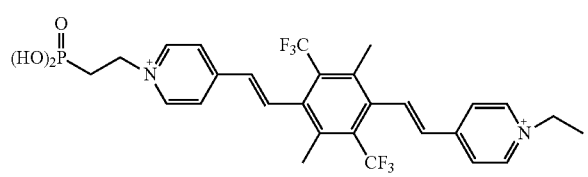
2Br⁻
[3-41]
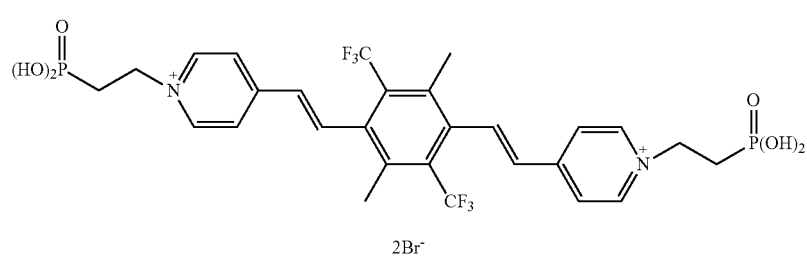
2Br⁻

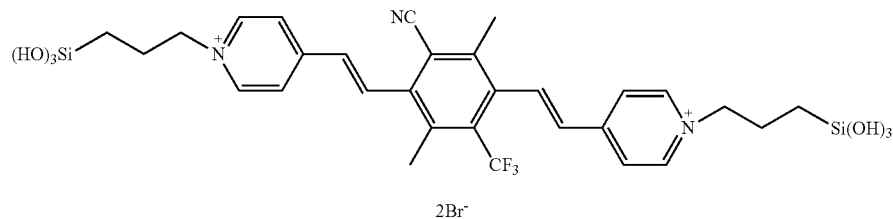
[3-42]
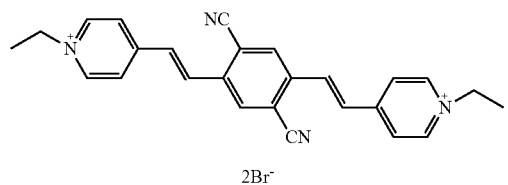
[3-43]
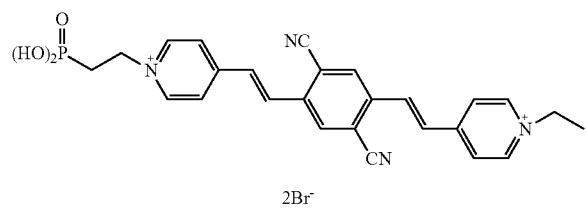
[3-44]
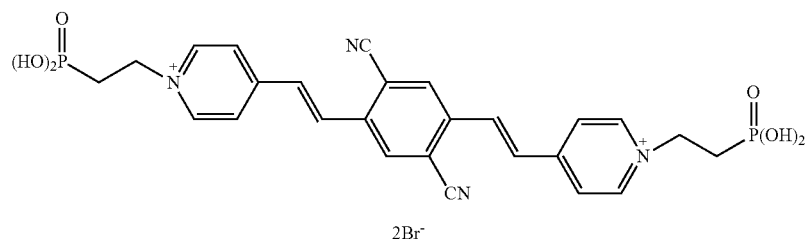
[3-45]
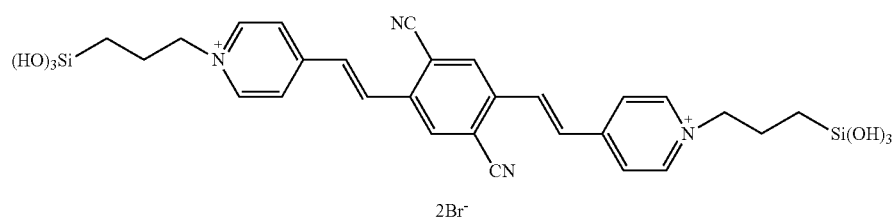
[3-46]
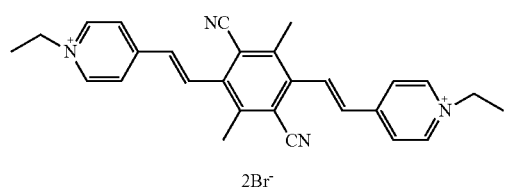
[3-47]
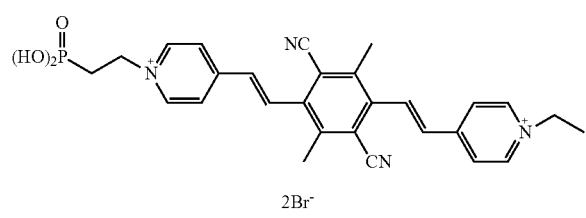
[3-48]
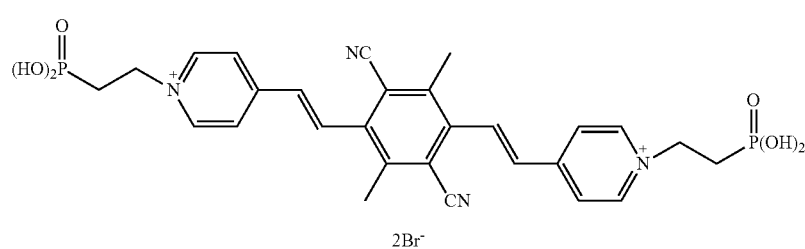
[3-49]

[3-50]
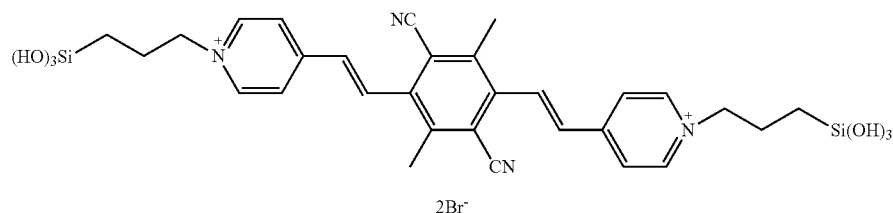
[3-51]
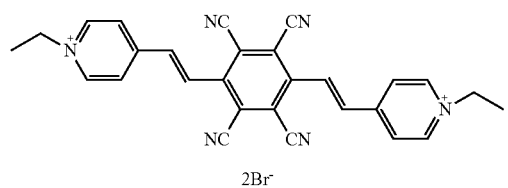
[3-52]
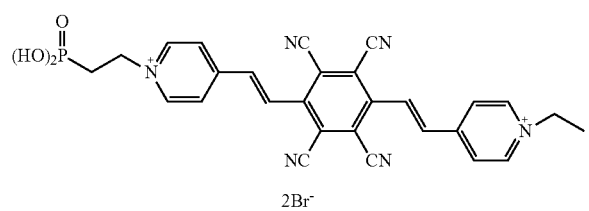
[3-53]
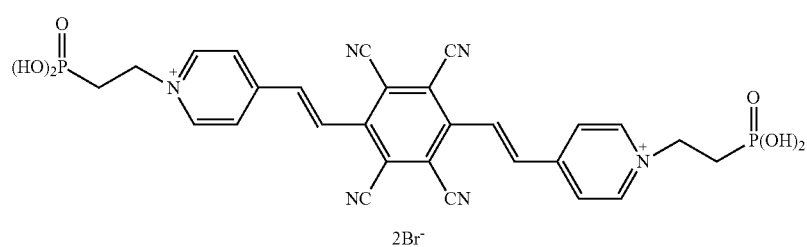
[3-54]
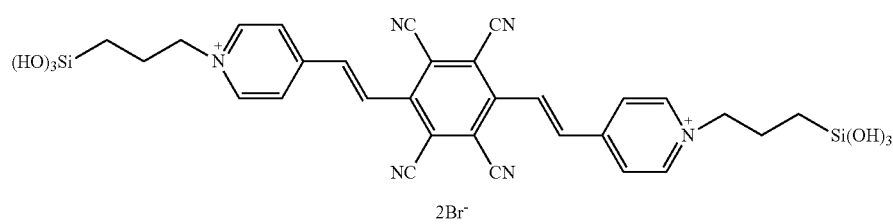
[3-55]
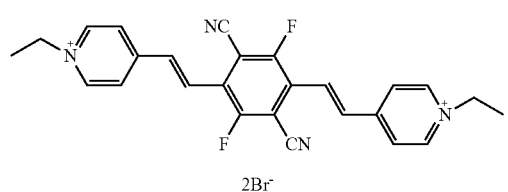
[3-56]
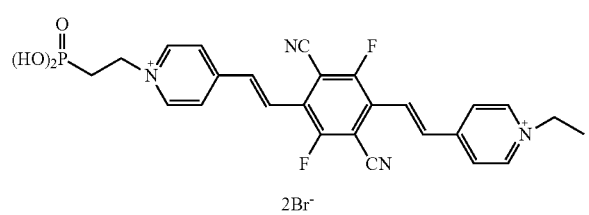
[3-57]
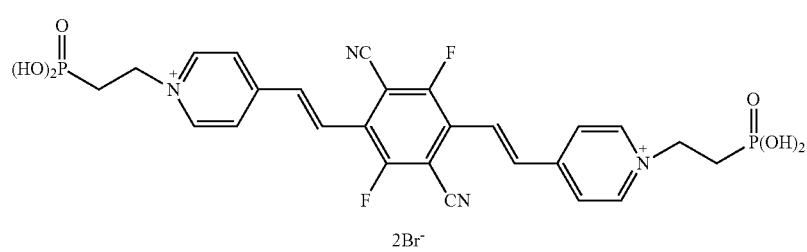

-continued

[3-58]

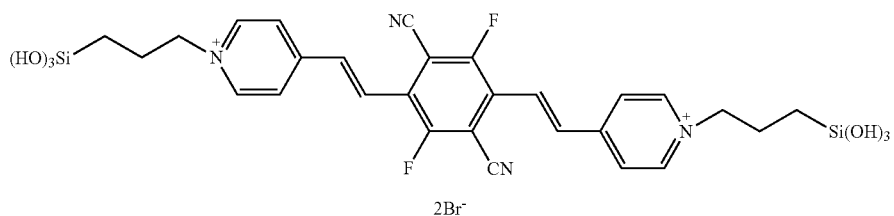

Furthermore, an electrochromic composition according to the present invention is characterized in that an electrochromic compound according to the present invention (an electrochromic compound represented by any one of general formulas [3-1] to [3-4]) is bonded or adsorbed to an electrically conductive or semi-conductive nano-structure. When an electrochromic composition according to the present invention is used for an electrochromic display element, it may be possible to provide yellow, cyan, or black color development and further to be excellent in an image memory characteristic, that is, an image color development retention characteristic. Additionally, an electrically conductive or semi-conductive nano-structure is a body having a convex-concave structure on a nano-scale such as a nano-particle or a nano-porous structure.

<Electrochromic Compound and Electrochromic Composition>

An electrochromic compound according to the present invention is characterized by being represented by the following structural formula [4-1].

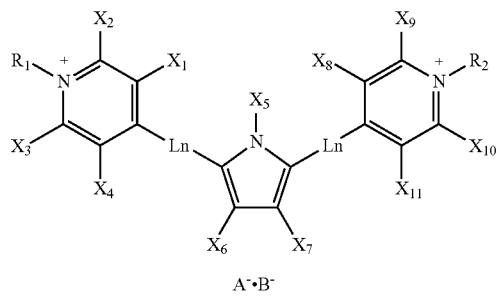

$A^- \cdot B^-$

In the structural formula [4-1], each of $X_1$-$X_4$ and $X_6$-$X_{11}$ independently a hydrogen atom or a monovalent substituent, $X_5$ represents an aryl group which may have a substituent or a heterocyclic group which may have a substituent, each of $R_1$ and $R_2$ independently represents a monovelent substituent, L represents an aromatic hydrocarbon group which may have a substituent, n is an integer of 0 to 3, and each of $A^-$ and $B^-$ independently represents a monovelent anion.

An electrochromic compound represented by structural formula [4-1] may exhibit a sharp light absorption spectrum characteristic at the time of color development thereof, provide a magenta-type color development thereof, and provide less coloring at the time of color erasing thereof.

For a specific example of $X_1$ to $X_4$ and $X_6$ to $X_{11}$, there is provided a hydrogen atom, a halogen atom, a hydroxyl group, a nitro group, a cyano group, a carboxyl group, an alkoxycarbonyl group which may have a substituent, an aryloxycarbonyl group which may have a substituent, an alkylcarbonyl group which may have a substituent, an arylcarbonyl group which may have a substituent, an amide group, a monoalkylaminocarbonyl group which may have a substituent, a dialkylaminocarbonyl group which may have a substituent, a monoarylaminocarbonyl group which may have a substituent, a diarylaminocarbonyl group which may have a substituent, a sulfonate group, an alkoxysulfonyl group which may have a substituent, an aryloxysulfonyl group which may have a substituent, an alkylsulfonyl group which may have a substituent, an arylsulfonyl group which may have a substituent, a sulfonamide group, a monoalkylaminosulfonyl group which may have a substituent, a dialkylaminosulfonyl group which may have a substituent, a monoarylaminosulfonyl group which may have a substituent, a diarylaminosulfonyl group which may have a substituent, an amino group, a monoalkylamino group which may have a substituent, a dialkylamino group which may have a substituent, an alkyl group which may have a substituent, an alkenyl group which may have a substituent, an alkynyl group which may have a substituent, an aryl group which may have a substituent, an alkoxy group which may have a substituent, an aryloxy group which may have a substituent, an alkylthio group which may have a substituent, an arylthio group which may have a substituent, a heterocyclic group which may have a substituent, or the like.

It may be possible for groups represented by $X_1$ to $X_4$ and $X_6$ to $X_{11}$ to provide a solubility of an electrochromic compound in a solvent whereby a process manufacturing an element may be facilitated. Furthermore, it may become possible to control a color development spectrum (color) finely. On the other hand, these groups may readily degrade a stability such as a heat resistance or a light resistance, and a hydrogen atom, a halogen, or a substituent with a carbon number of 6 or less is preferable. Moreover, a hydrogen atom or a substituent with a carbon number of 3 or less is particularly preferable.

For $X_5$, there is provided an aryl group which may have a substituent, a heterocyclic group which may have a substituent, an aryloxycarbonyl group which may have a substituent, an arylcarbonyl group which may have a substituent, an arylsulfonyl group which may have a substituent, or the like.

For a specific example of $R^1$, and $R^2$, there is provided an alkyl group which may have a substituent, an alkenyl group which may have a substituent, an alkynyl group which may have a substituent, an aryl group which may have a substituent, or the like. Furthermore, at least one of $R_1$ and $R_2$ may be a functional group capable of bonding to a hydroxyl group directly or indirectly. It may be only necessary for a functional group capable of bonding to a hydroxyl group directly or indirectly to be a functional group capable of bonding to a hydroxyl group directly or indirectly via hydrogen bonding, adsorption, chemical reaction, or the like, and its structure is not limited, wherein, for a preferable example, there is provided a phosphonate group, a phosphate group, a carboxyl group, a trichlorosilyl group, a trialkoxysilyl group, a monochlorosilyl group, a monoalkoxysilyl group, or the like.

For a trialkoxysilyl group, a triethoxysilyl group, a trimethoxysilyl group, or the like is preferable.

Among these, a trialkoxysilyl group or a phosphonate group which may provide a higher bonding force to an electrically conductive or semi-conductive nano-structure (as described below) is particularly preferable.

L represents an aromatic hydrocarbon group which may have a substituent and n represents an integer of 0 to 3. n is preferably 0 or 1.

Each of $A^-$ and $B^-$ independently represents a monovalent anion and is not particularly limited as long as it may be possible to provide a pair with a cationic part stably, and a Br ion, a Cl ion, a $ClO_4$ ion, a $PF_6$ ion, a $BF_4$ ion or the like is preferable. Furthermore, a Br ion, a Cl ion, or a $ClO_4$ ion is particularly preferable, wherein $A^-$ and $B^-$ are identical.

Additionally, it is desirable that an electrochromic compound according to the present invention has $X_1$ to $X_4$, $X_6$ to $X_{11}$, and $R^1$ and $R^2$ so as to provide a symmetric structure from the viewpoint of facility of synthesis thereof and improvement of stability thereof.

Specific chemical formulas (4-2) to (4-10) of an electrochromic compound according to the present invention will be described below and an electrochromic compound according to the present invention is not limited to these examples.

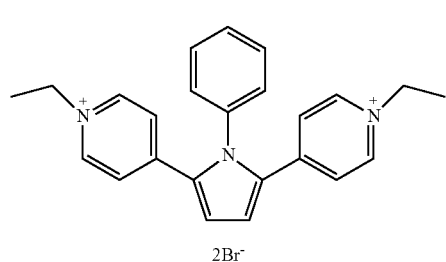

[4-2]

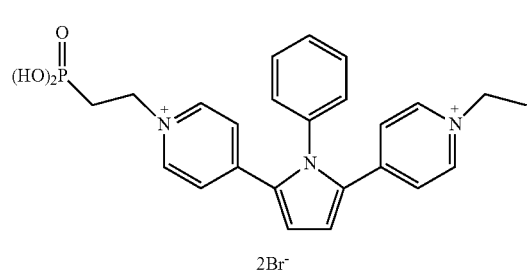

[4-3]

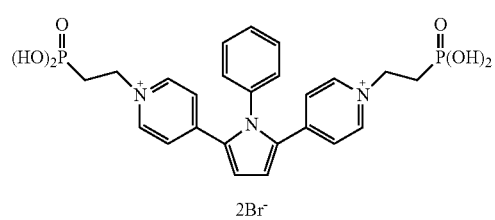

[4-4]

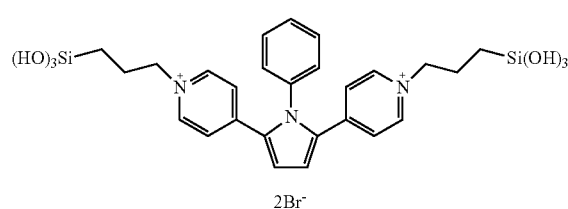

[4-5]

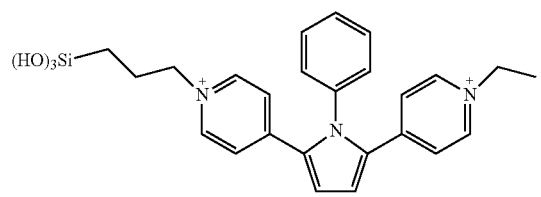

[4-6]

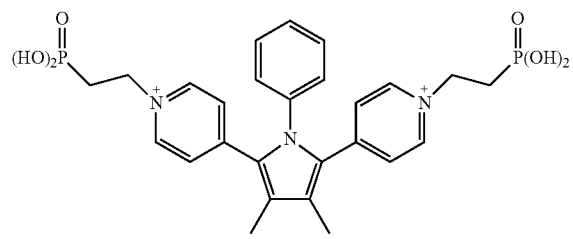

[4-7]

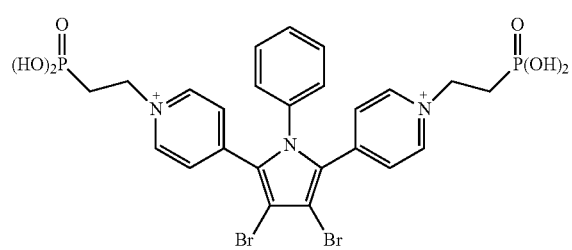

[4-8]

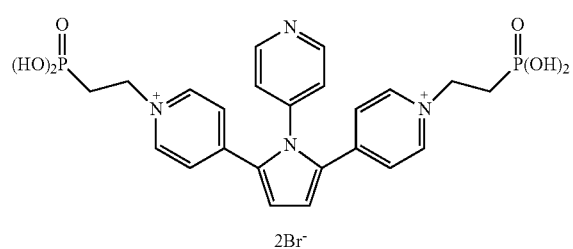

[4-9]

-continued

[4-10]

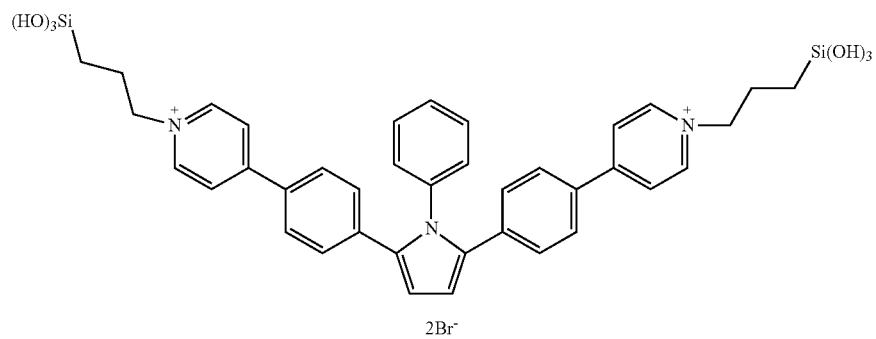

Furthermore, an electrochromic composition according to the present invention is characterized in that an electrochromic compound according to the present invention (an electrochromic compound represented by structural formulas [4-1]) is bonded or adsorbed to an electrically conductive or semi-conductive nano-structure. When an electrochromic composition according to the present invention is used for an electrochromic display element, it may be possible to provide magenta color development and further to be excellent in an image memory characteristic, that is, an image color development retention characteristic. Additionally, an electrically conductive or semi-conductive nano-structure is a body having a convex-concave structure on a nano-scale such as a nano-particle or a nano-porous structure.

When an electrochromic compound according to the present invention has a sulfonate group, a phosphate group, or a carboxyl group as an adsorption structure, it may be possible for the electrochromic compound to make a complex with a nano-structure readily whereby it may be possible to provide an electrochromic composition excellent in a color development or image retention characteristic. A plurality of sulfonate groups, phosphate groups, or carboxyl groups may be present in a compound.

Alternatively, when an electrochromic compound according to the present invention is bonded to a nano-structure via silanol bonding, such a bonding may be rigid and it may be possible to obtain a stable electrochromic composition similarly. A silanol bonding referred herein is a chemical bond between a silicon atom and an oxygen atom. Furthermore, it may be only necessary for an electrochromic composition to have a structure such that an electrochromic compound and a nano-structure are bonded via silanol bonding, and a manner or structure of such a bonding is not particularly limited.

For a material composing an electrically conductive or semi-conductive nano-structure, a metal oxide is preferable from the viewpoint of transparency or electrical conductivity thereof. For an example of such a metal oxide, a metal oxide is used which is based on titanium oxide, zinc oxide, tin oxide, aluminum oxide (referred to as alumina, below), zirconium oxide, cerium oxide, silicon oxide (referred to as silica, below), yttrium oxide, boron oxide, magnesium oxide, strontium titanate, potassium titanate, barium titanate, calcium titanate, calcium oxide, ferrite, hafnium oxide, tungsten oxide, iron oxide, copper oxide, nickel oxide, cobalt oxide, barium oxide, strontium oxide, vanadium oxide, aluminosilicate, calcium phosphate, or the like. Furthermore, these metal oxides may be used singly or two or more kinds thereof may be mixed and used. When one kind selected from titanium oxide, zinc oxide, tin oxide, alumina, zirconium oxide, iron oxide, magnesium oxide, indium oxide, and tungsten oxide, or a mixture thereof is used while an electrical property such as electrical conductivity or a physical property such as an optical property is taken into consideration, it may be possible to provide a multicolor display excellent in a response speed of color development/erasing. In particular, when titanium oxide is used, it may be possible to provide a multicolor display that is more excellent in a response speed of color development/erasing.

For a shape with respect to such a metal oxide, a metal oxide fine particle with an average primary particle diameter of 30 nm or less is preferable. The smaller a particle diameter is, the more a transmittance of light through a metal oxide is improved, so that it may be possible to provide a shape with a larger surface area per unit volume (referred to as "specific surface area" below). When a larger specific surface area is held, it may be possible to carry an electrochromic compound more efficiently and it may be possible to provide a multicolor display excellent in a display contrast at color development/erasing. A specific surface area of a nano-structure is not particularly limited, and may be, for example, 100 $m^2/g$ or more.

<Display Element>

Next, a display element according to the present invention will be described.

Figure 18A:
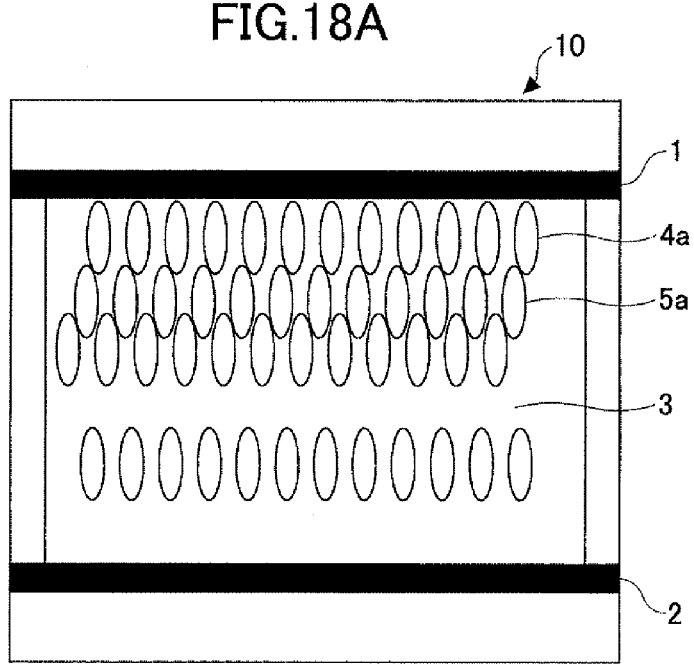
Figure 18B:
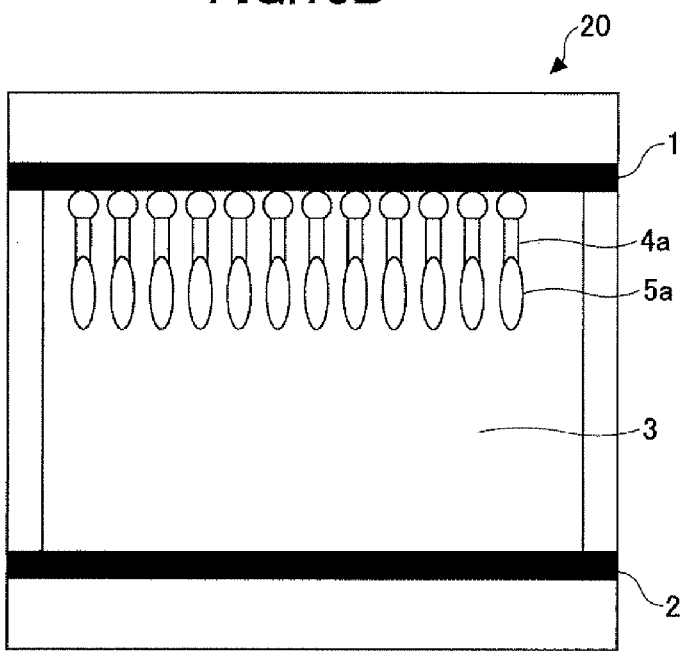

FIGS. 18A and 18B illustrate examples of the structure of a general display element using an electrochromic compound according to the present invention. As illustrated in FIG. 18A and FIG. 18B, each of display elements 10 and 20 according to the present invention includes a display electrode 1, an opposing electrode 2 provided to oppose and separated from the display electrode 1 at a space, and an electrolyte 3 arranged between both electrodes 1 and 2 (display electrode 1 and opposing electrode 2), and has a display layer 4a containing at least an electrochromic compound 5a according to the present invention on a surface of the display electrode 1 at a side of the opposing electrode 2 (a side of an opposing face of the opposing electrode 2).

Figure 19:
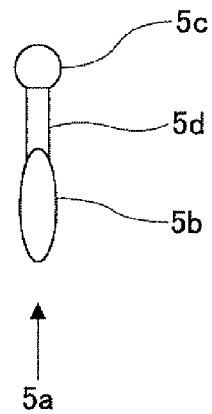
FIG. 19 is a schematic diagram illustrating a configuration of an electrochromic compound having an adsorption group.

In a display element in FIG. 18B, a display layer 4a is formed on a surface of a display electrode 1 at a side of an opposing electrode 2 by using an electrochromic compound 5a according to the present invention. For a method of manufacturing it, any method such as a dipping method, a vapor deposition method, a spin-coating method, a printing method, or an ink jet method may be used. As illustrated in FIG. 19, when an electrochromic compound 5a according to the present invention has an adsorption group (bonding group) 5c in a molecule structure thereof, the adsorption group 5c adsorbs to a display electrode 1 whereby a display layer 4a is formed. Herein, an oxidation-reduction color development part 5b that provides color development is linked with an adsorption group 5c through a spacer part 5d as illustrated in FIG. 19, and they constitute an electrochromic compound 5a.

Furthermore, as illustrated in FIG. 18A, it may be possible to provide a solution in which an electrolyte is dissolved in a solvent and further it may also be possible to dissolve an electrochromic compound 5a in such a solution. In this case, an electrochromic compound 5a provides color development/erasing only on an electrode surface due to an oxidation-reduction reaction thereof. That is, a surface of a solution containing an electrochromic compound at a side of a surface of a display electrode 1 which opposes an opposing electrode 2 functions as a display layer 4a.

Figure 20:
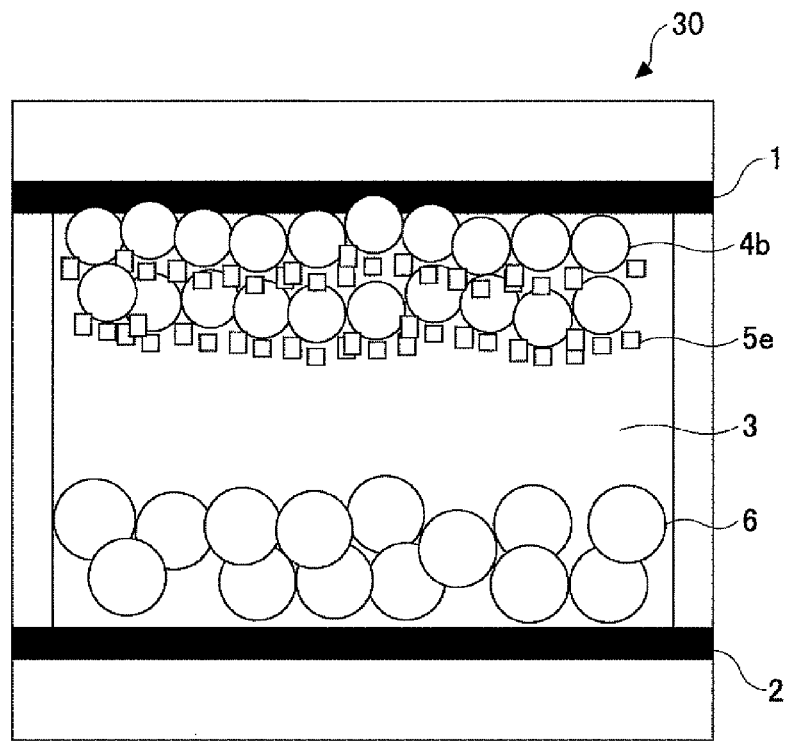
FIG. 20 is a schematic diagram illustrating an example of a configuration of a general display element using an electrochromic composition according to the present invention.

Moreover, FIG. 20 illustrates an example of the structure of a general display element using an electrochromic composition 5e according to the present invention. As illustrated in FIG. 20, a display element 30 according to the present invention includes a display electrode 1, an opposing electrode 2 provided to oppose and separate from the display electrode 1, and an electrolyte arranged between both electrodes 1 and 2 (the display electrode 1 and the opposing electrode 2), wherein a display layer 4b that contains at least an electrochromic composition 5e according to the present invention is provided on a surface of the display electrode 1 at a side of the opposing electrode 2 (a side of a surface opposing the opposing electrode 2). Furthermore, a white color reflective layer 6 composed of white color particles is provided on an opposing electrode 2 at a side of a display electrode 1 (a side of a surface opposing a display electrode 1).

In a display element illustrated in FIG. 20, a display layer 4b is formed on a surface of a display electrode 1 at a side of an opposing electrode 2 by using an electrochromic composition 5e according to the present invention. For a method for manufacturing it, any method such as a dipping method, a vapor deposition method, a spin-coating method, a printing method, or an ink jet method may be used. As illustrated in FIG. 19, an electrochromic compound 5a in an electrochromic composition 5e according to the present invention has a bonding group 5c in the molecular structure thereof and the bonding group 5c is bonded to an electrically conductive or semi-conductive nano-structure, thereby constituting the electrochromic composition 5e. Furthermore, a layered electrochromic composition 5e is provided on a display electrode 1 to form a display layer 4b.

Next, a material(s) used for an electrochromic display element 10, 20, or 30 according to an embodiment of the present invention will be described.

For a display electrode 1, it is desirable to use a transparent and electrically conductive substrate. For a transparent and electrically conductive substrate, it is desirable to provide a glass or plastic file coated with a transparent and electrically conductive thin film. When a plastic film is used, it may be possible to manufacture a lightweight and flexible display element.

A material for a transparent and electrically conductive thin film is not particularly limited as long as such a material has an electrical conductivity, and a transparent and electrically conductive material that is transparent and excellent in an electrical conductivity is used in order to ensure a certain light transparency. Thereby, it may be possible to improve a visibility of a developed color. For a transparent and electrically conductive material, it may be possible to use an inorganic material such as an indium oxide doped with tin (referred to an ITO, below), a tin oxide doped with fluorine (referred to as an FTO, below), or a tin oxide doped with antimony (referred to as an ATO, below), and in particular, an inorganic material is preferable which includes any one of an indium oxide (referred to as an In oxide, below), a tin oxide (referred to as an Sn oxide, below), or a zinc oxide (referred to as a Zn oxide, below). An In oxide, an Sn oxide, or a Zn oxide is a material capable of readily forming a film by a sputtering method and a material capable of obtaining a good transparency and electric conductivity. Furthermore, InSnO, GaZnO, SnO, $In_2O_3$, and ZnO are particularly preferable materials.

For an opposing electrode 2, a transparent and electrically conductive film of an ITO, FTO, zinc oxide or the like, an electrically conductive and metallic film of zinc, platinum or the like, a carbon, or the like is used. Generally, an opposing electrode 2 is also formed on a substrate. For a substrate for an opposing electrode, a glass or a plastic film is also desirable.

When a metal plate of zinc or the like is used for an opposing electrode 2, the opposing electrode 2 doubles as a substrate.

Furthermore, when a material of an opposing electrode 2 includes a material causing a reverse reaction of an oxidation-reduction reaction caused by an electrochromic composition in a display layer 4, it may be possible to provide a stable color development/erasing. That is, when a material that causes a reduction reaction when an electrochromic composition provides color development due to oxidation and an oxidation reaction when an electrochromic composition provides color development due to reduction is used for an opposing electrode 2, a color development/erasing reaction in a display layer 4 containing an electrochromic composition may be more stabilized.

For an electrolyte 3, a supporting electrolyte dissolved in a solvent is used generally.

For a supporting electrolyte, it may be possible to use, for example, an inorganic ion salt such as an alkali metal salt or an alkaline earth metal salt, an ammonium salt, or a supporting electrolyte of an acid or alkali. Specifically, it may be possible to use $LiClO_4$, $LiBF_4$, $LiAsF_6$, $LiPF_6$, $CF_3SO_3Li$, $CF_3COOLi$, $KCl$, $NaClO_3$, $NaCl$, $NaBF_4$, $NaSCN$, $KBF_4$, $Mg(ClO_4)_2$, $Mg(BF_4)_2$, or the like.

Furthermore, for example, propylene carbonate, acetonitrile, γ-butyrolactone, ethylene carbonate, sulfolane, dioxolane, tetrahydrofuran, 2-methyltetrahydrofuran, dimethyl sulfoxide, 1,2-dimethoxyethane, 1,2-ethoxymethoxyethane, polyethylene glycol, an alcohol, or the like is used for a solvent.

In addition, no limitation to a liquid electrolyte in which a supporting electrolyte is dissolved in a solvent is provided, and hence, a gel electrolyte or a solid electrolyte such as a polymer electrolyte is also used. For example, there is provided a solid-type one such as a perfluorosulfonate-type polymer film. A solution-type one has an advantage of having a high ionic conductance and a solid type-one is suitable for manufacturing an element having a less degradation and a higher durability.

Furthermore, when a display element according to the present invention is used as a reflective display element, it is desirable to provide a white color reflective layer 6 between a display electrode 1 and an opposing electrode 2 as illustrated in FIG. 20. One simple method for manufacturing a white color reflective layer 6 is to disperse white color pigment fine particles in a resin and apply them onto an opposing electrode 2. For a white color pigment fine particle, it may be possible to provide a particle made of a general metal oxide, and specifically, there is provided titanium oxide, aluminum oxide, zinc oxide, silicon oxide, cesium oxide, yttrium oxide, or the like. Moreover, it may be possible to mix white color pigment particles into a polymer electrolyte so as to double as a white color reflective layer.

For a method for driving a display element 10, 20, or 30, any method may be used as long as it is possible to apply a desired voltage or electric current. When a passive driving method is used, it may be possible to manufacture an inexpensive display element. Furthermore, when an active driving method is used, it may be possible to provide a highly fine and high speed display. When an active driving element is provided on an apposing substrate, it may be possible to provide active driving more easily.

An electrochromic compound, an electrochromic composition, and a display element using the same will be described in practical examples below.

Practical Example 1-1

Synthesis of Electrochromic Compound (1-2)

Figure 4:
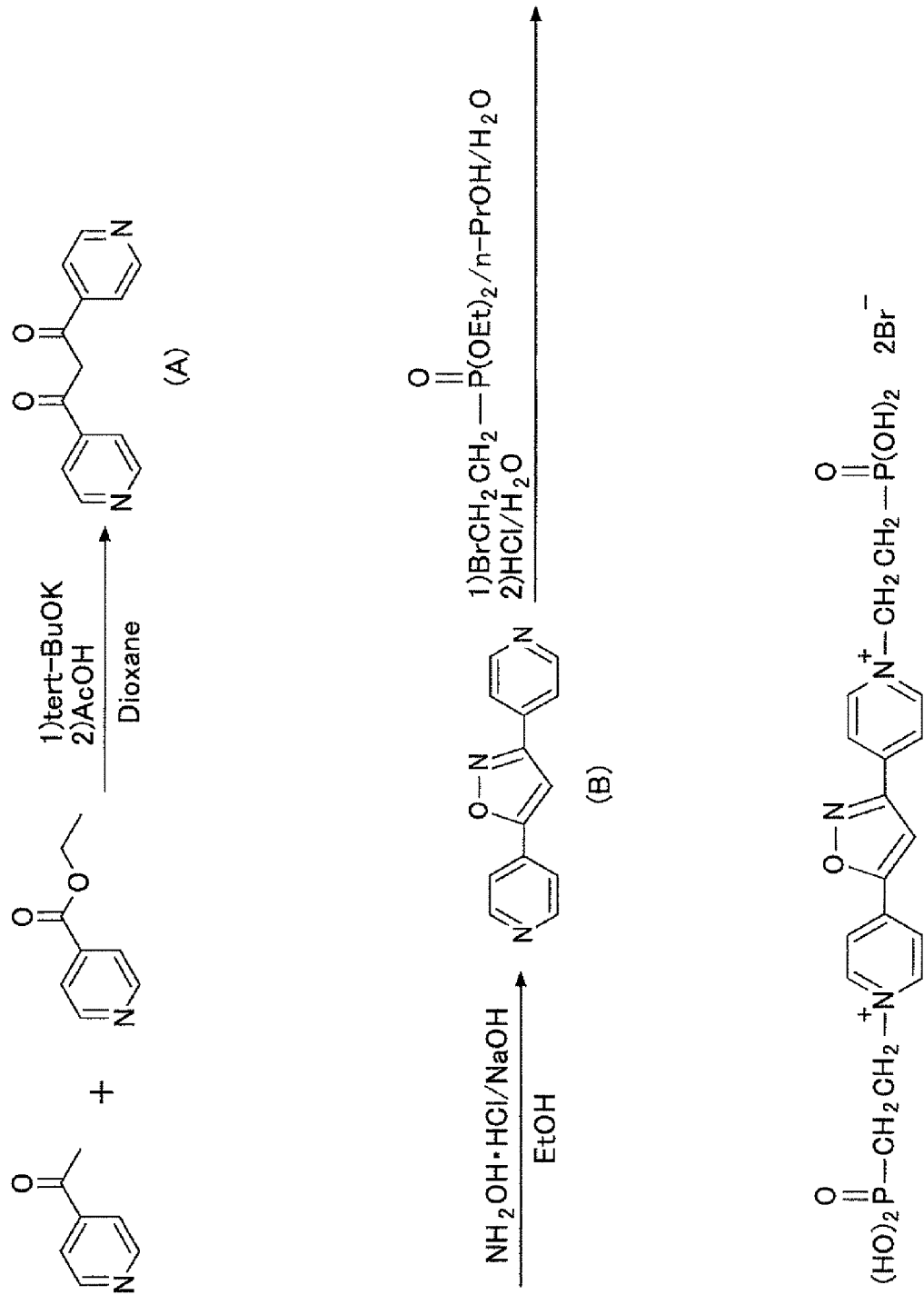
FIG. 4 is a diagram illustrating a flow of synthesis of electrochromic compound (1-2).

FIG. 4 illustrates a flow of synthesis of electrochromic compound (1-2).

After 5.6 g of 4-acetylpyridine, 7.0 g of ethyl isonicotinate, and 30 ml of 1,4-dioxane were charged into a reaction flask and 5.2 g of potassium tert-butoxide was gently added thereto, agitation at 90° C. for 1 hour and standing to cool were conducted. After a reaction liquid was diluted with 80 ml of water, 7 ml of acetic acid was added to precipitate a product. After the precipitated product was filtered, washing with water and drying were conducted to obtain 2.7 g of compound (1-A).

3.36 g of hydroxylamine hydrochloride, 1.93 g of sodium hydroxide, and 32 ml of ethanol were charged into a reaction flask and agitation was conducted at 40° C. for 10 minutes. Then, after 2.7 g of compound (1-A) was thrown thereto and agitation under reflux was conducted for 1 hour, 2.1 g of sodium hydroxide was added thereto and agitation under reflux for 1 hour and standing to cool were conducted. After ethanol was distilled out from the reaction liquid, impurities in a residue were dissolved in water. Furthermore, after filtration, washing with water and drying were conducted to obtain 1.1 g of compound (1-B). GC/MS measurement of compound (1-B) was conducted, and as a result, the mass-to-charge ratio of a molecular ion peal was 223.

After 0.45 g of compound (1-B), 2.0 g of diethyl 2-bromoethylphosphonate, 3 ml of 1-propanol, and 6 ml of water were charged into a reaction flask and agitation was conducted at 90° C. for 40 hours, standing to cool was conducted. A reaction liquid was discharged into a mixed liquid of 15 ml of water and 30 ml of ethyl acetate, and an aqueous layer was fractionated. After the obtained aqueous layer and 20 ml of concentrated hydrochloric acid were charged into a reaction flask and agitation was conducted at 90° C. for 23 hours, standing to cool was conducted. After water was distilled out from a reaction liquid and a tar-like residue was dissolved in methanol, dropping into a 2-propanol/ethanol mixed solvent (volume ratio 2/1) under agitation was conducted to crystallize a product. Furthermore, after filtration, washing with 2-propanol and drying were conducted to obtain 0.30 g of electrochromic compound (1-2). $^1$H-NMR (300 MHz, D$_2$O) measurement of electrochromic compound (1-2) was conducted, signals for supporting the structure of electrochromic compound (1-2), δ 2.23 (m, 4H), δ 4.76 (m, 4H), δ 7.99 (s, 1H), δ 8.43 (m, 4H), and δ 8.96 (dd, 4H), were obtained.

[Manufacturing of a Display Element]

A display electrode 11a having a thickness of about 100 nm and made of ITO was formed on a 16 mm×23 mm area of the top surface of a 30 mm×30 mm glass substrate 11b by using a sputter method to obtain a display substrate 11. The resistance of a display electrode 11a between end portions thereof was measured, and as a result, was about 200 Ω.

Then, a dispersion liquid SP210 (produced by Showa Titanium Corporation) of titanium oxide nano-particles was applied onto the display electrode 11a by using a spin-coat method and annealing was conducted at 120° C. for 15 minutes to form a nano-particle accumulation. Furthermore, a 1 mass % solution of electrochromic compound (1-2) in 2,2,3,3-tetrafluoropropanol was applied thereto by using a spin-coat method and annealing was conducted at 120° C. for 10 minutes whereby electrochromic compound (1-2) was adsorbed onto a surface of the nano-particle accumulation to form a display layer 33 containing an electrochromic composition 33b.

Meanwhile, an ITO film with a thickness of about 150 nm was formed on the entire of the top surface of a 30 mm×30 mm glass substrate 12b by using a sputter method. Then, after a liquid in which 25 mass % of 2-ethoxyethyl acetate was added into a thermosetting electrically conductive carbon ink CH$_{10}$ (produced by Jujo Chemical Corporation) was applied onto the ITO film by using a spin-coat method, annealing was conducted at 120° C. for 15 minutes whereby an opposing electrode 12a was formed and an apposing substrate 12 was obtained.

The display substrate 11 and the opposing substrate 12 were bonded via a 75 μm spacer 15 to obtain a cell. Then, a liquid in which 35 mass % of titanium oxide particles with an average primary particle diameter of 300 nm (produced by Ishihara Sangyo Kaisha, Ltd.) were dispersed in an electrolyte liquid 13a in which 20 mass % of tetrabutylammonium perchlorate was dissolved in dimethyl sulfoxide (DMSO) was enclosed in the cell whereby a white color reflective layer 14 was formed and a display element 30 was obtained.

[Color Development/Erasing Test]

When a negative electrode and a positive electrode were connected to the display electrode 11a and opposing electrode 12a of the display element 30, respectively, and a voltage of 3.0V was applied for 1 second, cyan color development was provided. Then, when a voltage of −4.5 V was applied for 2 seconds, complete color erasing was provided and white color was recovered. Furthermore, even though a voltage of 3.0 V was applied for 1 second and subsequently leaving for 300 seconds was conducted without applying a voltage, a color development state of the display element 30 was retained, whereby it was confirmed that an excellent image retention characteristic was provided.

Figure 5:
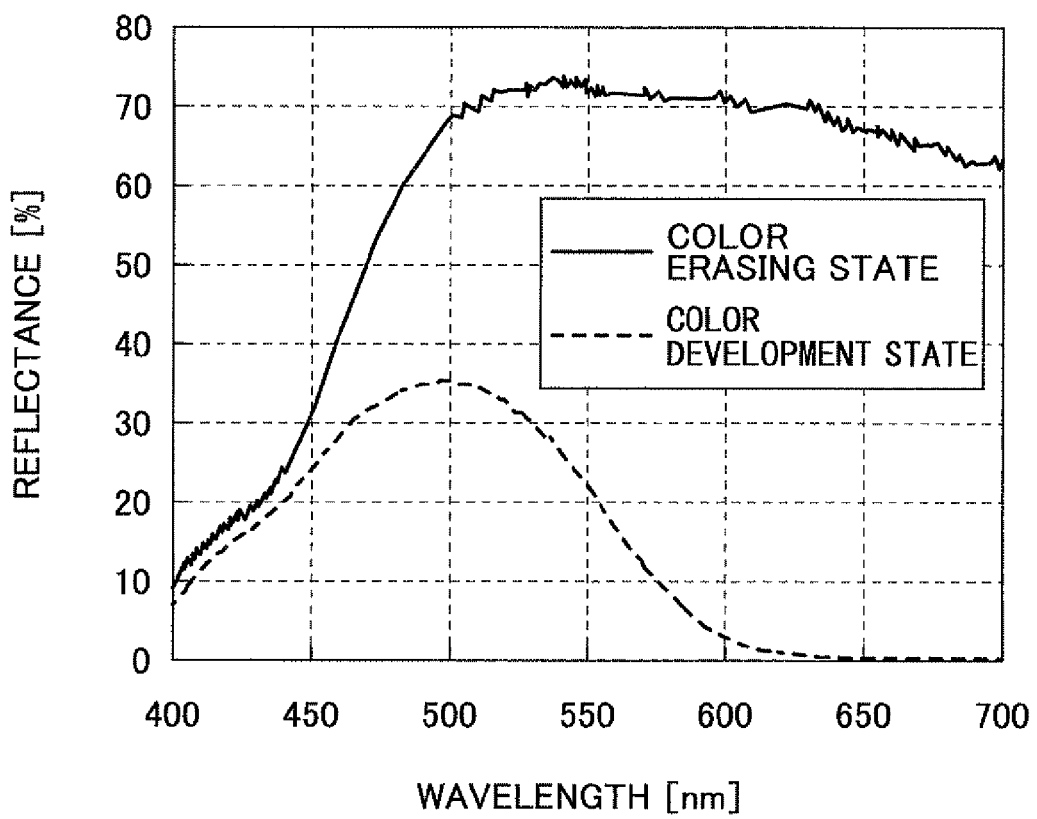
FIG. 5 is a diagram illustrating a reflection spectrum of a display element in practical example 1-1.
Figure 6:
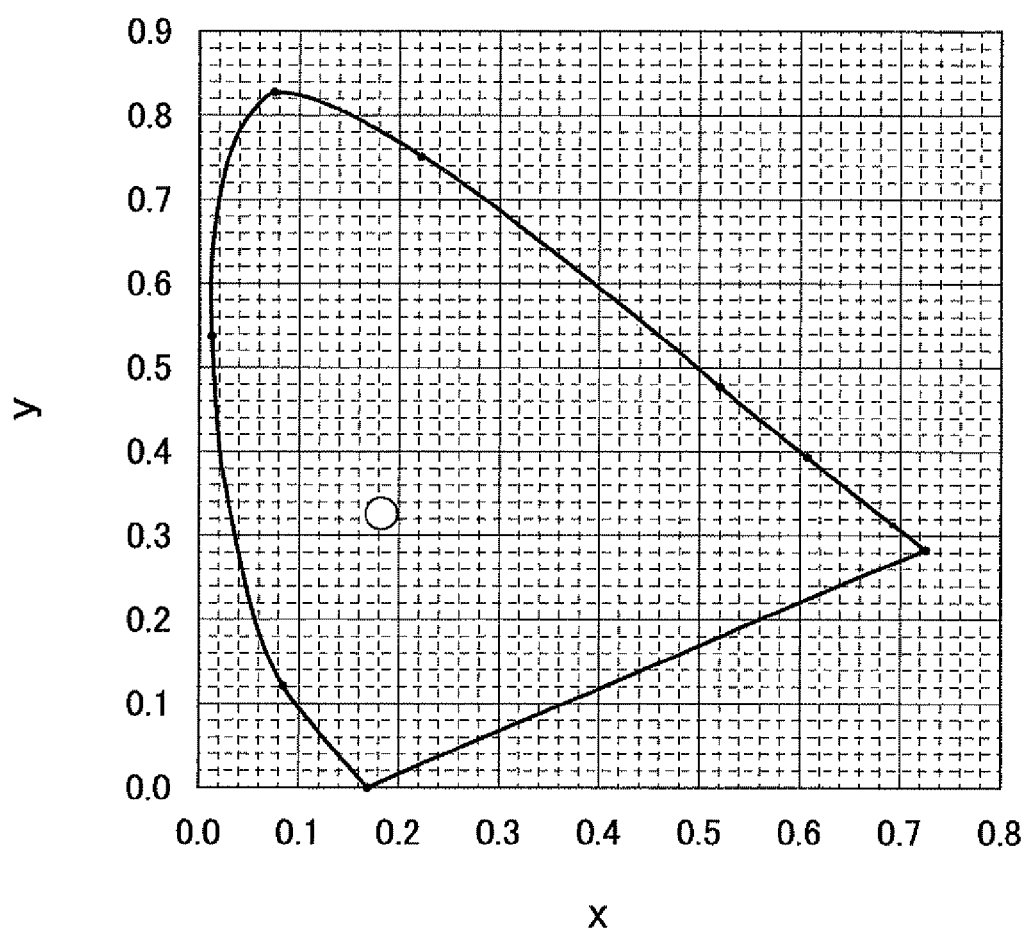
FIG. 6 is a diagram illustrating a result of coordinate transformation of a reflection spectrum at a color development state in FIG. 5 into a CIE color specification system.

When the display element 30 at a color development state or a color erasing state was irradiated with diffused light by using a spectrophotometric colorimeter LCD-5000 (produced by Otsuka Electronics Co., Ltd.), a reflection spectrum illustrated in FIG. 5 was obtained. Furthermore, FIG. 6 illustrates a result of a coordination transformation of a reflection spectrum at a color development state in FIG. 5 into a CIE color specification system. From FIG. 5 and FIG. 6, it was confirmed that the width of a low reflectance region of the display electrode 30 in the visible region was narrow and a cyan color development was provided.

[Measurement of Light Absorption Spectrum]

The display substrate 11 on which the display layer 33 was formed was put in a quartz cell, and the quart cell was filled with an electrolyte liquid in which 20 mass % of tetrabutylammonium perchlorate was dissolved in dimethyl sulfoxide (DMSO), while a platinum electrode as a counter electrode and a Ag/Ag$^+$ electrode RE-7 (produced by BAS Corporation) as a reference electrode were used. When a voltage of −1.5 V was applied by using a potentiostat ALS-660C (produced by BAS Corporation), cyan color development was provided.

Figure 7:
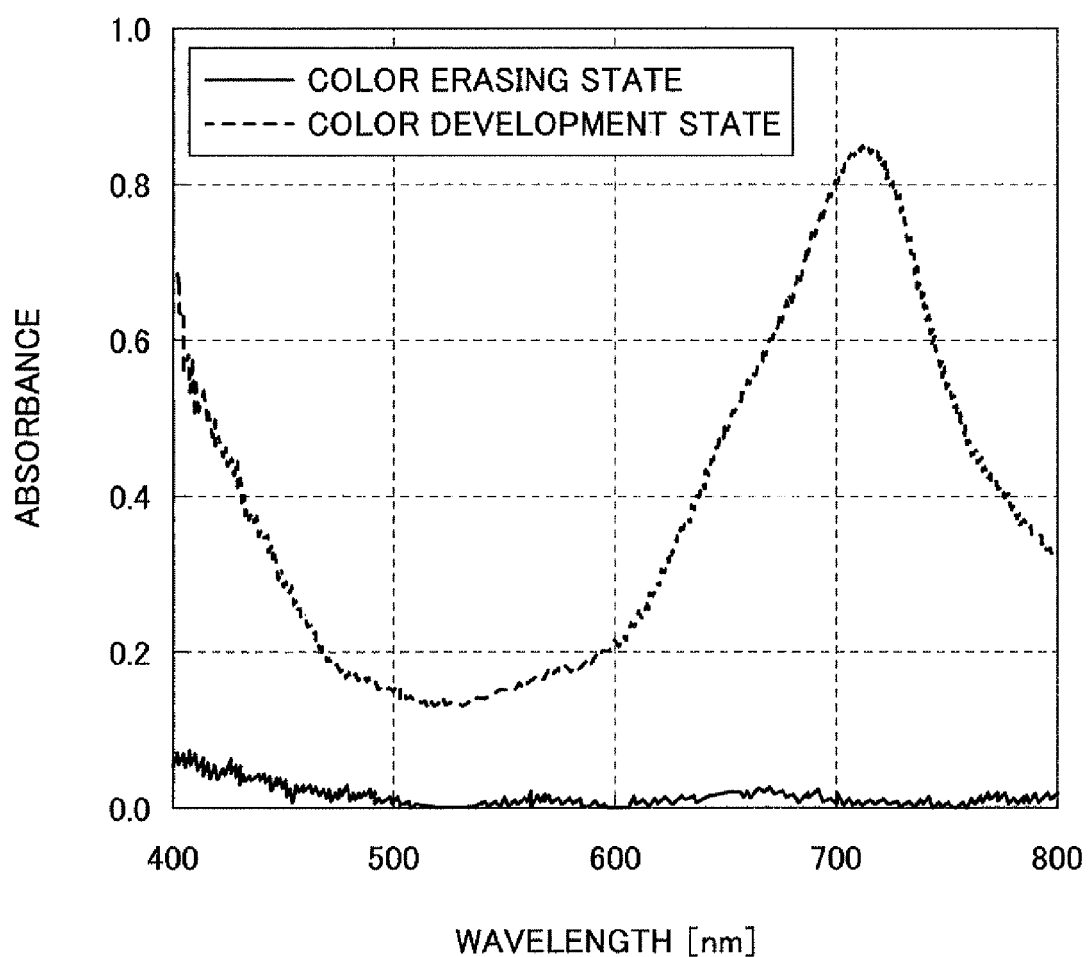
FIG. 7 is a diagram illustrating a light absorption spectrum of a display substrate on which a display layer in practical example 1-1 is formed.

When the quartz cell was irradiated with light by using a deuterium tungsten halogen light source DH-2000 (produced by Ocean Optics Inc.) and transmitted light was detected by a spectrometer USB4000 (produced by Ocean Optics Inc.), a light absorption spectrum illustrated in FIG. 7 was obtained.

From FIG. 7, it was confirmed that the display later 33 at a color development state had a sharp absorption peak near 720 nm.

Practical Example 1-2

Synthesis of Electrochromic Compound (1-10)

After 0.45 g of compound (1-B), a suitable amount of ethyl bromide, 3 ml of 1-propanol, and 6 ml of water were charged in a reaction flask and agitation was conducted at 90° C. for 40 hours, standing to cool was conducted. A reaction liquid was discharged into a mixed liquid of 15 ml of water and 30 ml of ethyl acetate, and an aqueous layer was fractionated. After the obtained aqueous layer and 20 ml of concentrated hydrochloric acid were charged in a reaction flask and agitation was conducted at 90° C. for 23 hours, standing to cool was conducted. After water was distilled out from the reaction liquid and a tar-like residue was dissolved in methanol, dropping into a mixed solvent of 2-propanol/ethanol (volume ratio 2/1) was conducted under agitation was conducted to crystallize a product. Furthermore, after filtration, washing with 2-propanol and drying were conducted to obtain 0.30 g of electrochromic compound (1-10).

[Manufacturing of Display Element]

As a display substrate 11 and an opposing substrate 12, 30 mm×30 mm glass substrates 11b and 12b (produced by AGC Fabritech Co., Ltd.) were used wherein a display electrode 11a and an opposing electrode 12a made of $SnO_2$ were formed on the entire of the top surfaces thereof, respectively. The resistance of the display electrode 11a between end portions thereof was measured and was about 20 Ω.

The display substrate 11 and the opposing substrate 12 were bonded via a 75 μm spacer to obtain a cell. Then, an electrolyte liquid 13a in which 50 mass % of a 1 mass % solution of electrochromic compound (1-10) 13b in a mixed solvent of water/2,2,3,3-tetrafluoropropanol (mass ratio 1/9) was added into a liquid in which 20 mass % of tetrabutylammonium perchlorate was dissolved in dimethyl sulfoxide (DMSO) was enclosed in the cell to obtain a display element 10 having a configuration such that a white reflective layer 14 was not formed.

[Color Development/Erasing Test]

When a negative electrode and a positive electrode were connected to the display electrode 11a and opposing electrode 12a of the display element 10, respectively, and a voltage of 3.0 V was applied for 2 seconds, cyan color development was provided. Then, when a voltage of −3.0 V was applied for 4 seconds, complete color erasing was provided and a colorless and transparent state was recovered. Furthermore, even though a voltage 3.0 V was applied for 2 seconds and subsequently leaving for 300 seconds was conducted without applying a voltage, a color development state of the display element 10 was retained, whereby it was confirmed that an excellent image retention characteristic was provided.

Practical Example 1-3

Synthesis of Electrochromic Compound (1-11)

Electrochromic compound (1-11) was obtained similarly to electrochromic compound (1-2) except that diethyl 4-(bromomethyl)benzylphosphonate was used instead of diethyl 2-bromoethylphosphonate.

[Manufacturing of Display Element]

A display element 30 was obtained similarly to practical example 1-1 except that a 1.5 mass % solution of electrochromic compound (1-11) in 2,2,3,3-tetrafluoropropanol was used instead of a 1 mass % solution of electrochromic compound (1-2) in 2,2,3,3-tetrafluoropropanol.

[Color Development/Erasing Test]

When a negative electrode and a positive electrode were connected to a display electrode 11a and opposing electrode 12a of the display element 30, respectively, and a voltage of 3.0 V was applied for 0.5 seconds, cyan color development was provided. Then, when a voltage of −4.5 V was applied for 2 seconds, complete color erasing was provided and a white color was recovered. Furthermore, even though a voltage of 3.0 V was applied for 0.5 seconds and subsequently leaving for 300 seconds was conducted without applying a voltage, a color development state of the display element 30 was retained, whereby it was confirmed that an excellent image retention characteristic was provided.

Practical Example 1-4

Manufacturing of Display Element

As a display substrate, a 30 mm×30 mm glass substrate 11b (produced by AGC Fabritech Co., Ltd.) was used in which a display electrode 11a made of $SnO_2$ was formed on the entire of the top surface thereof.

Then, a dispersion liquid of titanium oxide nano-particles SP210 (produced by Showa Titanium Corporation) was applied onto the display electrode 11a by using a spin-coat method and annealing was conducted at 120° C. for 15 minutes to form a nano-particle accumulation. A display substrate 11 on which the nano-particle accumulation was formed was dipped in a 0.02 mass % solution of 3-bromopropyltrichlorosilane in toluene for 30 minutes to subject the nano-particle accumulation to surface treatment. Furthermore, the display substrate 11 on which the nano-particle accumulation subjected to surface treatment was formed was dipped in a 0.1 mass % solution of compound (1-B) in toluene and reflux was conducted for 2 hours, whereby the nano-particle accumulation was subjected to surface treatment to form a display layer 33 containing an electrochromic composition 33b.

Meanwhile, an ITO film with a thickness of about 150 nm was formed on the entire of the top surface of a 30 mm×30 mm glass substrate 12b by using a sputter method. Then, after a liquid in which 25 mass % of 2-ethoxyethyl acetate was added into a thermosetting electrically conductive carbon ink CH10 (produced by Jujo Chemical Corporation) was applied onto the ITO film by using a spin-coat method, annealing was conducted at 120° C. for 15 minutes whereby an opposing electrode 12a was formed and an apposing substrate 12 was obtained.

The display substrate 11 and the opposing substrate 12 were bonded via a 75 μm spacer 15 to obtain a cell. Then, a liquid in which 35 mass % of titanium oxide particles with an average primary particle diameter of 300 nm (produced by Ishihara Sangyo Kaisha, Ltd.) were dispersed in an electrolyte liquid 13a in which 20 mass % of tetrabutylammonium perchlorate was dissolved in dimethyl sulfoxide (DMSO) was enclosed in the cell whereby a white color reflective layer 14 was formed and a display element 30 was obtained.

[Color Development/Erasing Test]

When a negative electrode and a positive electrode were connected to a display electrode 11a and opposing electrode 12a of the display element 10, respectively, and a voltage of 3.0 V was applied for 1 second, cyan color development was provided. Then, when a voltage of −4.5 V was applied for 2 seconds, complete color erasing was provided and a colorless and transparent state was recovered. Furthermore, even though a voltage of 3.0 V was applied for 1 second and subsequently leaving for 300 seconds was conducted without applying a voltage, a color development state of the display element 10 was retained, whereby it was confirmed that an excellent image retention characteristic was provided.

Comparative Example 1-1

Manufacturing of Display Element

A display element 30 was obtained similarly to practical example 1-1 except that a viologen compound represented by a chemical formula of

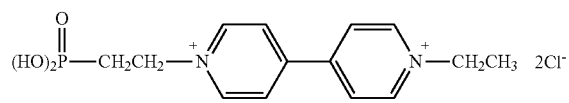

was used instead of electrochromic compound (1-2).

[Color Development/Erasing Test]

When a negative electrode and a positive electrode were connected to a display electrode 11a and opposing electrode 12a of the display element 30, respectively, and a voltage of 3.0 V was applied for 1 second, blue color development was provided. Then, when a voltage of −4.5 V was applied for 2 seconds, complete color erasing was provided and a white color was recovered. Furthermore, even though a voltage of 3.0 V was applied for 1 second and subsequently leaving for 300 seconds was conducted without applying a voltage, a color development state of the display element 30 was retained, whereby it was confirmed that an excellent image retention characteristic was provided.

Figure 8:
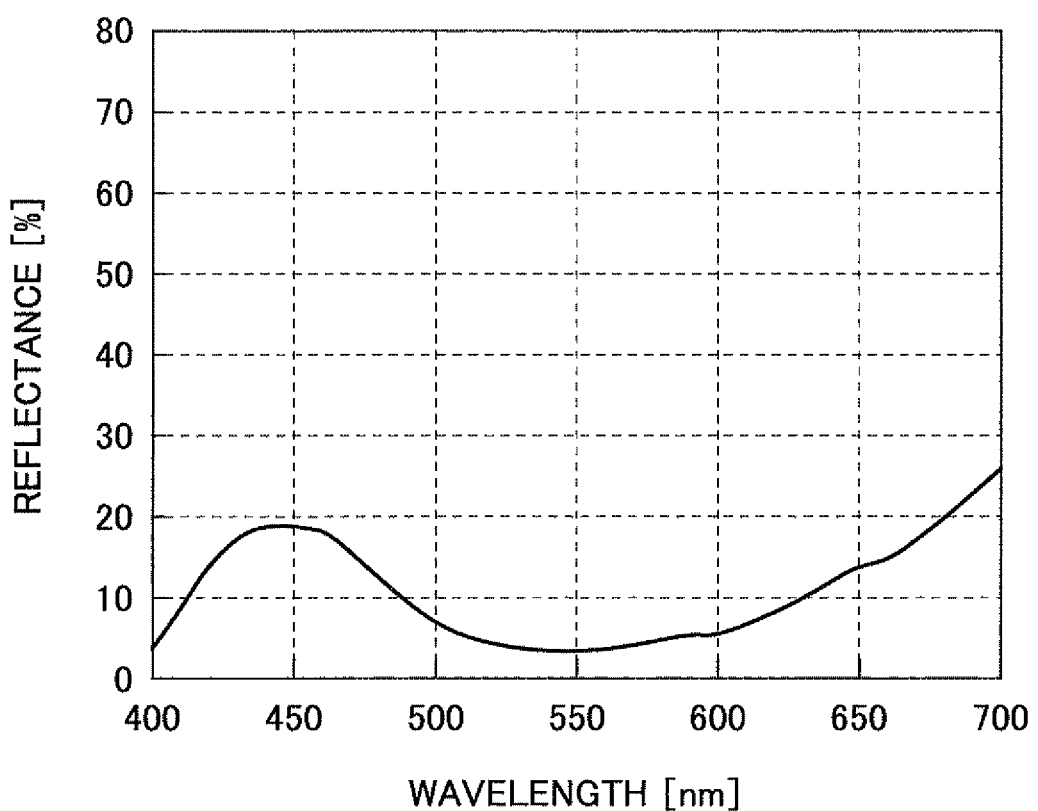
FIG. 8 is a diagram illustrating a reflection spectrum of a display element in comparative example 1-1.

When the display element 30 at a color development state was irradiated with diffused light by using a spectrophotometric colorimeter LCD-5000 (produced by Otsuka Electronics Co., Ltd.), a reflection spectrum illustrated in FIG. 8 was obtained. From FIG. 8, it was confirmed that the width of a low reflectance region of the display electrode 30 in the visible region was broad and a broad light absorption was provided whereby a cyan color development was provided.

Practical Example 2-1

Synthesis of Compound (2-B)

Figure 9:
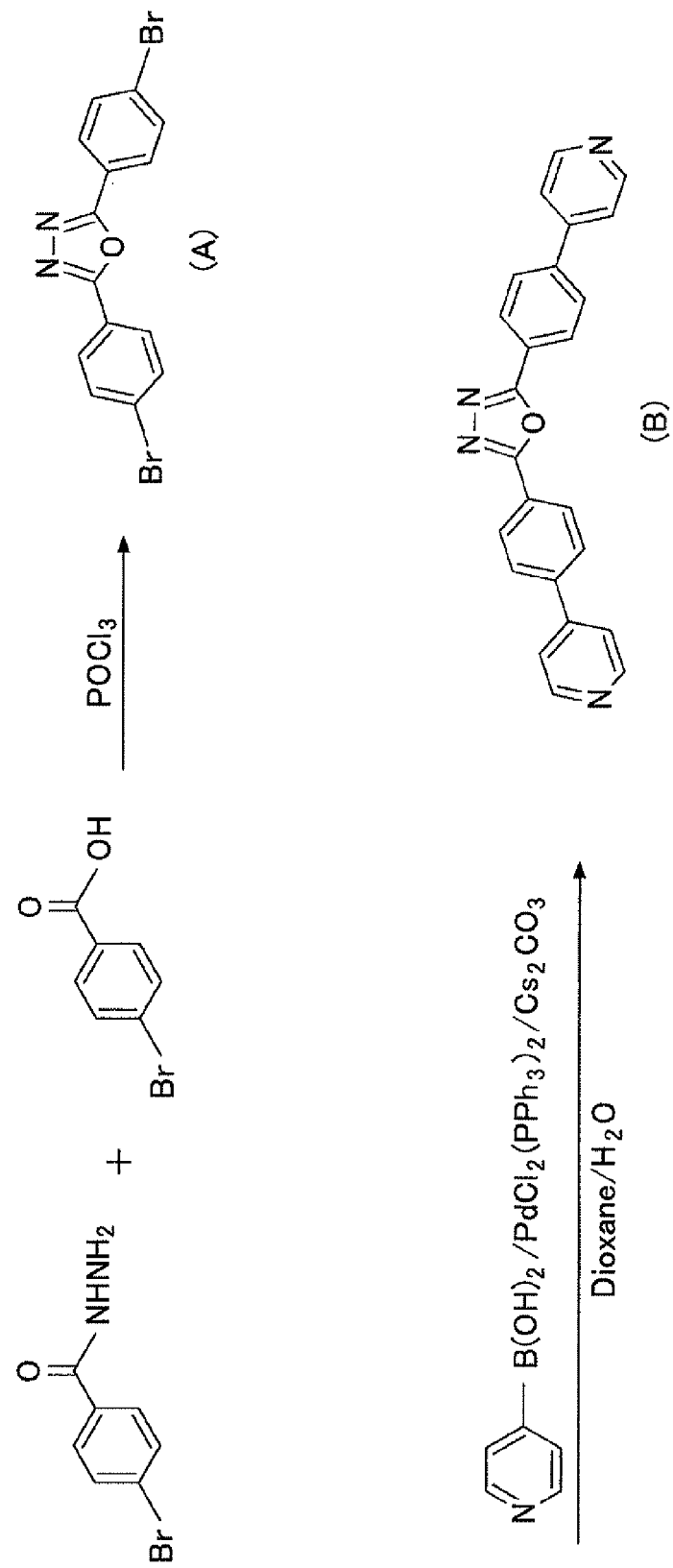
FIG. 9 is a diagram illustrating a flow of synthesis of compound (2-B).

FIG. 9 illustrates a flow of synthesis of compound (2-B).

After 5.7 g of 4-bromobenzoic hydrazide, 10.0 g of 4-bromobenzoic acid, and 13 ml of phosphorus oxychloride were charged into a reaction flask and agitation was conducted at 110° C. for 3 hours, standing to cool was conducted. After a reaction liquid was gently discharged into ice-water neutralization with a diluted solution of sodium hydroxide was conducted to precipitate a product. After the precipitated product was filtered, sequential washing with water and methanol and drying were conducted to obtain 8.3 g of compound (2-A).

After 4.6 g of compound (2-A), 3.1 g of 4-pyridineboronic acid, 0.84 g of dichlorobis(triphenylphosphine)palladium (II), 11.7 g of cesium carbonate, 24 ml of water, and 60 ml of 1,4-dioxane were charged into a reaction flask substituted with nitrogen and agitation was conducted at 90° C. for 12 hours, standing to cool was conducted. After a reaction liquid was diluted with chloroform, filtration was conducted. After a filtrate was washed with water, drying with anhydrous sodium sulfate was conducted and chloroform was distilled out. An obtained solid was purified by silica gel column chromatography using a mixed solvent of chloroform/ethanol (volume ratio 20/1) as an eluent to obtain 2.8 g of compound (2-B). When LC/MS measurement of compound (2-B) was conducted, the mass-to-charge ratio of a molecular ion peak was 450.

[Manufacturing of a Display Element]

As a display substrate 11, a 30 mm×30 mm glass substrate 11b (produced by AGC Fabritech Co., Ltd.) was used in which a display electrode 11a made of $SnO_2$ was formed on the entire of the top surface thereof. The resistance of the display electrode 11a between end portions thereof was measured and was about 20 Ω.

Then, a dispersion liquid of titanium oxide nano-particles SP210 (produced by Showa Titanium Corporation) was applied onto the display electrode 11a by using a spin-coat method and annealing was conducted at 120° C. for 15 minutes to form a nano-particle accumulation. A display substrate 11 on which the nano-particle accumulation was formed was dipped in a 0.02 mass % solution of 3-bromopropyltrichlorosilane in toluene for 30 minutes to subject the nano-particle accumulation to surface treatment. Furthermore, the display substrate 11 on which the nano-particle accumulation subjected to surface treatment was formed was dipped in a 0.1 mass % solution of compound (2-B) in toluene and reflux was conducted for 2 hours, whereby the nano-particle accumulation was subjected to surface treatment to form a display layer 33 containing an electrochromic composition 33b.

Meanwhile, an ITO film with a thickness of about 150 nm was formed on the entire of the top surface of a 30 mm×30 mm glass substrate 12b by using a sputter method. Then, after a liquid in which 25 mass % of 2-ethoxyethyl acetate was added into a thermosetting electrically conductive carbon ink CH10 (produced by Jujo Chemical Corporation) was applied onto the ITO film by using a spin-coat method, annealing was conducted at 120° C. for 15 minutes whereby an opposing electrode 12a was formed and an apposing substrate 12 was obtained.

The display substrate 11 and the opposing substrate 12 were bonded via a 75 μm spacer 15 to obtain a cell. Then, a liquid in which 35 mass % of titanium oxide particles with an average primary particle diameter of 300 nm (produced by Ishihara Sangyo Kaisha, Ltd.) were dispersed in an electrolyte liquid 13a in which 20 mass % of tetrabutylammonium perchlorate was dissolved in dimethyl sulfoxide (DMSO) was enclosed in the cell whereby a white color reflective layer 14 was formed and a display element 30 was obtained.

[Color Development/Erasing Test]

When a negative electrode and a positive electrode were connected to a display electrode 11a and opposing electrode 12a of the display element 30, respectively, and a voltage of 3.0 V was applied for 1 second, yellow color development was provided. Then, when a voltage of −4.5 V was applied for 2 seconds, complete color erasing was provided and a white color was recovered. Furthermore, even though a voltage of 3.0 V was applied for 1 second and subsequently leaving for 300 seconds was conducted without applying a voltage, a color development state of the display element 30 was retained, whereby it was confirmed that an excellent image retention characteristic was provided.

Figure 10:
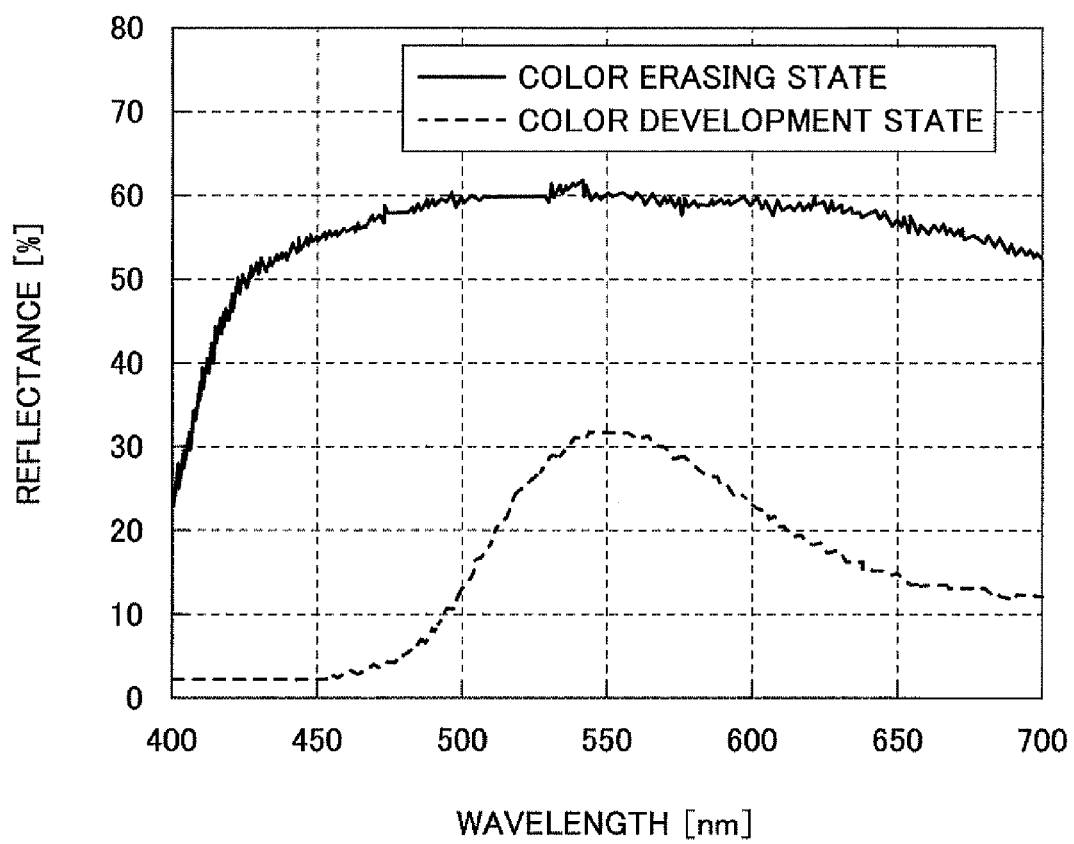
FIG. 10 is a diagram illustrating a reflection spectrum of a display element in practical example 2-1.
Figure 11:
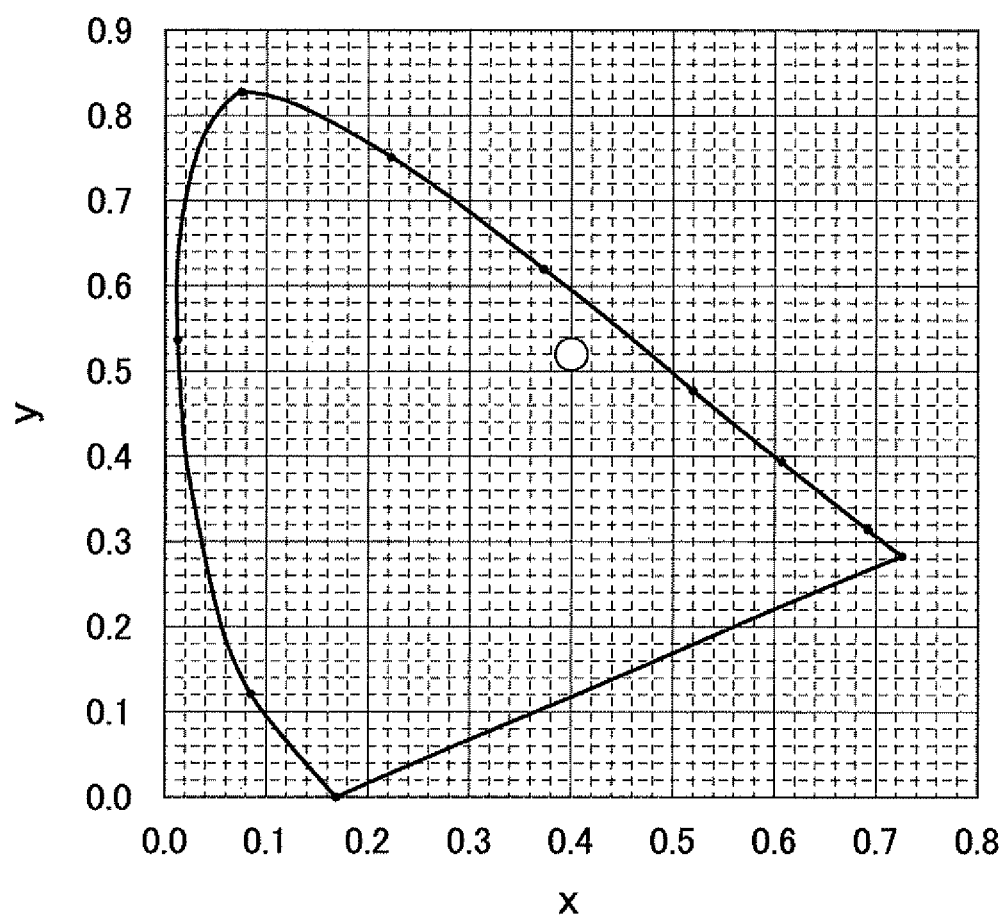
FIG. 11 is a diagram illustrating a result of a coordination transformation of a reflection spectrum at a color development state in FIG. 10 into a CIE color specification system.

When the display element 30 at a color development state or a color erasing state was irradiated with diffused light by using a spectrophotometric colorimeter LCD-5000 (produced by Otsuka Electronics Co., Ltd.), a reflection spectrum illustrated in FIG. 10 was obtained. Furthermore, FIG. 11 illustrates a result of a coordinate transformation of a reflection spectrum at a color development state in FIG. 10 into a CIE color specification system. From FIG. 10 and FIG. 11, it was confirmed that the width of a low reflectance region of the display electrode 30 in the visible region was narrow and a yellow color development was provided.

[Measurement of Light Absorption Spectrum]

The display substrate 11 on which the display layer 33 was formed was put in a quartz cell, and the quart cell was filled with an electrolyte liquid in which 20 mass % of tetrabutylammonium perchlorate was dissolved in dimethyl sulfoxide (DMSO), while a platinum electrode as a counter electrode and a $Ag/Ag^+$ electrode RE-7 (produced by BAS Corporation) as a reference electrode were used. When a voltage of −1.5 V was applied by using a potentiostat ALS-660C (produced by BAS Corporation), yellow color development was provided.

Figure 12:
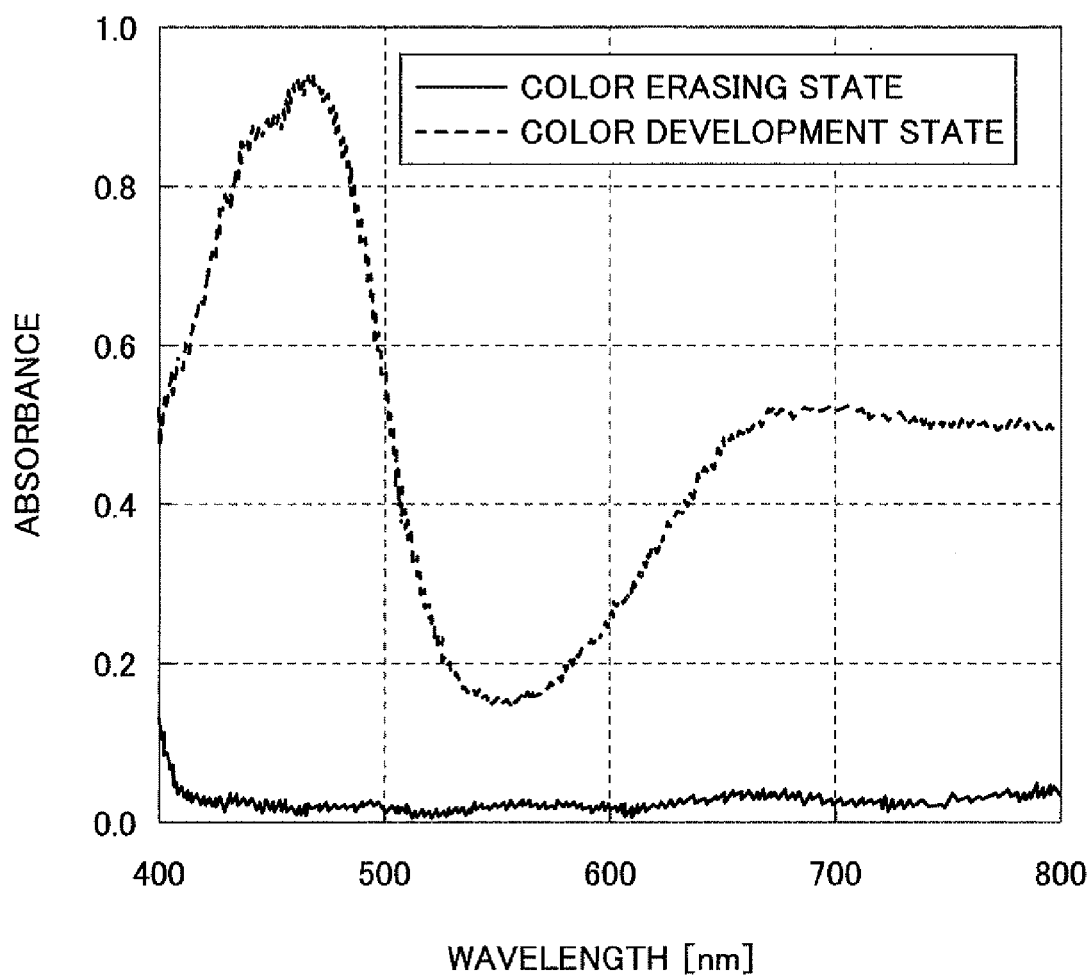
FIG. 12 is a diagram illustrating a light absorption spectrum of a display substrate on which a display layer in practical example 2-1 is formed.

When the quartz cell was irradiated with light by using a deuterium tungsten halogen light source DH-2000 (produced by Ocean Optics Inc.) and transmitted light was detected by a spectrometer USB4000 (produced by Ocean Optics Inc.), a light absorption spectrum illustrated in FIG. 12 was obtained.

From FIG. 12, it was confirmed that the display later 33 at a color development state had a sharp absorption peak near 470 nm.

Practical Example 2-2

Synthesis of compound (2-E)

Figure 13:
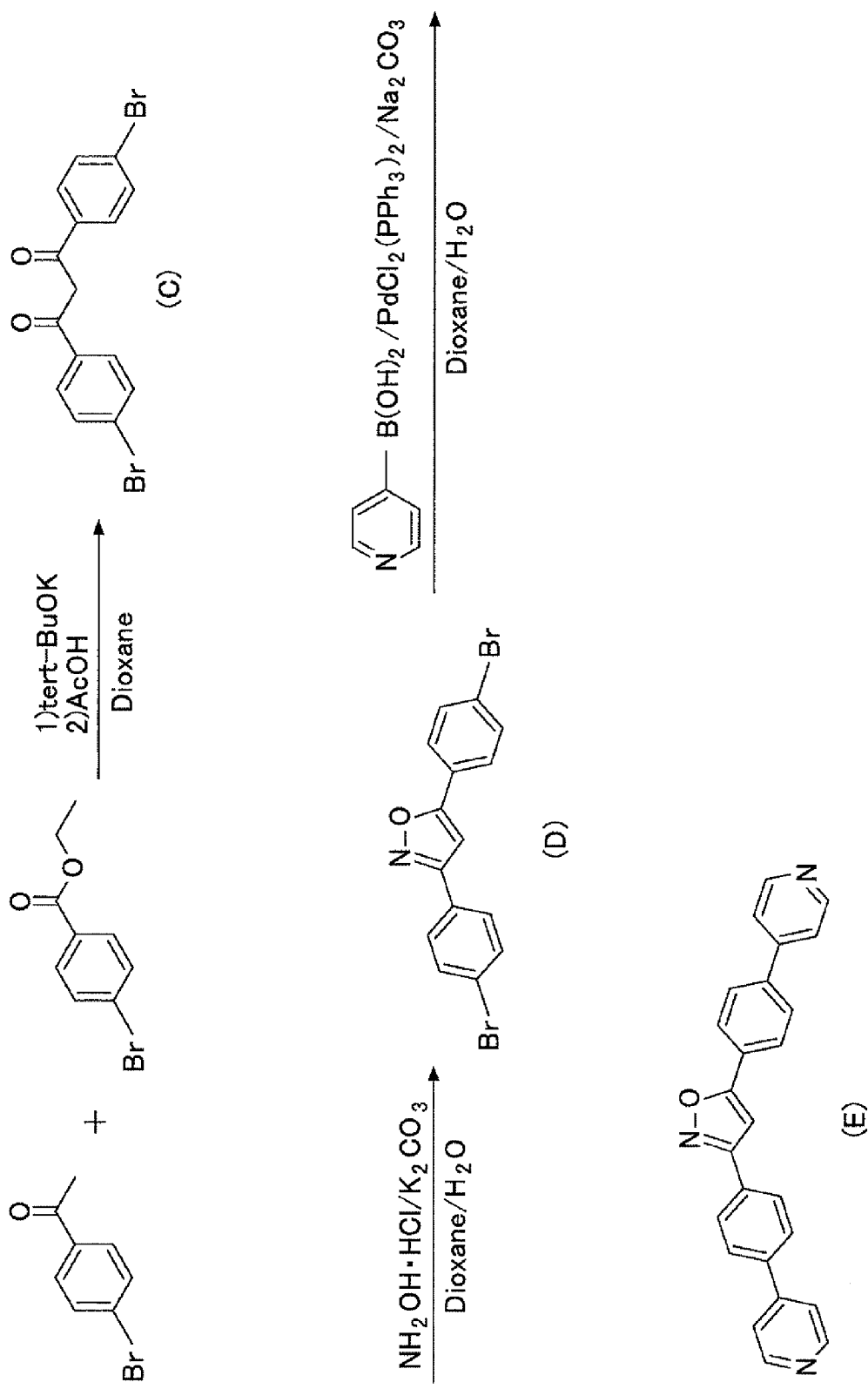
FIG. 13 is a diagram illustrating a flow of synthesis of compound (2-E).

FIG. 13 illustrates a flow of synthesis of compound (2-E).

After 4.0 g of 4-bromoacetophenone, 4.6 g of ethyl 4-bromobenzoate, and 30 ml of 1,4-dioxane were charged into a reaction flask and 4.4 g of potassium tert-butoxide was gently added thereto, agitation was conducted at 90° C. for 1 hour and standing to cool was conducted. After a reaction liquid was diluted with 80 ml of water, 7 ml of acetic acid was added to precipitate a product. After the precipitated product was filtered, washing with water and drying were conducted to obtain 2.6 g of compound (2-C).

5.6 g of hydroxylamine hydrochloride, 1.6 g of sodium hydroxide, and 40 ml of ethanol were charged into a reaction flask and agitation was conducted at 40° C. for 10 minutes. Then, after 3.8 g of compound (2-C) was thrown thereto and agitation under reflux was conducted for 1 hour, 2.9 g of sodium hydroxide was added thereto and agitation under reflux for 4 hours and standing to cool were conducted. After ethanol was distilled out from the reaction liquid, a residue was dissolved in water. Furthermore, after filtration, washing with water and frying were conducted to obtain 0.81 g of compound (2-D).

0.57 g of compound (2-D), 0.39 g of 4-pyridineboronic acid, 0.11 g of dichlorobis(triphenylphosphine)palladium (II), 0.48 g of sodium carbonate, 5 ml of water, and 15 ml of 1,4-dioxane were charged into a reaction flask substituted with nitrogen and agitation was conducted at 90° C. for 3 hours, standing to cool was conducted. After the reaction liquid was diluted with chloroform, filtration was conducted. After a filtrate was washed with water, drying with anhydrous sodium sulfate was conducted and chloroform was distilled out. An obtained solid was purified by silica gel column chromatography using a mixed solvent of chloroform/acetone (volume ratio 1/1) as an eluent to obtain 0.23 g of compound (2-E). When GC/MS measurement of compound (2-E) was conducted, the mass to charge ratio of a molecular ion peak was 377.

[Manufacturing of Display Element]

A display element 30 in which a display layer 33 containing an electrochromic composition 33b was formed was obtained by subjecting a nano-particle accumulation to surface treatment similarly to practical example 2-1 except that compound (2-E) was used instead of compound (2-B).

[Color Development/Erasing Test]

When a negative electrode and a positive electrode were connected to a display electrode 11a and opposing electrode 12a of the display element 30, respectively, and a voltage of 3.0 V was applied for 1 second, yellow color development was provided. Then, when a voltage of −4.5 V was applied for 2 seconds, complete color erasing was provided and a white color was recovered. Furthermore, even though a voltage of 3.0 V was applied for 1 second and subsequently leaving for 300 seconds was conducted without applying a voltage, a color development state of the display element 30 was retained, whereby it was confirmed that an excellent image retention characteristic was provided.

Figure 14:
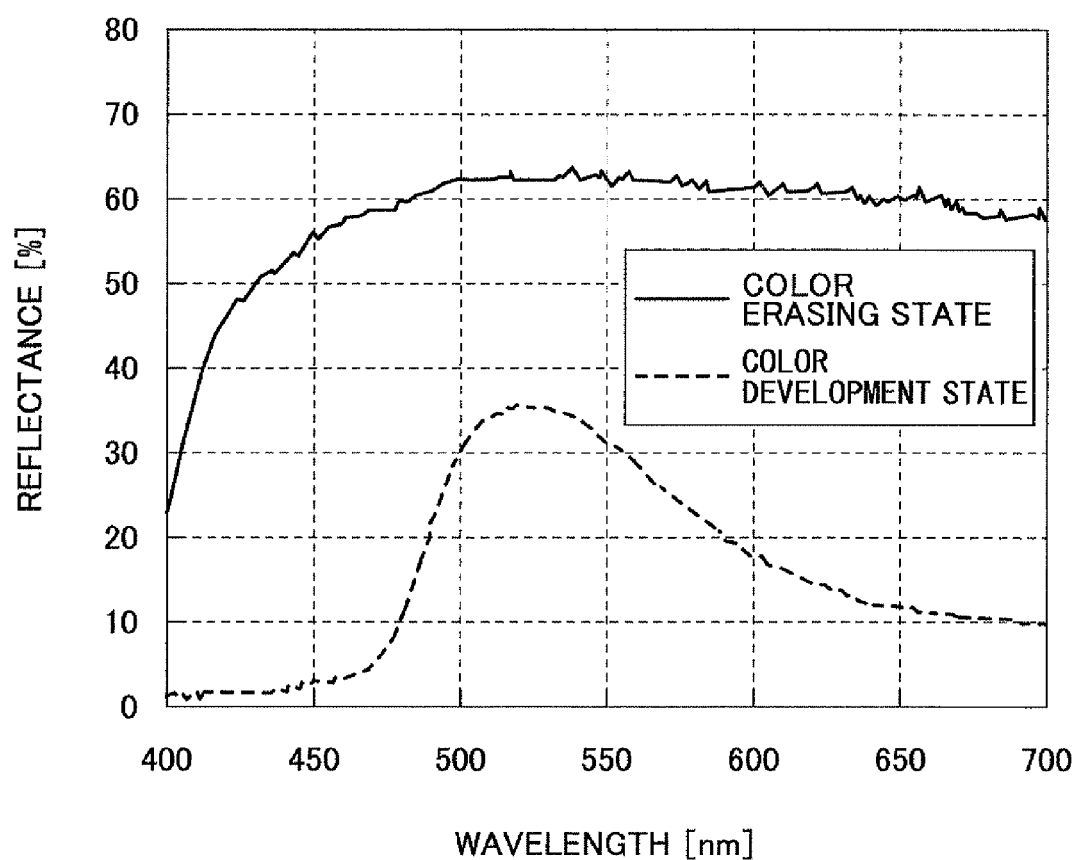
FIG. 14 is a diagram illustrating a reflection spectrum of a display element in practical example 2-2.
Figure 15:
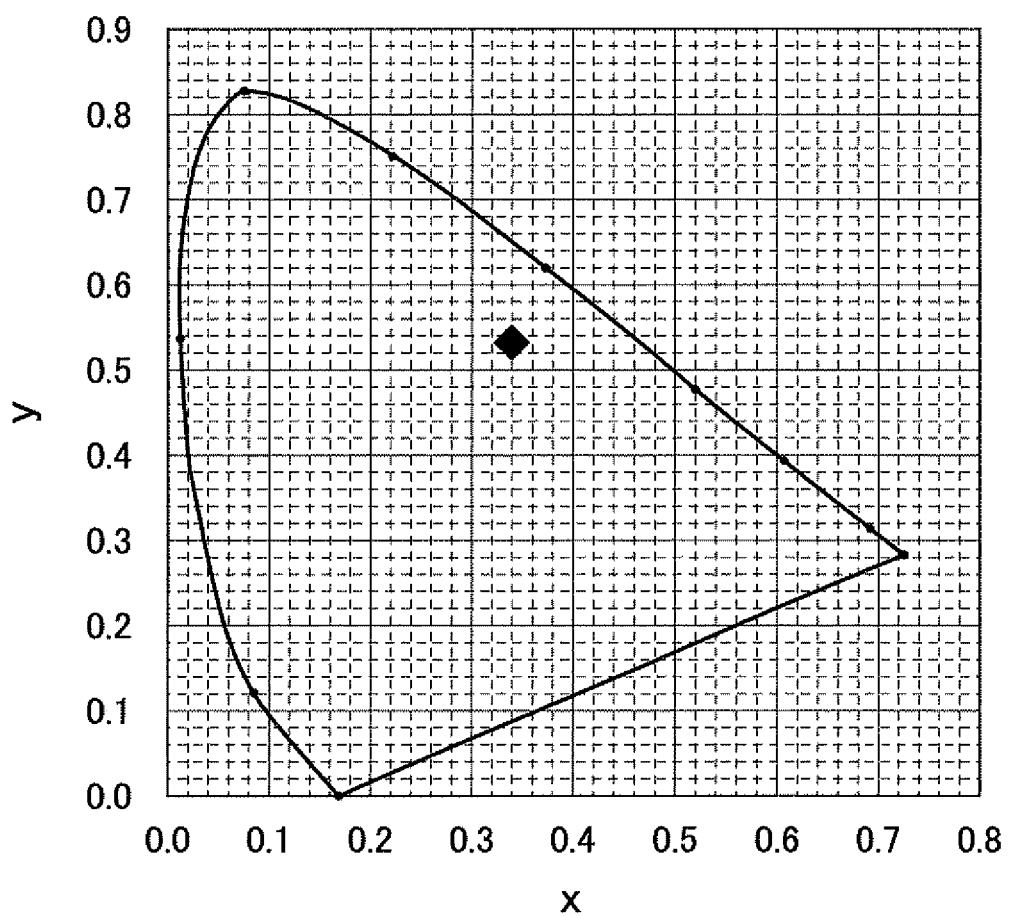
FIG. 15 is a diagram illustrating a result of a coordinate transformation of a reflection spectrum at a color development state in FIG. 9 into a CIE color specification system.

When the display element 30 at a color development state or a color erasing state was irradiated with diffused light by using a spectrophotometric colorimeter LCD-5000 (produced by Otsuka Electronics Co., Ltd.), a reflection spectrum illustrated in FIG. 14 was obtained. Furthermore, FIG. 15 illustrates a result of a coordinate transformation of a reflection spectrum at a color development state in FIG. 14 into a CIE color specification system. From FIG. 14 and FIG. 15, it was confirmed that the width of a low reflectance region of the display electrode 30 in the visible region was narrow and yellow color development was provided.

[Measurement of Light Absorption Spectrum]

The display substrate 11 on which the display layer 33 was formed was put in a quartz cell, and the quart cell was filled with an electrolyte liquid in which 20 mass % of tetrabutylammonium perchlorate was dissolved in dimethyl sulfoxide (DMSO), while a platinum electrode as a counter electrode and a $Ag/Ag^+$ electrode RE-7 (produced by BAS Corporation) as a reference electrode were used. When a voltage of −1.5 V was applied by using a potentiostat ALS-660C (produced by BAS Corporation), yellow color development was provided.

Figure 16:
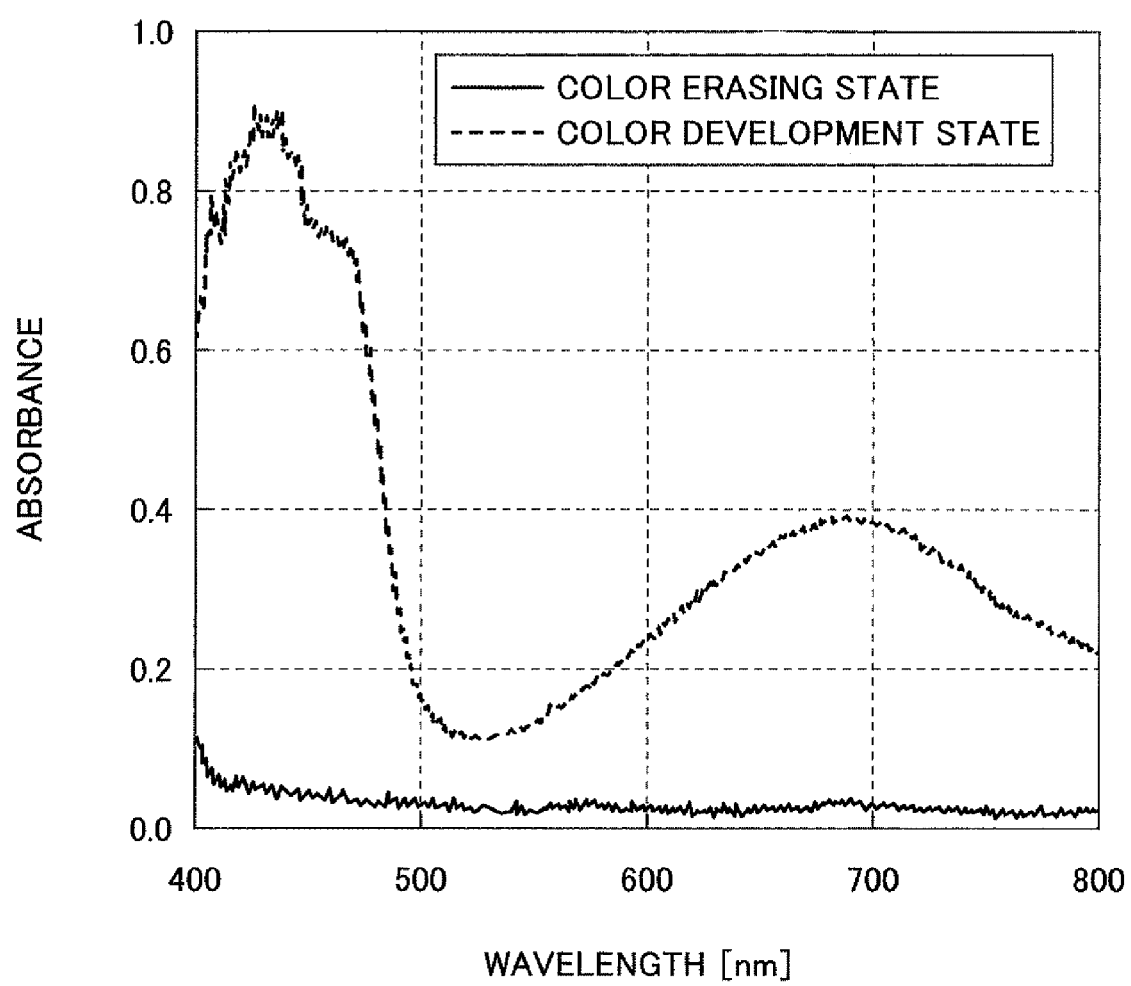
FIG. 16 is a diagram illustrating a light absorption spectrum of a display substrate on which a display layer in practical example 2-2 is formed.

When the quartz cell was irradiated with light by using a deuterium tungsten halogen light source DH-2000 (produced by Ocean Optics Inc.) and transmitted light was detected by a spectrometer USB4000 (produced by Ocean Optics Inc.), a light absorption spectrum illustrated in FIG. 16 was obtained.

From FIG. 16, it was confirmed that the display later 33 at a color development state had a sharp absorption peak near 430 nm.

Practical Example 2-3

Synthesis of Electrochromic Compound (2-1)

After 0.45 g of compound (2-B), a suitable amount of ethyl bromide, 3 ml of 1-propanol, and 6 ml of water were charged in a reaction flask and agitation was conducted at 90° C. for 40 hours, standing to cool was conducted. A reaction liquid was discharged into a mixed liquid of 15 ml of water and 30 ml of ethyl acetate, and an aqueous layer was fractionated. After the obtained aqueous layer and 20 ml of concentrated hydrochloric acid were charged in a reaction flask and agitation was conducted at 90° C. for 23 hours, standing to cool was conducted. After water was distilled out from the reaction liquid and a tar-like residue was dissolved in methanol, dropping into a mixed solvent of 2-propanol/ethanol (volume ratio 2/1) was conducted under agitation was conducted to crystallize a product. Furthermore, after filtration, washing with 2-propanol and drying were conducted to obtain 0.30 g of electrochromic compound (2-1).

[Manufacturing of Display Element]

As a display substrate 11 and an opposing substrate 12, 30 mm×30 mm glass substrates 11b and 12b (produced by AGC Fabritech Co., Ltd.) were used wherein a display electrode 11a and an opposing electrode 12a made of SnO$_2$ were formed on the entire of the top surfaces thereof, respectively.

The display substrate 11 and the opposing substrate 12 were bonded via a 75 μm spacer to obtain a cell. Then, an electrolyte liquid 13a in which 50 mass % of a 1 mass % solution of electrochromic compound (2-1) 13b in a mixed solvent of water/2,2,3,3-tetrafluoropropanol (mass ratio 1/9) was added into a liquid in which 20 mass % of tetrabutylammonium perchlorate was dissolved in dimethyl sulfoxide (DMSO) was enclosed in the cell to obtain a display element 10 having a configuration such that a white reflective layer 14 was not formed.

[Color Development/Erasing Test]

When a negative electrode and a positive electrode were connected to the display electrode 11a and opposing electrode 12a of the display element 10, respectively, and a voltage of 3.0 V was applied for 2 seconds, yellow color development was provided. Then, when a voltage of −3.0 V was applied for 4 seconds, complete color erasing was provided and a colorless and transparent state was recovered. Furthermore, even though a voltage 3.0 V was applied for 2 seconds and subsequently leaving for 300 seconds was conducted without applying a voltage, a color development state of the display element 10 was retained, whereby it was confirmed that an excellent image retention characteristic was provided.

Practical Example 2-4

Synthesis of Electrochromic Compound (2-15)

After 0.45 g of compound (2-B), 2.0 g of diethyl 8-bromooctylphosphonate, 3 ml of 1-propanol, and 6 ml of water were charged into a reaction flask and agitation was conducted at 90° C. for 40 hours, standing to cool was conducted. A reaction liquid was discharged into a mixed liquid of 15 ml of water and 30 ml of ethyl acetate, and an aqueous layer was fractionated. After the obtained aqueous layer and 20 ml of concentrated hydrochloric acid were charged in a reaction flask and agitation was conducted at 90° C. for 23 hours, standing to cool was conducted. After water was distilled out from the reaction liquid and a tar-like residue was dissolved in methanol, dropping into a mixed solvent of 2-propanol/ethanol (volume ratio 2/1) was conducted under agitation was conducted to crystallize a product. Furthermore, after filtration, washing with 2-propanol and drying were conducted to obtain 0.40 g of electrochromic compound (2-15).

[Manufacturing of Display Element]

A display electrode 11a having a thickness of about 100 nm and made of ITO was formed on a 16 mm×23 mm area on the top surface of a 30 mm×30 mm glass substrate 11b by using a sputter method to obtain a display substrate 11. The resistance of the display electrode 11a between end portions thereof was measured and was about 200 Ω.

Then, a dispersion liquid SP210 (produced by Showa Titanium Corporation) of titanium oxide nano-particles was applied onto the display electrode 11a by using a spin-coat method and annealing was conducted at 120° C. for 15 minutes to form a nano-particle accumulation. Furthermore, a 0.9 mass % solution of electrochromic compound (2-15) in 2,2,3,3-tetrafluoropropanol was applied thereto by using a spin-coat method and annealing was conducted at 120° C. for 10 minutes whereby electrochromic compound (2-15) was adsorbed onto a surface of the nano-particle accumulation to form a display layer 33 containing an electrochromic composition 33b.

Meanwhile, an ITO film with a thickness of about 150 nm was formed on the entire of the top surface of a 30 mm×30 mm glass substrate 12b by using a sputter method. Then, after a liquid in which 25 mass % of 2-ethoxyethyl acetate was added into a thermosetting electrically conductive carbon ink CH10 (produced by Jujo Chemical Corporation) was applied onto the ITO film by using a spin-coat method, annealing was conducted at 120° C. for 15 minutes whereby an opposing electrode 12a was formed and an apposing substrate 12 was obtained.

The display substrate 11 and the opposing substrate 12 were bonded via a 75 μm spacer 15 to obtain a cell. Then, a liquid in which 35 mass % of titanium oxide particles with an average primary particle diameter of 300 nm (produced by Ishihara Sangyo Kaisha, Ltd.) were dispersed in an electrolyte liquid 13a in which 20 mass % of tetrabutylammonium perchlorate was dissolved in dimethyl sulfoxide (DMSO) was enclosed in the cell whereby a white color reflective layer 14 was formed and a display element 30 was obtained.

[Color Development/Erasing Test]

When a negative electrode and a positive electrode were connected to the display electrode 11a and opposing electrode 12a of the display element 30, respectively, and a voltage of 3.0V was applied for 1 second, yellow color development was provided. Then, when a voltage of −4.5 V was applied for 2 seconds, complete color erasing was provided and white color was recovered. Furthermore, even though a voltage of 3.0 V was applied for 1 second and subsequently leaving for 300 seconds was conducted without applying a voltage, a color development state of the display element 30 was retained, whereby it was confirmed that an excellent image retention characteristic was provided.

Comparative Example 2-1

Manufacturing of Display Element

A display element 30 was obtained similarly to practical example 2-1 except that a 1 mass % solution of a viologen compound represented by a chemical formula of

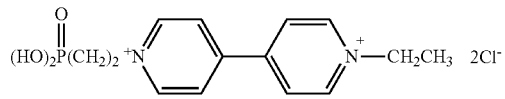

in 2,2,3,3-tetrafluoropropanol was applied onto a display substrate 11 on which a nano-particle accumulation was formed, by using a spin-coat method, and annealing was conducted at 120° C. for 10 minutes, whereby the viologen compound was adsorbed on a surface of the nano-particle accumulation to form a display layer 33 containing an electrochromic composition 33b.

[Color Development/Erasing Test]

When a negative electrode and a positive electrode were connected to a display electrode 11a and opposing electrode 12a of the display element 30, respectively, and a voltage of 3.0 V was applied for 1 second, blue color development was provided. Then, when a voltage of −4.5 V was applied for 2 seconds, complete color erasing was provided and a white color was recovered. Furthermore, even though a voltage of 3.0 V was applied for 1 second and subsequently leaving for 300 seconds was conducted without applying a voltage, a color development state of the display element 30 was retained, whereby it was confirmed that an excellent image retention characteristic was provided.

Figure 17:
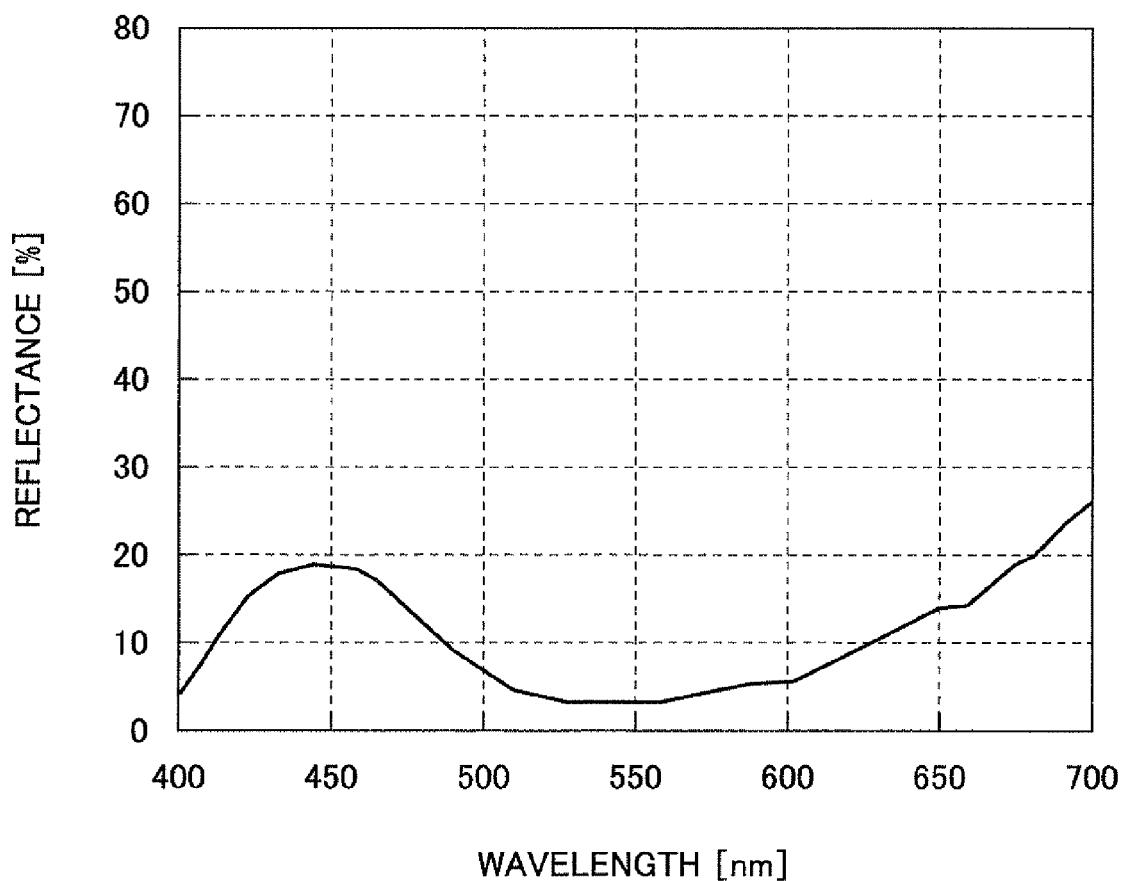
FIG. 17 is a diagram illustrating a reflection spectrum of a display element in comparative example 2-1.

When the display element 30 at a color development state or a color erasing state was irradiated with diffused light by using a spectrophotometric colorimeter LCD-5000 (produced by Otsuka Electronics Co., Ltd.), a reflection spectrum illustrated in FIG. 17 was obtained. From FIG. 17, it was confirmed that the width of a low reflectance region of the display electrode 30 in the visible region was broad and a broad light absorption was provided, whereby blue color development was provided.

Practical Example 3-1

(3-A) Synthesis of Intermediate 3-8 of a Structural Formula 3-8

2.2 g of 4-vinylpyridine, 2.4 g of m-bromobenzene, 0.18 g of palladium acetate, 0.49 g of tri-o-tolylphosphine, 4.0 g of triethylamine, and 10 ml of acetonitrile were charged into a reaction flask substituted with nitrogen and this mixture was agitated at 80° C. for 12 hours. After standing to cool, a reaction mixture was diluted with chloroform and insoluble matters were filtered out, then a chloroform solution was washed with water and dried with anhydrous sodium sulfate and subsequently chloroform was distilled out. An obtained solid was purified by silica gel column chromatography with an eluent of toluene/acetone (volume ratio; 1/1) to obtain 2.2 g of intermediate 3-8. When this GC/MS measurement was conducted, a molecular ion peak was provided at M=283.

A flow of synthesis of such intermediate 8 is illustrated below.

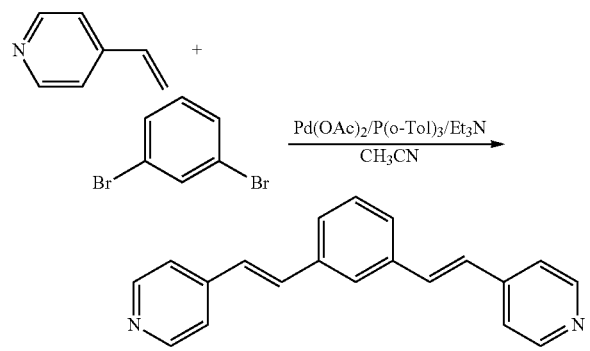

(3-B) Formation of Display Electrode and Electrochromic Display Layer

A dispersion liquid (SP210 produced by Showa Titanium Corporation) of titanium oxide nano-particles was applied by a spin-coat method onto a part of a 30 mm×30 mm glass substrate with FTO and annealing was conducted at 120° C. for 15 minutes to form a titanium oxide particle film. The thickness of the titanium oxide film was about 1.5 μm.

Then, a 0.2 wt % solution of 3-bromopropyltrichlorosilane in toluene was prepared and the glass substrate with FTO on which the above-mentioned titanium oxide film was applied was dipped therein for 30 minutes, whereby 3-bromopropylsilane was bonded to a surface of the titanium oxide film.

Afterward, a 1 wt % solution of intermediate 3-8 synthesized in (3-A) in toluene was prepared, then the above-mentioned substrate was dipped therein, and reflux was conducted at 120° C. for 2 hours to react intermediate 3-8 with 3-bromopropylsilane.

(3-C) Formation of Opposing Electrode

Meanwhile, a 30 mm×30 mm glass substrate was prepared and an ITO film with a thickness of about 150 nm was formed on the entire of its top surface by a sputter method to form an opposing electrode 2. Furthermore, a solution prepared by adding 25 wt % of 2-ethoxyethyl acetate into a thermosetting electrically conductive carbon ink (CH10 produced by Jujo Chemical Corporation) was applied by a spin-coat method onto the top surface of a glass substrate in which a transparent electrically conductive thin film was formed on the entire surface thereof, and annealing was conducted at 120° C. for 15 minutes to form an opposing electrode.

(3-D) Manufacturing of Electrochromic Display Device

The display substrate and the opposing substrate were bonded via a 75 μm spacer to manufacture a cell. Then, 35 wt % of titanium oxide particles with an average primary particle diameter of 300 nm (CR50 produced by Ishihara Sangyo Kaisha, Ltd.) were dispersed in a solution in which 20 wt % of tetrabutylammonium perchlorate was dissolved in dimethyl sulfoxide to prepare an electrolyte solution and it was enclosed in a cell to manufacture an electrochromic display element.

(3-E) Color Development/Erasing Test

An evaluation of color development/erasing of the manufactured electrochromic display element was conducted.

Figure 21:
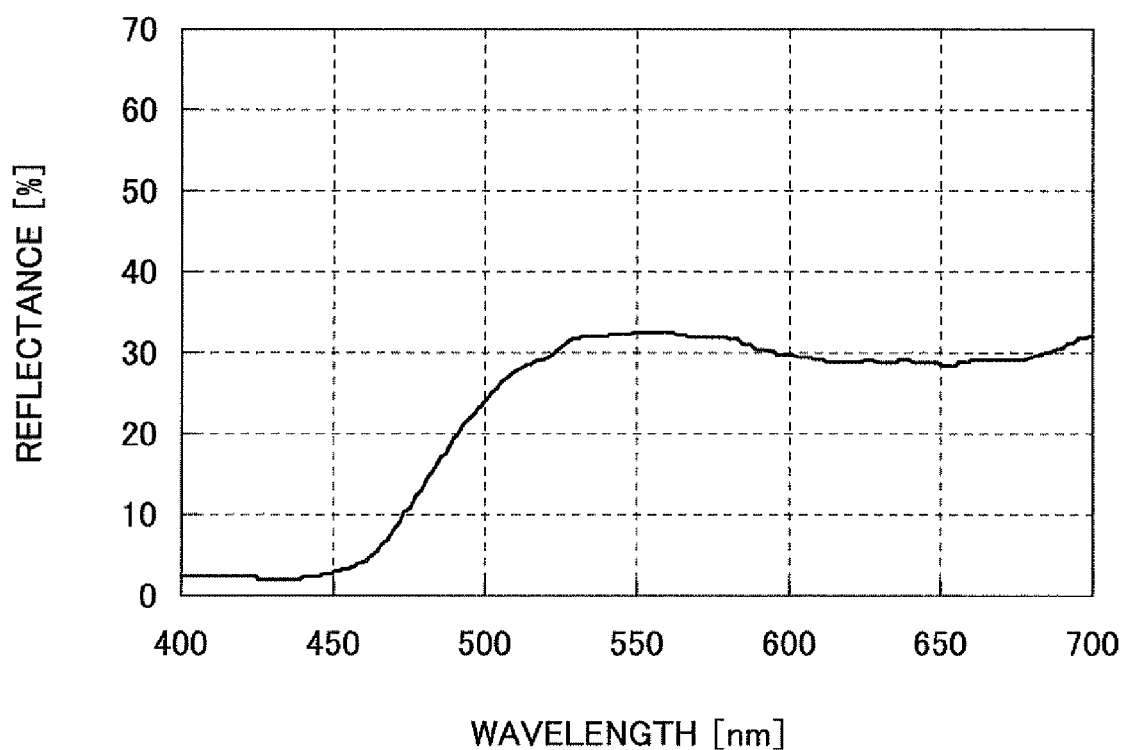
FIG. 21 is a graph illustrating a spectrum of an electrochromic display element manufactured in practical example 3-1 at the time of color development thereof.
Figure 22:
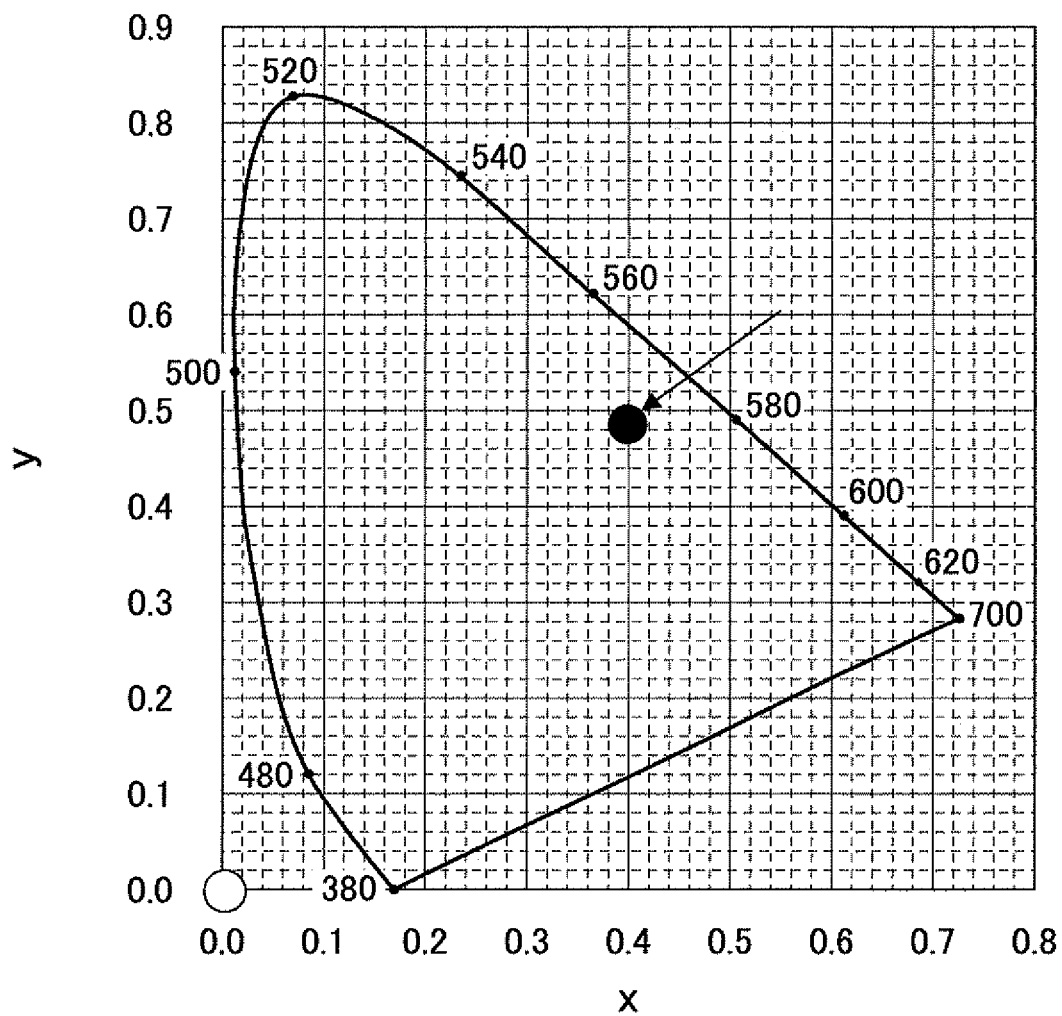
FIG. 22 is a graph illustrating a result of a coordinate transformation of a spectrum of an electrochromic display

The evaluation of color development/erasing was conducted by diffused light irradiation using a spectrophotometric colorimeter LCD-5000 produced by Otsuka Electronics Co., Ltd. When a negative electrode and a positive electrode were connected to display electrode 1 and opposing electrode 2 of the display element, respectively, and a voltage of 3.0 V was applied for 1 second, the display element provided yellow color development. Furthermore, when a reverse voltage of −2.0 V was applied for 1 second, complete color erasing was provided and a white color was recovered. FIG. 21 illustrates a reflection spectrum at the time of color development. Furthermore, FIG. 22 illustrates a result of a coordinate transformation of this spectrum into a CIE color specification system. From FIG. 21 and FIG. 22, it could be confirmed that a clear yellow color development was provided.

The display electrode on which the electrochromic display layer was formed was put in a quartz cell, and the inside of the cell was filled with an electrolyte liquid in which 20 wt % of tetrabutylammonium perchlorate was dissolved in dimethyl sulfoxide, while a platinum electrode as a counter electrode and a Ag/Ag$^+$ electrode RE-7 (produced by BAS Corporation) as a reference electrode were used. When this quartz cell was irradiated with deuterium tungsten halogen light (DH-2000 produced by Ocean Optics Inc.) and transmitted light was detected by a spectrometer (USB4000 produced by Ocean Optics Inc.), an absorption spectrum was measured.

Figure 23:
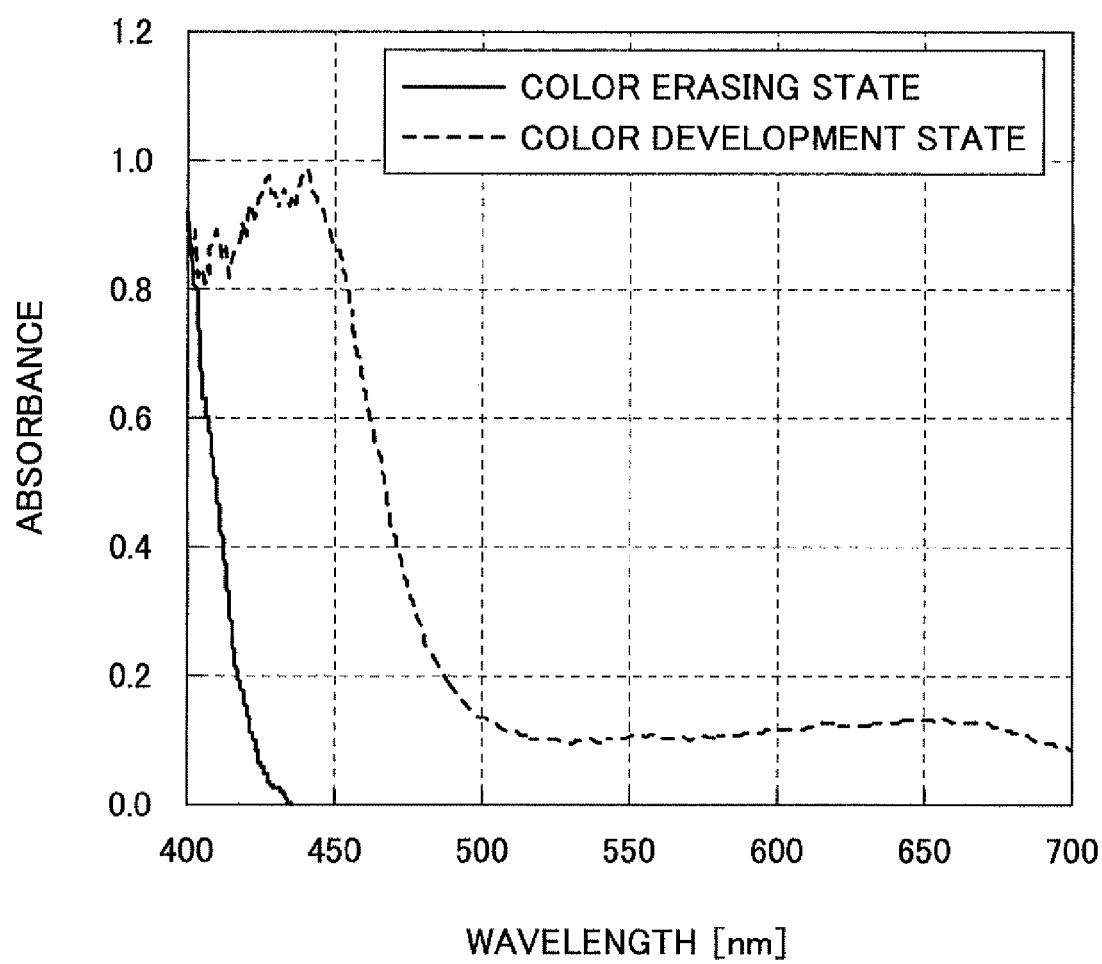
FIG. 23 is a graph illustrating an absorption spectrum of an electrochromic display layer manufactured in practical example 3-1 before and after application of a voltage thereto.

When a voltage of −1.5V was applied by using a potentiostat (ALS-660C produced by BAS Corporation), yellow color development was provided. FIG. 23 illustrates absorption spectra before and after application of a voltage.

Practical Example 3-2

(3-A) Synthesis of Intermediate 3-14 of a Structural Formula 3-14

1.8 g of 4-vinylpyridine, 1.6 g of 1,3,5-tribromobenzene, 0.13 g of palladium acetate, 0.36 g of tri-o-tolylphosphine, 3.0 g of triethylamine, and 5 ml of acetonitrile were charged into a reaction flask substituted with nitrogen and this mixture was agitated at 80° C. for 12 hours. After standing to cool, a reaction mixture was diluted with chloroform and insoluble matters were filtered out, then a chloroform solution was washed with water and dried with anhydrous sodium sulfate and subsequently chloroform was distilled out. An obtained solid was purified by silica gel column chromatography with an eluent of toluene/ethanol (volume ratio; 20/1) to obtain 0.75 g of intermediate 3-14. When this GC/MS measurement was conducted, a molecular ion peak was provided at M=383.

(3-B) Manufacturing of Display Electrode, Electrochromic Display Layer, Opposing Electrode, and Electrochromic Display Device A display electrode, an electrochromic display layer, an opposing electrode, and an electrochromic display device were manufactured by using an intermediate 4-14 synthesized in (3-A) and a method similar to that of practical example 3-1.

(3-C) Color Development/Erasing Test

An evaluation of color development/erasing of the manufactured electrochromic display element was conducted similar to practical example 3-1.

When a negative electrode and a positive electrode were connected to the display electrode and opposing electrode of the display element, respectively, and a voltage of 2.5 V was applied for 1 second, the display element provided yellow color development.

Figure 24:
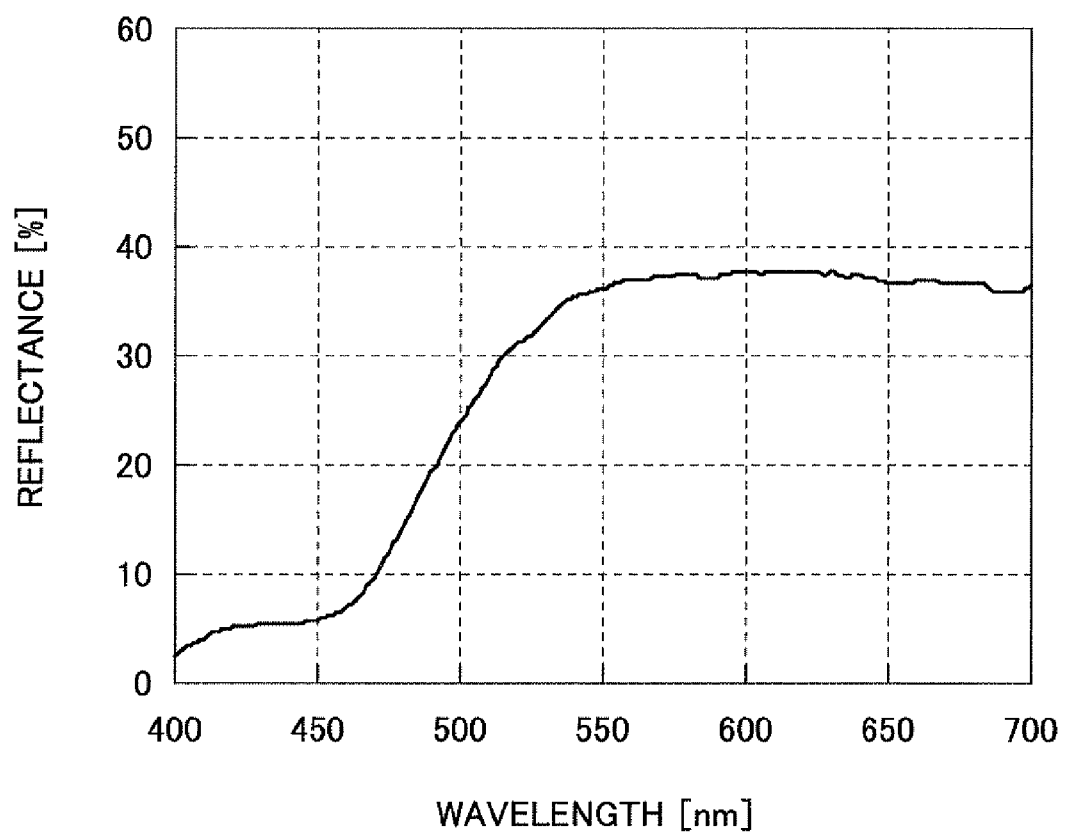
FIG. 24 is a graph illustrating a spectrum of an electrochromic display element manufactured in practical example 3-2 at the time of color development thereof.
Figure 25:
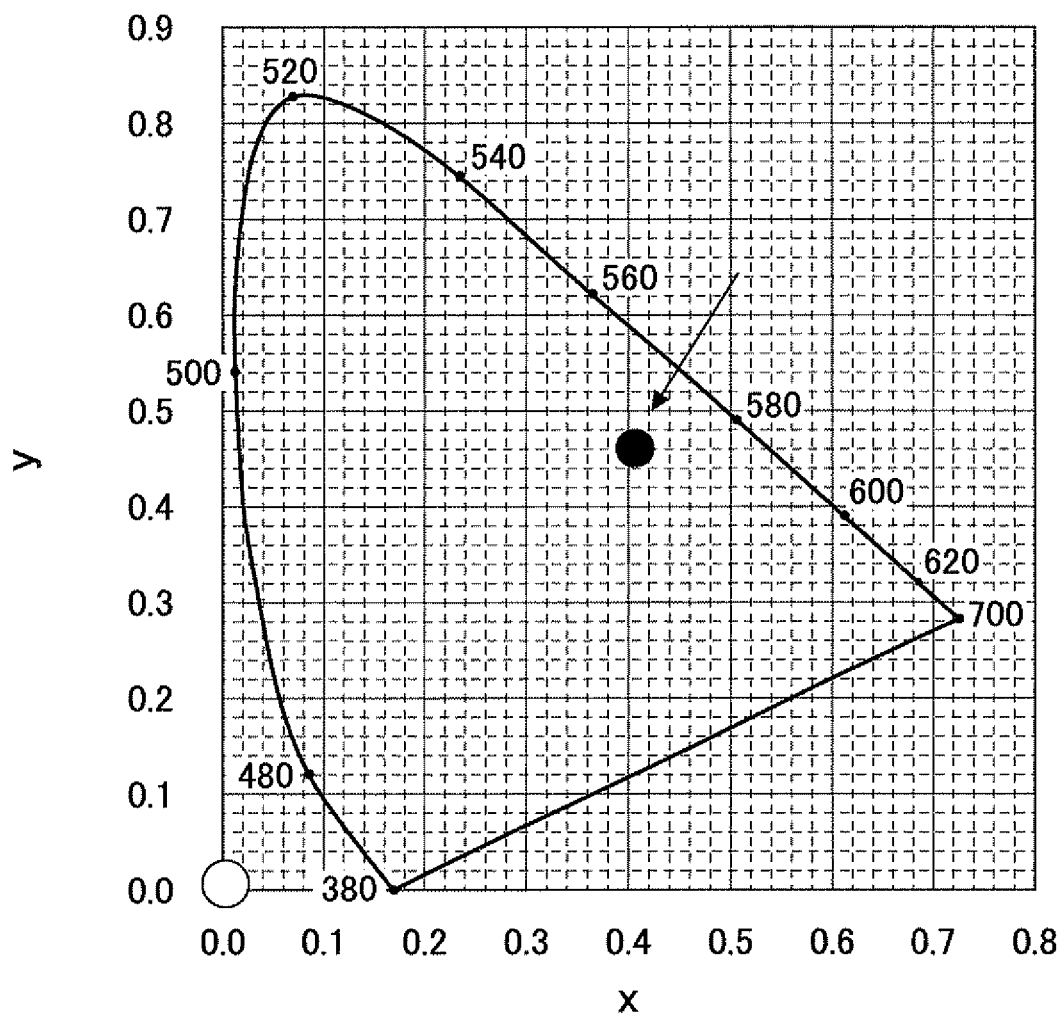
FIG. 25 is a graph illustrating a result of a coordinate transformation of a spectrum of an electrochromic display element manufactured in practical example 3-2 at the time of color development thereof into a CIE color specification system.

Furthermore, when a reverse voltage of −3.0 V was applied for 1 second, complete color erasing was provided and a white color was recovered. FIG. 24 illustrates a reflection spectrum at the time of color development. Furthermore, FIG. 25 illustrates a result of a coordinate transformation of this spectrum into a CIE color specification system. From FIG. 24 and FIG. 25, it could be confirmed that a clear yellow color development was provided.

Furthermore, an absorption spectrum was measured by a method similar to that of practical example 3-1.

Figure 26:
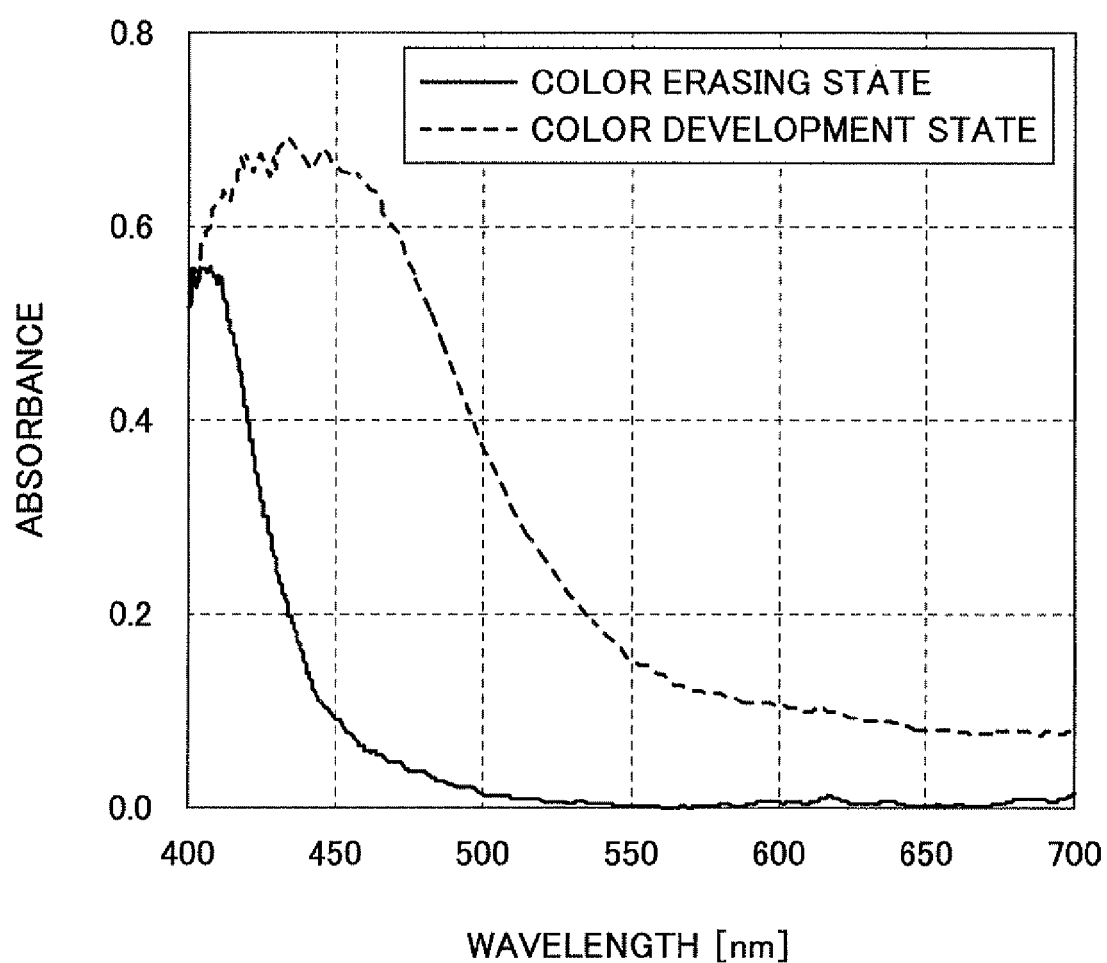
FIG. 26 is a graph illustrating an absorption spectrum of an electrochromic display layer manufactured in practical example 3-2 before and after application of a voltage thereto.

When a voltage of −1.5 V was applied by using a potentiostat (ALS-660C produced by BAS Corporation), yellow color development was provided. FIG. 26 illustrates absorption spectra before and after application of a voltage.

Practical Example 3-3

(3-A) Synthesis of Intermediate 3-11 of a Structural Formula 3-11

0.84 g of 4-vinylpyridine, 1.2 g of 3,5-dibromotrimethylsilylbenzene, 0.07 g of palladium acetate, 0.19 g of tri-o-tolylphosphine, 0.89 g of triethylamine, and 20 ml of acetonitrile were charged into a reaction flask substituted with nitrogen and this mixture was agitated at 80° C. for 12 hours. After standing to cool, a reaction mixture was diluted with chloroform and insoluble matters were filtered out, then a chloroform solution was washed with water and dried with anhydrous sodium sulfate and subsequently chloroform was distilled out. An obtained solid was purified by silica gel column chromatography with an eluent of toluene/acetone (volume ratio; 1/1) to obtain 0.89 g of intermediate 3-11. When this GC/MS measurement was conducted, a molecular ion peak was provided at M=356.

(3-B) Manufacturing of Display Electrode, Electrochromic Display Layer, Opposing Electrode, and Electrochromic Display Device A display electrode, an electrochromic display layer, an opposing electrode, and an electrochromic display device were manufactured by using an intermediate 4-11 synthesized in (3-A) and a method similar to that of practical example 3-1.

(3-C) Color Development/Erasing Test

An evaluation of color development/erasing of the manufactured electrochromic display element was conducted similar to practical example 3-1.

When a negative electrode and a positive electrode were connected to the display electrode and opposing electrode of the display element, respectively, and a voltage of 2.7 V was applied for 1 second, the display element provided yellow color development. Furthermore, when a reverse voltage of −2.0 V was applied for 1 second, complete color erasing was provided and a white color was recovered.

Practical Example 3-4

(3-A) Synthesis of that of a Structural Formula 3-7

0.2 g of intermediate 3-8 synthesized in practical example 3-1, 1.0 g of diethyl bromoethylphosphonate, 3 ml of 1-propanol, and 6 ml of water were charged, and this mixture was agitated at 90° C. for 40 hours. After standing to cool, a reaction mixture was discharged into a mixed liquid of 15 ml of water and 30 ml of ethyl acetate and an aqueous layer was fractionated. After this aqueous layer was charged into a reaction flask, 10 ml of concentrated hydrochloric acid was added thereto and agitation was conducted at 90° C. for 23 hours. After standing to cool, water was distilled out from the reaction mixture under a reduced pressure, then a tar-like residue was dissolved in methanol, then a tar-like residue was dissolved in methanol, and this methanol solution was dropped into 2-propanol/ethanol (volume ratio; 2/1) under agitation to crystallize a product. This was filtered and collected and washing with 2-propanol and drying were conducted to obtain 0.15 g of that of structural formula 3-7.

(3-B) Manufacturing of Display Electrode, Electrochromic Display Layer, Opposing Electrode, and Electrochromic Display Device A dispersion liquid (SP210 produced by Showa Titanium Corporation) of titanium oxide nano-particles was applied by a spin-coat method onto a part of a 30 mm×30 mm glass substrate with FTO and annealing was conducted at 120° C. for 15 minutes to form a titanium oxide particle film. The thickness of the titanium oxide film was about 1.5 μm.

Then, a 5 mM aqueous solution of that of structural formula 3-7 was prepared and the glass substrate with FTO on which the above-mentioned titanium oxide film was applied was dipped therein for 30 minutes, whereby the electrochromic compound with structural formula 3-7 was adsorbed to a surface of the titanium oxide film to manufacture a display electrode.

Furthermore, an opposing electrode and an electrochromic display device were manufactured by a method similar to practical example 3-1.

(3-C) Color Development/Erasing Test

An evaluation of color development/erasing of the manufactured electrochromic display element was conducted similar to practical example 3-1.

When a negative electrode and a positive electrode were connected to the display electrode and opposing electrode of the display element, respectively, and a voltage of 3.0 V was applied for 1 second, the display element provided yellow color development. Furthermore, when a reverse voltage of −2.0 V was applied for 1 second, complete color erasing was provided and a white color was recovered.

Practical Example 3-5

Two equivalent of ethyl bromide was reacted with intermediate 3-8 synthesized in practical example 3-1 whereby structural formula 3-5 was synthesized. Then, a solution of water/2,2,3,3-tetrafluoropropanol (10 wt %) was prepared and 1 wt % of that of structural formula 3-5 was dissolved therein to provide an electrochromic compound solution. 50 wt % of the electrochromic compound solution was added into an electrolyte liquid in which 20 wt % of tetrabutylammonium perchlorate was dissolved in dimethyl sulfoxide, and 30 mm×30 mm glass substrates with an electrically conductive film made of $SnO_2$ (produced by AGC Fabritech Co., Ltd.) as a display substrate and an opposing substrate were bonded via a 75 μm spacer and enclosed in a cell, whereby an electrochromic display element 10 was manufactured.

When a voltage of 3.0 V was applied to the manufactured display element for 2 seconds, the display element provided yellow color development. Furthermore, when a reverse voltage of −1.5 V was applied for 2 second, complete color erasing was provided and a transparency was recovered.

Practical Example 3-6

(3-A) Synthesis of that of a Structural Formula 3-17

2.2 g of 4-vinylpyridine, 2.4 g of 1,4-dibromobenzene, 0.18 g of palladium acetate, 0.49 g of tri-o-tolylphosphine, 4.0 g of triethylamine, and 10 ml of acetonitrile were added into a 50 ml flask and the inside of such a system was substituted with nitrogen. Temperature was raised to 75° C. and reaction was conducted overnight to precipitate a crystal. The precipitate was filtered and washed with acetonitrile. After an obtained crystal was dissolved in chloroform and RADIOLIGHT was added thereto, filtration was conducted and a filtrate was concentrated to obtain 4.4 g of a coarse crystal. The coarse crystal was dissolved in methanol/water, subsequently filtered, and washed with hot water. Furthermore, disintegration purification was conducted with hot acetonitrile to obtain 2.2 g of intermediate 3-17 which was a pale yellow crystal.

When GC/MS measurement of this compound was conducted, a molecular ion peak was provided at M=284. A flow of synthesis of such intermediate 17 is illustrated below.

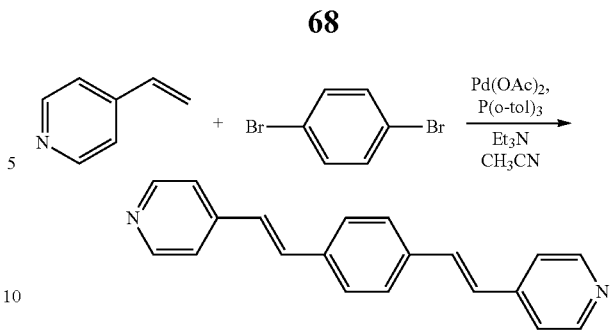

0.2 g of intermediate 3-17, 1.0 g of diethyl bromoethylphosphonate, 3 ml of 1-propanol, and 6 ml of water were charged and this mixture was agitated at 90° C. for 45 hours. After standing to cool, a reaction mixture was discharged into a mixed liquid of 15 ml of water and 30 ml of ethyl acetate and an aqueous layer was fractionated. After this aqueous layer was charged into a reaction flask, 10 ml of concentrated hydrochloric acid was added thereto and agitation was conducted at 90° C. for 30 hours. After standing to cool, water was distilled out from the reaction mixture under a reduced pressure, then a tar-like residue was dissolved in methanol, and this methanol solution was dropped into 2-propanol/ethanol (volume ratio; 2/1) under agitation to crystallize a product. This was filtered and collected and washing with 2-propanol and drying were conducted to obtain 0.15 g of that of structural formula 3-17.

(3-B) Manufacturing of Display Electrode, Electrochromic Display Layer, Opposing Electrode, and Electrochromic Display Device A display electrode, an electrochromic display layer, an opposing electrode, and an electrochromic display device were manufactured by a method similar to that of practical example 3-4.

(3-C) Color Development/Erasing Test

An evaluation of color development/erasing of the manufactured electrochromic display element was conducted similar to practical example 3-1.

When a negative electrode and a positive electrode were connected to the display electrode and opposing electrode of the display element, respectively, and a voltage of 3.0 V was applied for 1 second, the display element provided cyan color development. Furthermore, when a reverse voltage of −3.0 V was applied for 1 second, color erasing was provided and a pale yellow color was recovered.

Practical Example 3-7

(3-A) Synthesis of that of a Structural Formula 3-25

1.8 g of bisbromomethyldurene and 2.1 g of triethyl phosphite were charged into a 50 ml three-necked reactor and heating to and agitation at 110 to 120° C. were conducted. At this temperature, reaction was conducted for 1 hour. When standing to cool to room temperature was conducted, a solid was precipitated. Hexane was added and filtration was conducted. An obtained crystal was dried to obtain 2.0 g of 2,3,5,6-tetramethyl-1,4-bis(diethylphosphonylmethyl)benzene.

0.87 g of 2,3,5,6-tetramethyl-1,4-bis(diethylphosphonylmethyl)benzene, 20 ml of DMF (dewatered), and 0.47 g of 4-formylpyridine were charged into a 50 ml three-necked reactor. After substitution with nitrogen was conducted, 10 ml of a solution of 0.56 g of potassium t-butoxide in DMF was gently dropped thereto, and accordingly, changed to a blue-green solution. Reaction was conducted at 30 to 40° C. for 2 hours. A reaction liquid was discharged into water and sodium chloride was added to precipitate a solid. A precipitated solid was filtered, brought out, and dried to obtain 0.40 g of a coarse product. The coarse product was purified by a silica gel column (toluene/acetone 3/1→1/1) to obtain 0.30 g of intermediate 3-25. When GC/MS measurement of this compound was conducted, a molecular ion peak was provided at M=340.

A flow of synthesis of such intermediate 25 is illustrated below.

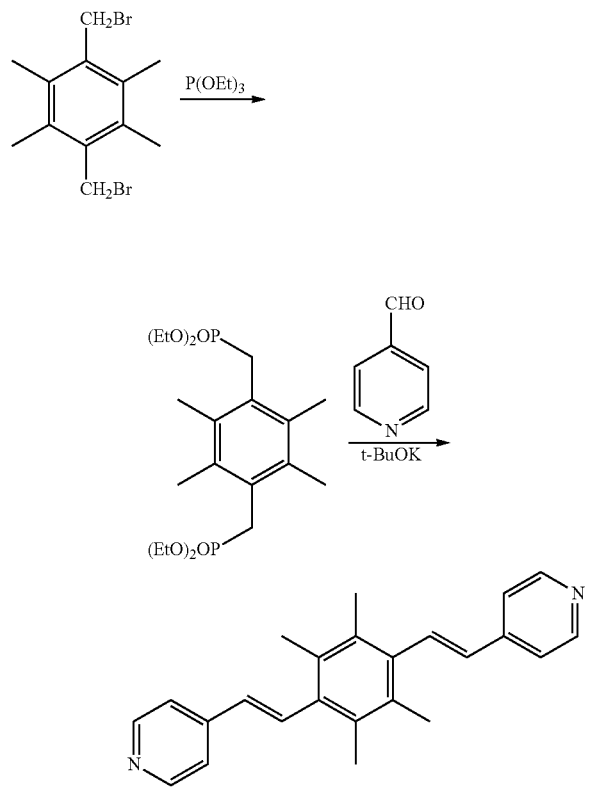

0.2 g of intermediate 3-25, 1.0 g of diethyl bromoethylphosphonate, 3 ml of 1-propanol, and 6 ml of water were charged and this mixture was agitated at 90° C. for 35 hours. After standing to cool, a reaction mixture was discharged into a mixed liquid of 15 ml of water and 30 ml of ethyl acetate and an aqueous layer was fractionated. After this aqueous layer was charged into a reaction flask, 10 ml of concentrated hydrochloric acid was added thereto and agitation was conducted at 90° C. for 20 hours. After standing to cool, water was distilled out from the reaction mixture under a reduced pressure, then a tar-like residue was dissolved in methanol, and this methanol solution was dropped into 2-propanol/ethanol (volume ratio; 2/1) under agitation to crystallize a product. This was filtered and collected and washing with 2-propanol and drying were conducted to obtain 0.19 g of that of structural formula 3-25.

(3-B) Manufacturing of Display Electrode, Electrochromic Display Layer, Opposing Electrode, and Electrochromic Display Device A display electrode, an electrochromic display layer, an opposing electrode, and an electrochromic display device were manufactured by a method similar to that of practical example 3-4.

(3-C) Color Development/Erasing Test

An evaluation of color development/erasing of the manufactured electrochromic display element was conducted similar to practical example 3-1.

Figure 27:
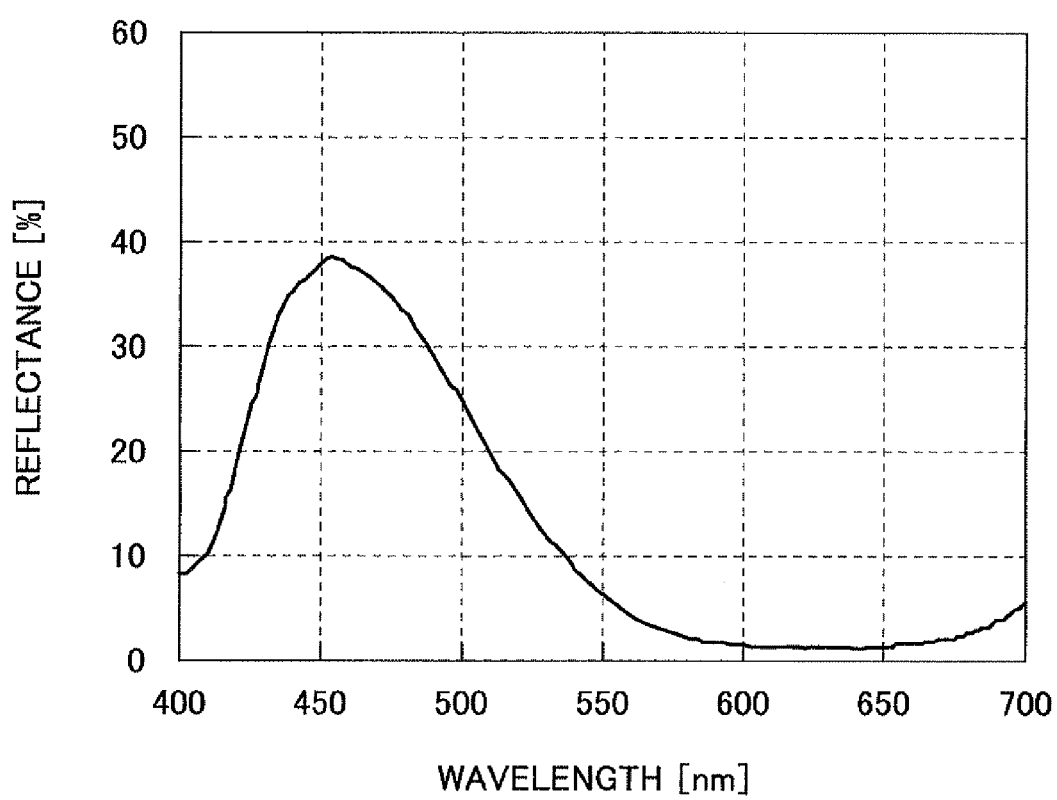
FIG. 27 is a graph illustrating a spectrum of an electrochromic display element manufactured in practical example 3-7 at the time of color development thereof.
Figure 28:
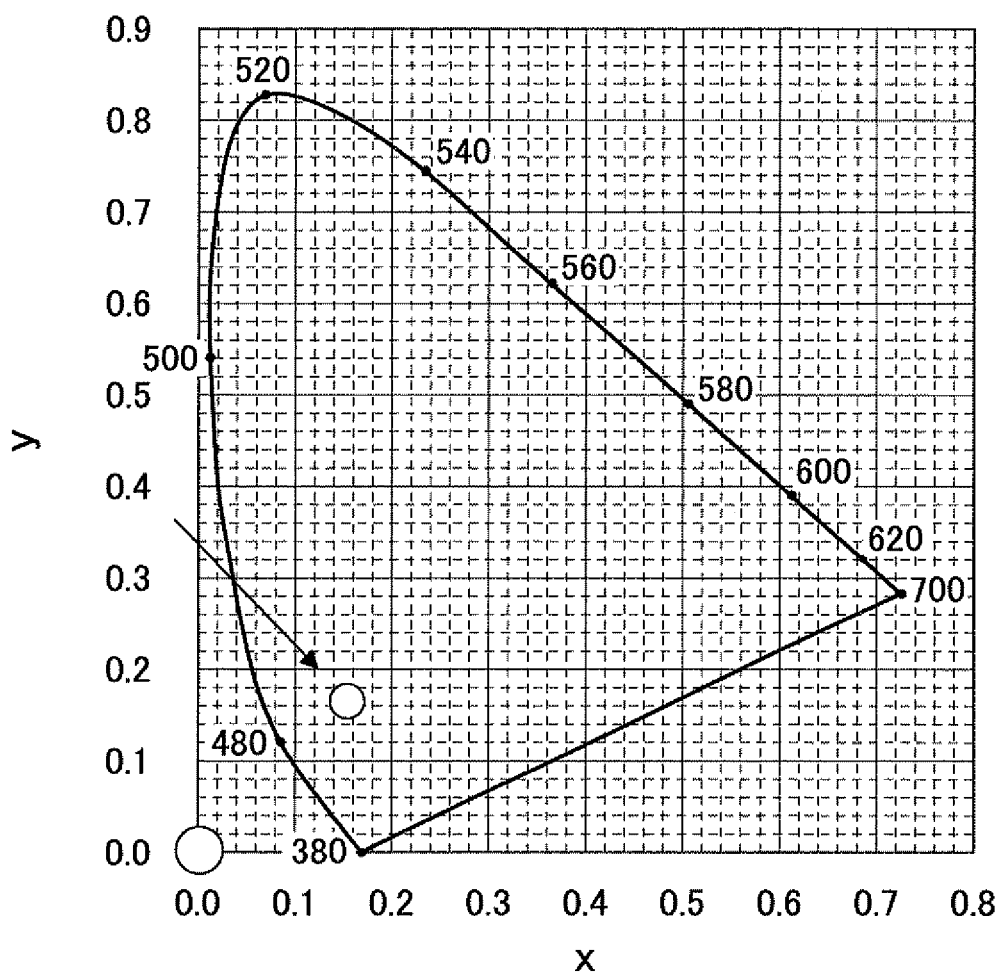
FIG. 28 is a graph illustrating a result of a coordinate transformation of a spectrum of an electrochromic display element manufactured in practical example 3-7 at the time of color development thereof into a CIE color specification system.

When a negative electrode and a positive electrode were connected to the display electrode and opposing electrode of the display element, respectively, and a voltage of 3.0 V was applied for 1 second, the display element provided cyan color development. Furthermore, when a reverse voltage of −3.0 V was applied for 1 second, color erasing was provided and a white color was recovered. FIG. 27 illustrates a reflection spectrum at the time of color development. Furthermore, FIG. 28 illustrates a result of a coordinate transformation of this spectrum into a CIE color specification system. From FIG. 27 and FIG. 28, it could be confirmed that a clear cyan color development was provided.

The display electrode on which the electrochromic display layer was formed was put in a quartz cell, and the inside of the cell was filled with an electrolyte liquid in which 20 wt % of tetrabutylammonium perchlorate was dissolved in dimethyl sulfoxide, while a platinum electrode as a counter electrode and a $Ag/Ag^+$ electrode RE-7 (produced by BAS Corporation) as a reference electrode were used. When this quartz cell was irradiated with deuterium tungsten halogen light (DH-2000 produced by Ocean Optics Inc.) and transmitted light was detected by a spectrometer (USB4000 produced by Ocean Optics Inc.), an absorption spectrum was measured.

Figure 29:
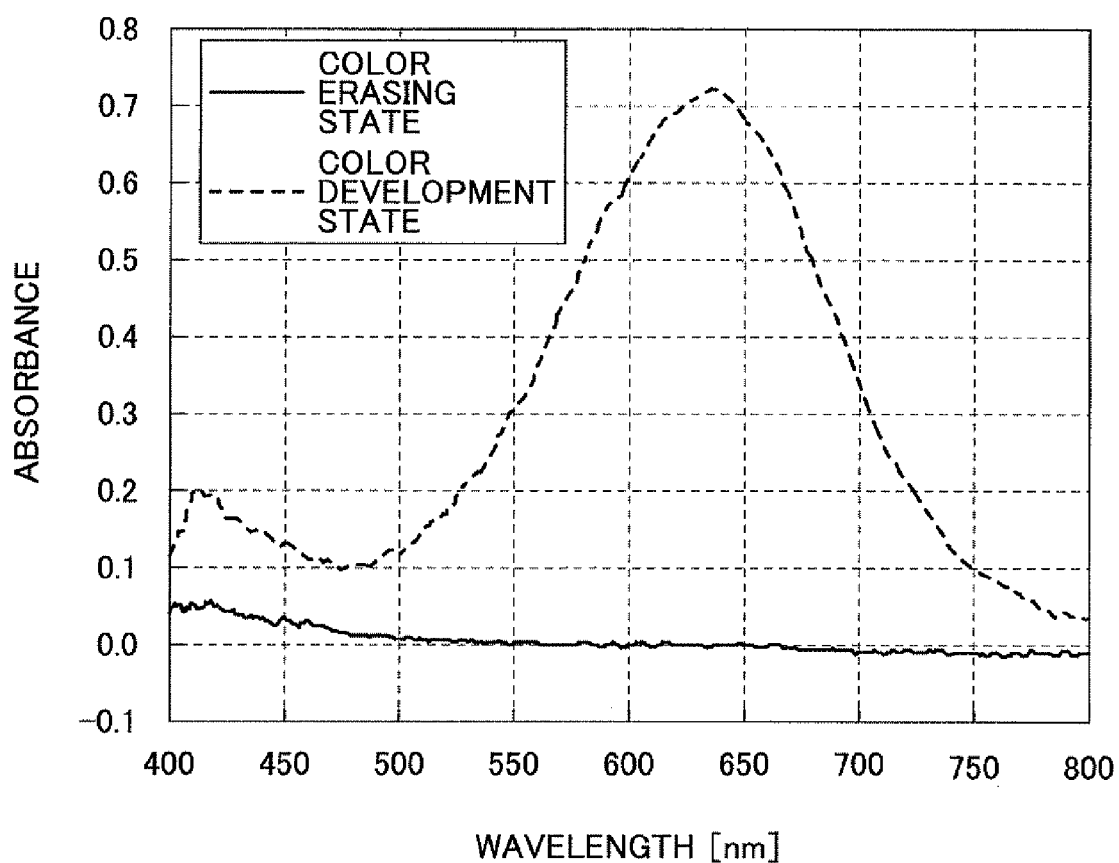
FIG. 29 is a graph illustrating an absorption spectrum of an electrochromic display layer manufactured in practical example 3-7 before and after application of a voltage thereto.

When a voltage of −1.5V was applied by using a potentiostat (ALS-660C produced by BAS Corporation), cyan color development was provided. FIG. 29 illustrates absorption spectra before and after application of a voltage.

Practical Example 3-8

(3-A) Synthesis of that of a Structural Formula 3-29

3.6 g of 2,3,5,6-tetrafluoro-p-xylene, 30 ml of carbon tetrachloride, 7.1 g of NBS, and 0.10 g of AIBN were charged into a 100 ml four-necked reactor and reaction was conducted at 70° C. for 17 hours. After completion of the reaction, standing to cool to room temperature was conducted. 10 g of activated white earth was added and agitation was conducted for processing. A reaction liquid was filtered and a residue was well washed with hexane. When a filtrate was concentrated, a coarse produce was obtained as a crystal. This coarse product was disintegrated and purified with methanol to obtain 3.8 g of 2,3,5,6-tetrafluoro-1,4-bis(bromomethyl)benzene.

2.0 g of 2,3,5,6-tetrafluoro-1,4-bis(bromomethyl)benzene and 2.2 g of triethyl phosphite were charged into a 50 ml of three-necked reactor and heating to and agitation at 110 to 120° C. were conducted. At this temperature, reaction was conducted for 2 hours. When standing to cool to room temperature was conducted, a solid was precipitated. Hexane was added and filtration was conducted. An obtained crystal was dried to obtain 2.4 g of 2,3,5,6-tetrafluoro-1,4-bis(diethylphosphonylmethyl)benzene.

2.3 g of 2,3,5,6-tetrafluoro-1,4-bis(diethylphosphonylmethyl)benzene, 20 ml of DMF (dewatered), and 1.2 g of 4-formylpyridine were charged into a 50 ml three-necked reactor. After substitution with nitrogen was conducted, 10 ml of a solution of 1.4 g of potassium t-butoxide in DMF was gently dropped thereto, and accordingly, changed to a red solution. Reaction was conducted at room temperature for 18 hours. A reaction liquid was discharged into water and extraction with chloroform was conduced. A reaction liquid was concentrated to obtain 0.97 g of a coarse product. The coarse product was purified by a silica gel column (toluene/acetone 1/1) and an obtained solid was disintegrated and purified with methanol to obtain 0.69 g of target substance.

When GC/MS measurement of this compound was conducted, a molecular ion peak was provided at M=356.

A flow of synthesis of such intermediate 29 is illustrated below.

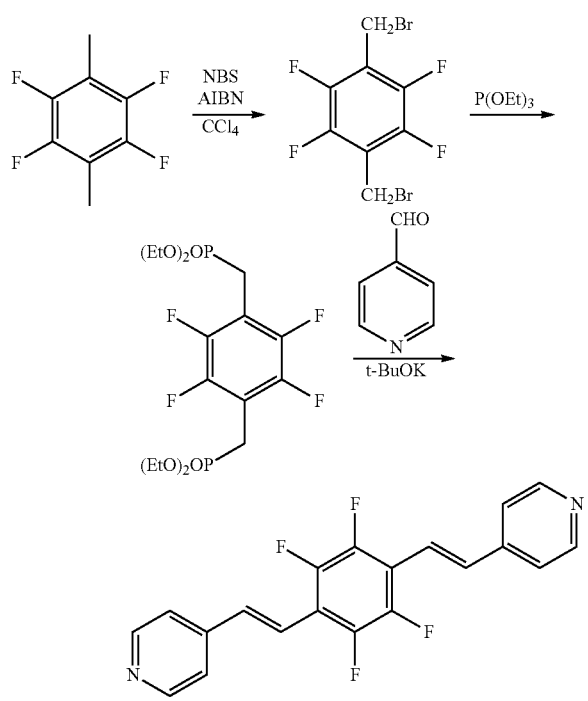

0.2 g of intermediate 3-29, 1.0 g of diethyl bromoethylphosphonate, 3 ml of 1-propanol, and 6 ml of water were charged and this mixture was agitated at 90° C. for 37 hours. After standing to cool, a reaction mixture was discharged into a mixed liquid of 15 ml of water and 30 ml of ethyl acetate and an aqueous layer was fractionated. After this aqueous layer was charged into a reaction flask, 10 ml of concentrated hydrochloric acid was added thereto and agitation was conducted at 90° C. for 22 hours. After standing to cool, water was distilled out from the reaction mixture under a reduced pressure, then a tar-like residue was dissolved in methanol, and this methanol solution was dropped into 2-propanol/ethanol (volume ratio; 2/1) under agitation to crystallize a product. This was filtered and collected and washing with 2-propanol and drying were conducted to obtain 0.14 g of that of structural formula 3-29.

(3-B) Manufacturing of Display Electrode, Electrochromic Display Layer, Opposing Electrode, and Electrochromic Display Device A display electrode, an electrochromic display layer, an opposing electrode, and an electrochromic display device were manufactured by using an intermediate 4-29 synthesized in (3-A) and a method similar to that of practical example 3-1.

(3-C) Color Development/Erasing Test

An evaluation of color development/erasing of the manufactured electrochromic display element was conducted similar to practical example 3-1.

When a negative electrode and a positive electrode were connected to the display electrode and opposing electrode of the display element, respectively, and a voltage of 3.0 V was applied for 1 second, the display element provided cyan color development. Furthermore, when a reverse voltage of −3.0 V was applied for 1 second, color erasing was provided and a white color was recovered.

Practical example 3-9

(3-A) Synthesis of that of a Structural Formula 3-45

2.3 g of 2,5-dimethylterephthalonitrile, 23 ml of carbon tetrachloride, 5.3 g of NBS, and 0.07 g of AIBN were charged into a 100 ml four-necked reactor and reaction was conducted at 75° C. for 1 hour. After completion of the reaction, standing to cool to room temperature was conducted. A reaction liquid was filtered and a residue was well washed with carbon tetrachloride. When a filtrate was concentrated, a coarse produce was obtained as an oil. Methanol was added to this coarse product to cause crystallization. This crystal was filtered and brought out to obtain 0.57 g of 1,4-dicyano-2,5-bis(bromomethyl)benzene.

0.55 g of 1,4-dicyano-2,5-bis(bromomethyl)benzene and 0.61 g of triethyl phosphite were charged into a 50 ml of three-necked reactor and heating to and agitation at 100 to 110° C. were conducted. At this temperature, reaction was conducted for 2 hours. Standing to cool to room temperature was conducted and purification with a silica gel column was conducted to obtain 0.45 g of 2,5-dicyano-1,4-bis(diethylphosphonylmethyl)benzene.

0.45 g of 2,5-dicyano-1,4-bis(diethylphosphonylmethyl)benzene, 15 ml of DMF (dewatered), and 0.28 g of 4-formylpyridine were charged into a 50 ml three-necked reactor. After substitution with nitrogen was conducted, 5 ml of a solution of 0.35 g of potassium t-butoxide in DMF was gently dropped thereto, and accordingly, changed to a green-brown solution. Reaction was conducted at 60° C. for 3 hours. A reaction liquid was discharged into water and extraction with chloroform was conduced. A reaction liquid was concentrated to obtain a coarse product. The coarse product was purified by a silica gel column (toluene/acetone 1/1) and an obtained solid was disintegrated and purified with methanol to obtain 0.08 g of intermediate 3-45.

A flow of synthesis of such intermediate 45 is illustrated below.

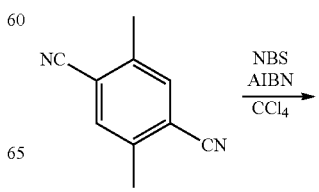

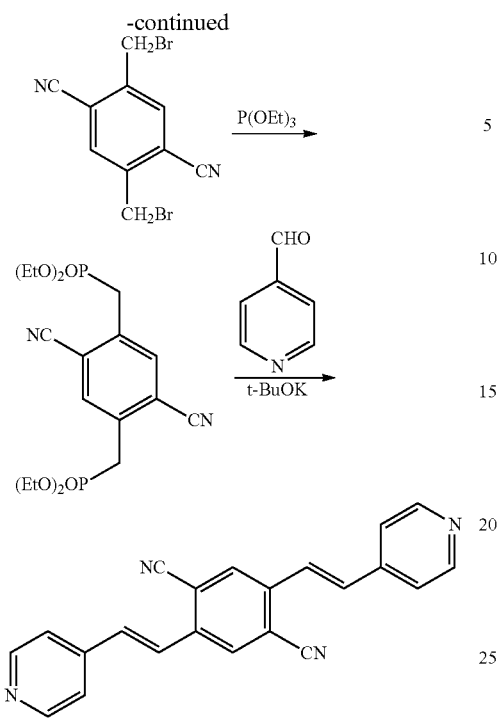

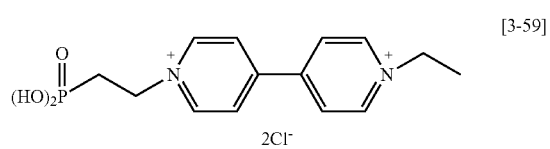

(3-B) Manufacturing of Display Electrode, Electrochromic Display Layer, Opposing Electrode, and Electrochromic Display Device A display electrode, an electrochromic display layer, an opposing electrode, and an electrochromic display device were manufactured by using an intermediate 4-45 synthesized in (3-A) and a method similar to that of practical example 3-1.

(3-C) Color Development/Erasing Test

An evaluation of color development/erasing of the manufactured electrochromic display element was conducted similar to practical example 3-1.

Figure 30:
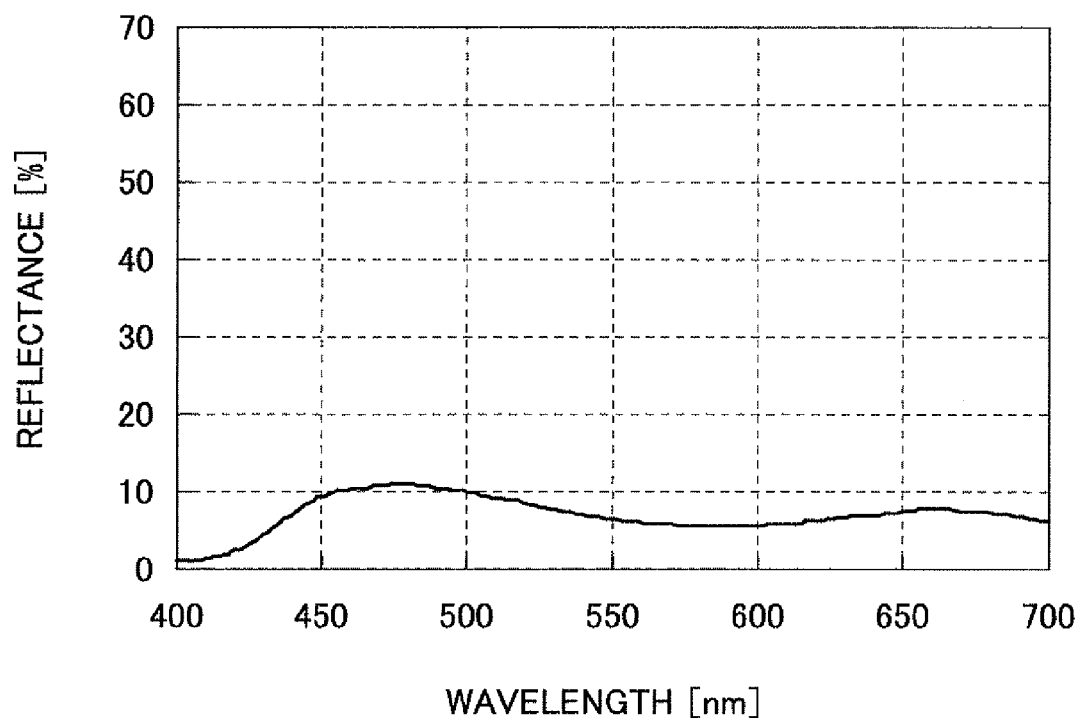
FIG. 30 is a graph illustrating a spectrum of an electrochromic display element manufactured in practical example 3-9 at the time of color development thereof.
Figure 31:
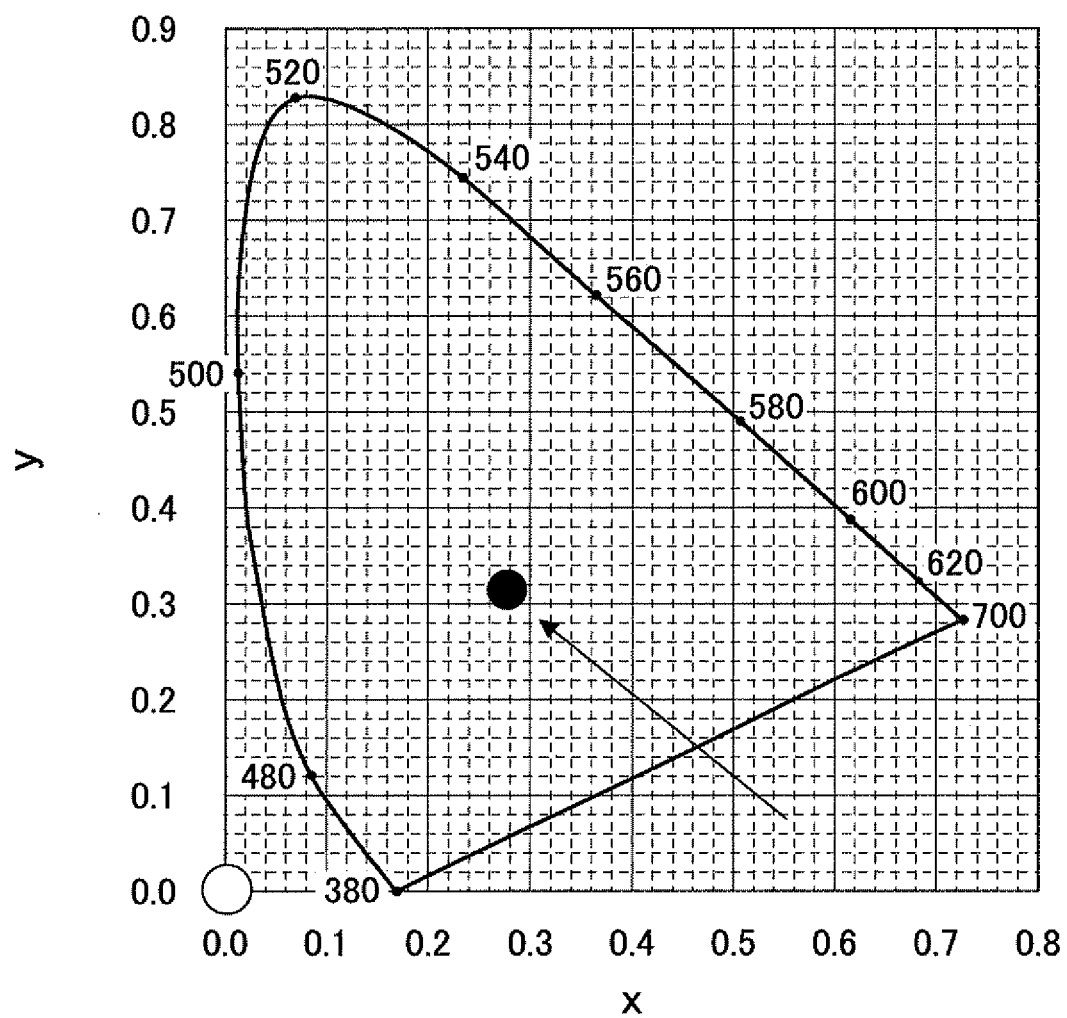
FIG. 31 is a graph illustrating a result of a coordinate transformation of a spectrum of an electrochromic display element manufactured in practical example 3-9 at the time of color development thereof into a CIE color specification system.

When a negative electrode and a positive electrode were connected to the display electrode and opposing electrode of the display element, respectively, and a voltage of 3.0 V was applied for 1 second, the display element provided black color development. Furthermore, when a reverse voltage of −3.0 V was applied for 1 second, color erasing was provided and a white color was recovered. FIG. 30 illustrates a reflection spectrum at the time of color development. Furthermore, FIG. 31 illustrates a result of a coordinate transformation of this spectrum into a CIE color specification system. From FIG. 30 and FIG. 31, it could be confirmed that a clear black color development was provided.

The display electrode on which the electrochromic display layer was formed was put in a quartz cell, and the inside of the cell was filled with an electrolyte liquid in which 20 wt % of tetrabutylammonium perchlorate was dissolved in dimethyl sulfoxide, while a platinum electrode as a counter electrode and a Ag/Ag$^+$ electrode RE-7 (produced by BAS Corporation) as a reference electrode were used. When this quartz cell was irradiated with deuterium tungsten halogen light (DH-2000 produced by Ocean Optics Inc.) and transmitted light was detected by a spectrometer (USB4000 produced by Ocean Optics Inc.), an absorption spectrum was measured.

Figure 32:
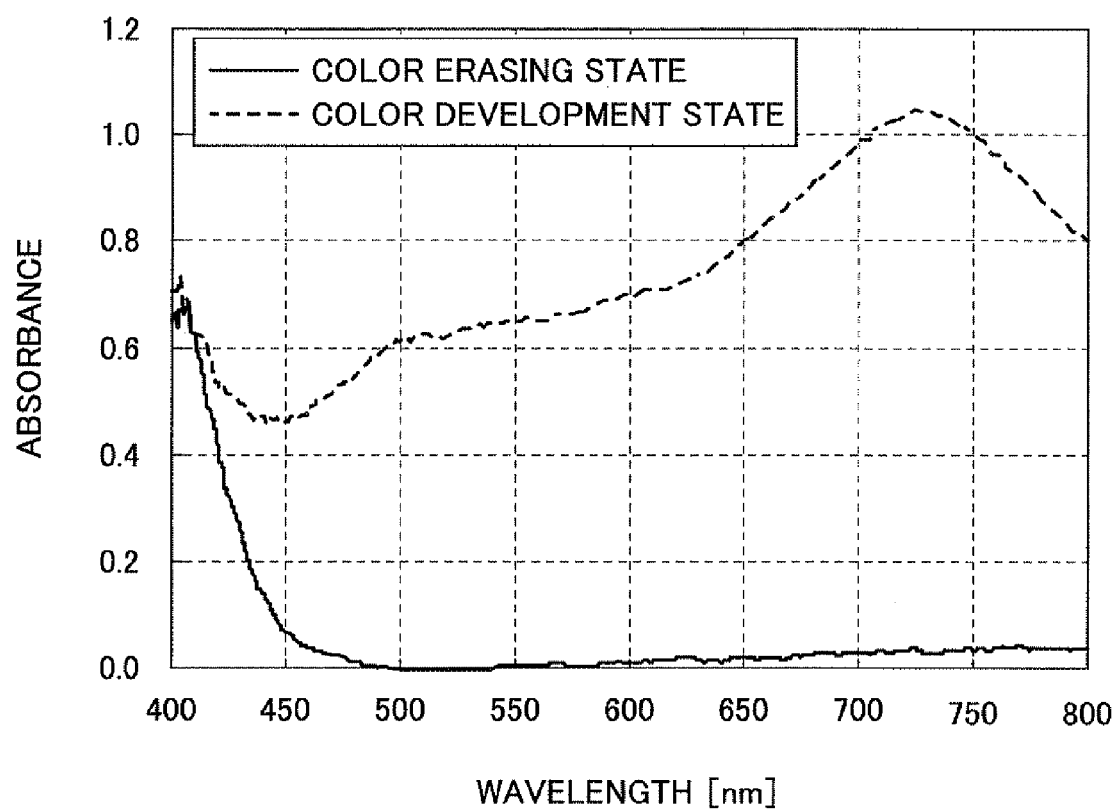
FIG. 32 is a graph illustrating an absorption spectrum of an electrochromic display layer manufactured in practical example 3-9 before and after application of a voltage thereto.

When a voltage of −1.5V was applied by using a potentiostat (ALS-660C produced by BAS Corporation), black color development was provided. FIG. 32 illustrates absorption spectra before and after application of a voltage.

Comparative Example 3-1

A display element for a comparative example was manufactured similarly to practical example 3-1 except that the compound used in practical example 3-1 was replaced with a viologen compound represented by the following structural formula (3-59) which is a publicly known electrochromic compound, and evaluated similarly.

When a negative electrode and a positive electrode were connected to the display electrode 1 and opposing electrode 2 of the display element, respectively, and a voltage of 3.0 V was applied for 1 second, the display element provided blue color development. Furthermore, when a reverse voltage of −4.5 V was applied for 2 seconds, complete color erasing was provided and a white color was recovered.

Figure 33:
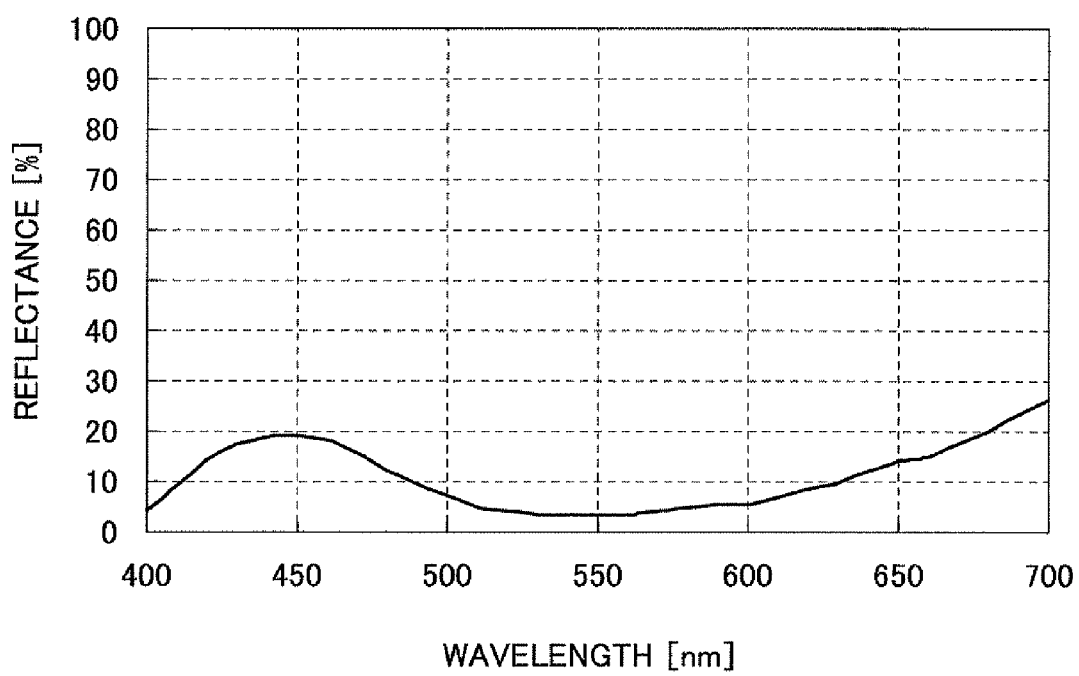
FIG. 33 is a graph illustrating a spectrum of an electrochromic display element manufactured in comparative example 3-1 at the time of color development thereof.

Moreover, FIG. 33 illustrates a reflection spectrum at a color development state of the display element in comparative example 3-1. As is clear from the spectrum, the width of a low reflectance region of comparative example 3-1 in FIG. 33 in the visible region was broad and broad light absorption was provided. As a result, blue color development was provided.

Practical Example 4-1

(4-A) Electrochromic Compound 4-4: Synthesis of that of Chemical Formula 4-4

1) Synthesis of Intermediate 4-4-1

After 0.57 g of 1-phenylpyrrole and 20 ml of THF were charged into a reaction flask, this mixture was cooled at −70° C. or less in a dry ice/acetone bath and 1.4 g of N-bromosuccinimide (NBS) was gently thrown thereto at −73° C. to −68° C. under agitation. After completion of throwing, the dry ice/acetone bath was removed and agitation was continued so that the liquid temperature of a reaction mixture was −20° C. After the agitation was stopped, the reaction mixture was put in a refrigerator set at −10° C. and left at rest for 21 hours to cause reaction. After completion of the reaction, the reaction mixture was diluted with water, then a product was extracted with hexane, and hexane was distilled out to obtain 1.3 g of intermediate 4-4-1.

2) Synthesis of Intermediate 4-4-2

1.3 g of intermediate 4-4-1, 1.0 g of 4-pyridineboronic acid, 1.3 g of sodium carbonate, 15 ml of 1,4-dioxane, and 5 ml of water were charged into a reaction flask and the inside of the reaction flask was replaced with argon. 0.28 g of dichlorobis(triphenylphosphine)palladium(II) was added thereto and agitation was conducted at 80 to 90° C. for 22 hours. After standing to cool, the reaction mixture was discharged into a mixture of water and chloroform, and treatment with activated carbon, fractionation of a chloroform layer, drying with anhydrous sodium sulfate, and distillation-out of chloroform were conducted. An obtained brown solid was disintegrated with toluene/hexane, and filtration collection and drying were conducted to obtain 0.34 g of intermediate 4-4-2. GC/MS measurement for the same was conducted and a molecular ion peak was provided at M=297.

3) Synthesis of Compound 4-4

0.2 g of intermediate 4-4-2, 1.0 g of diethyl bromoethylphosphonate, 3 ml of 1-propanol, and 6 ml of water were charged into a reaction flask and this mixture was agitated at 90° C. for 40 hours. After standing to cool, a reaction mixture was discharged into a mixed liquid of 15 ml of water and 30 ml of ethyl acetate and an aqueous layer was fractionated. After this aqueous layer was charged into a reaction flask, 10 ml of concentrated hydrochloric acid was added thereto and agitation was conducted at 90° C. for 23 hours. After standing to cool, water was distilled out from the reaction mixture under a reduced pressure, then a tar-like residue was dissolved in methanol, and this methanol solution was dropped into 2-propanol/ethanol (volume ratio; 2/1) under agitation to crystallize a product. This was filtered and collected and washing with 2-propanol and drying were conducted to obtain 0.15 g of a compound represented by formula 4-4 as described above.

A flow of the above-mentioned synthesis of a compound represented by chemical formula 4-4 will be described below.

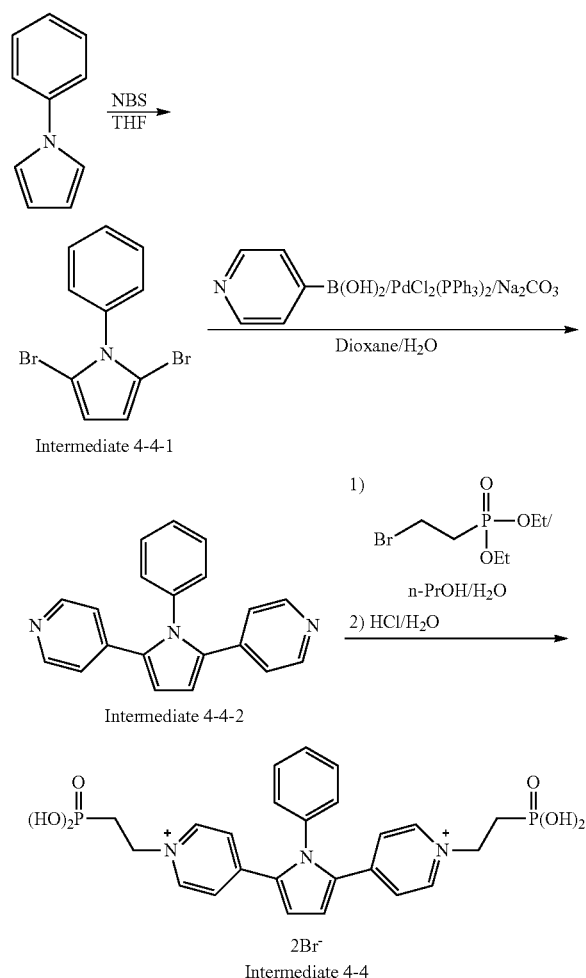

(4-B) Formation of Display Electrode and Electrochromic Display Layer

First, a 30 mm×30 mm glass substrate was prepared and an ITO film with a thickness of about 100 nm was formed on a 16 mm×23 mm area on its top surface by a sputter method to form a display electrode 1. The sheet resistance of this display electrode 1 between end portions of the electrode was measured and was about 200 Ω.

Then, dispersion liquid SP210 (produced by Showa Titanium Corporation) of titanium oxide nano-particles was applied by a spin-coat method onto the glass substrate on which the display electrode 1 was formed and annealing was conducted at 120° C. for 15 minutes to form a titanium oxide particle film, and subsequently a 1 wt % solution of a compound represented by chemical formula 4-4 in 2,2,3,3-tetrafluoropropanol was applied as a coating liquid by a spin-coat method, and annealing was conducted at 120° C. for 10 minutes to form a display layer 4 in which an electrochromic compound is adsorbed on a surface of a titanium oxide particle.

(4-C) Formation of Opposing Electrode

Meanwhile, a 30 mm×30 mm glass substrate other than the previous glass substrate was prepared and an ITO film with a thickness of about 150 nm was formed on the entire of its top surface by a sputter method to form an opposing electrode 2. Furthermore, a solution prepared by adding 25 wt % of 2-ethoxyethyl acetate into a thermosetting electrically conductive carbon ink (CH10 produced by Jujo Chemical Corporation) was applied by a spin-coat method onto the top surface of a glass substrate in which a transparent electrically conductive thin film was formed on the entire surface thereof, and annealing was conducted at 120° C. for 15 minutes to form an opposing electrode 2.

(4-D) Manufacturing of Electrochromic Display Device

The display substrate 1 and the opposing substrate 2 were bonded via a 75 μm spacer to manufacture a cell. Then, 35 wt % of titanium oxide particles with an average primary particle diameter of 300 nm (CR50 produced by Ishihara Sangyo Kaisha, Ltd.) were dispersed in a solution in which 20 wt % of tetrabutylammonium perchlorate was dissolved in dimethyl sulfoxide to prepare an electrolyte solution and it was enclosed in a cell to manufacture an electrochromic display element.

Comparative Example 4-1

A compound represented by the following chemical formula 4-11 was synthesized which is disclosed in Japanese Patent Application Publication No. 2007-241238.

[4-11]

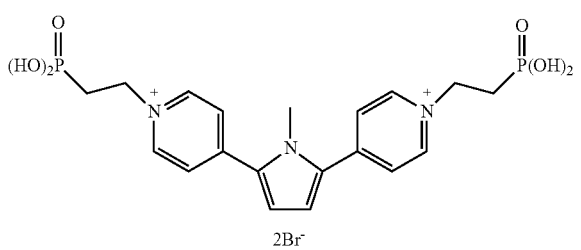

Then, a display electrode, an electrochromic display layer, and an electrochromic display device were manufactured by a method identical to (B) to (D) of practical example 4-1.

(4-E) Color Development/Erasing Test

A comparative evaluation of color development/erasing of the electrochromic display element manufactured in practical example 4-1 and electrochromic display element manufactured in comparative example 4-1 was conducted.

The evaluation of color development/erasing was conducted by diffused light irradiation using a spectrophotometric colorimeter LCD-5000 produced by Otsuka Electronics Co., Ltd.

The electrochromic display element in comparative example 4-1 exhibited yellow color at a color erasing state before application of a voltage. In comparison to this one, the electrochromic display element according to the present invention in practical example 4-1 apparently exhibited less coloring and its color is like a white color.

When a negative electrode and a positive electrode were connected to display electrode 1 and opposing electrode 2 of each display element, respectively, and a voltage of 3.0 V was applied for 1 second, both display elements provided good magenta color development.

Figure 34:
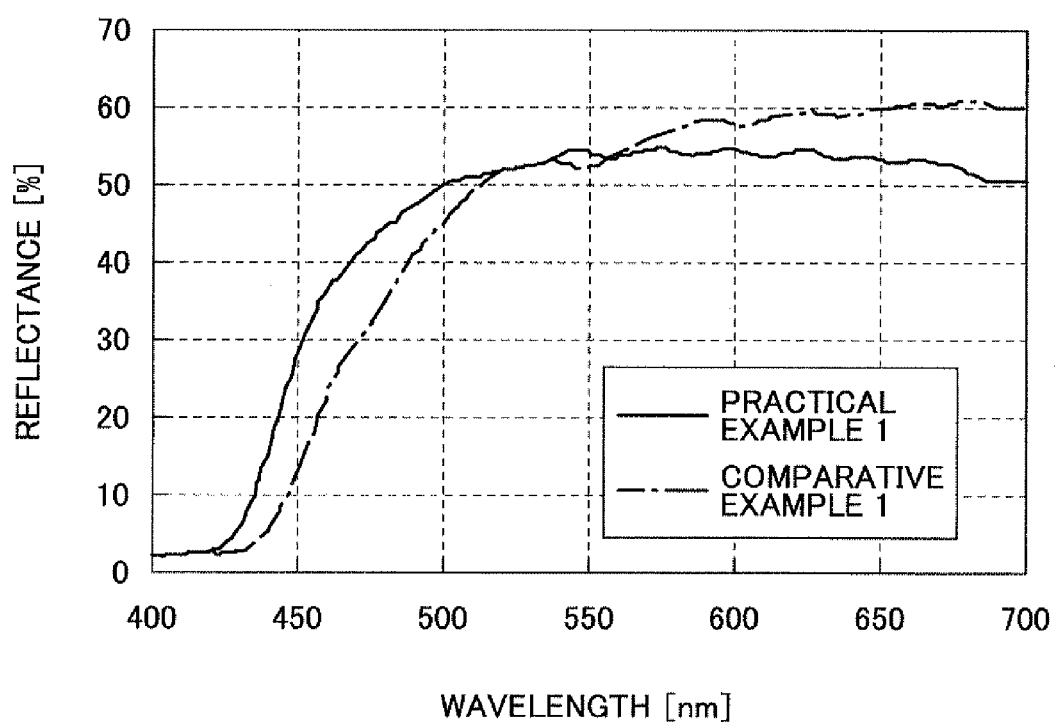
FIG. 34 is a graph illustrating spectra of electrochromic display elements manufactured in practical example 4-1 and comparative example 4-1 at the time of color erasing thereof.
Figure 35:
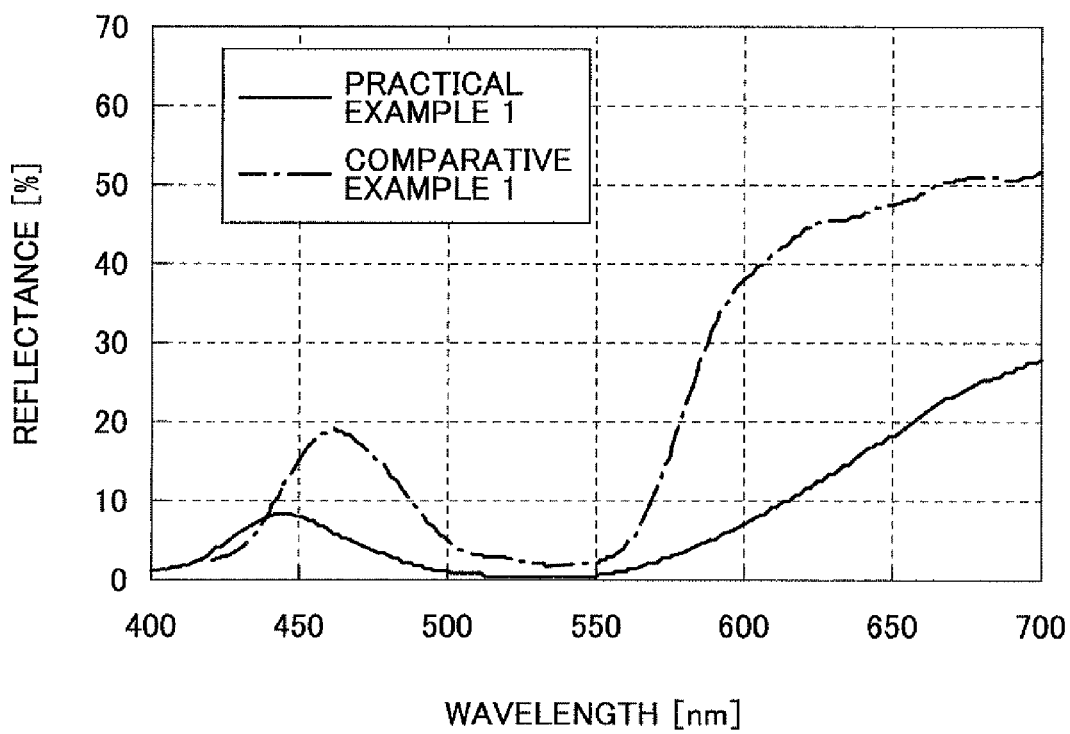
FIG. 35 is a graph illustrating spectra of electrochromic display elements manufactured in practical example 4-1 and comparative example 4-1 at the time of color development thereof.
Figure 36:
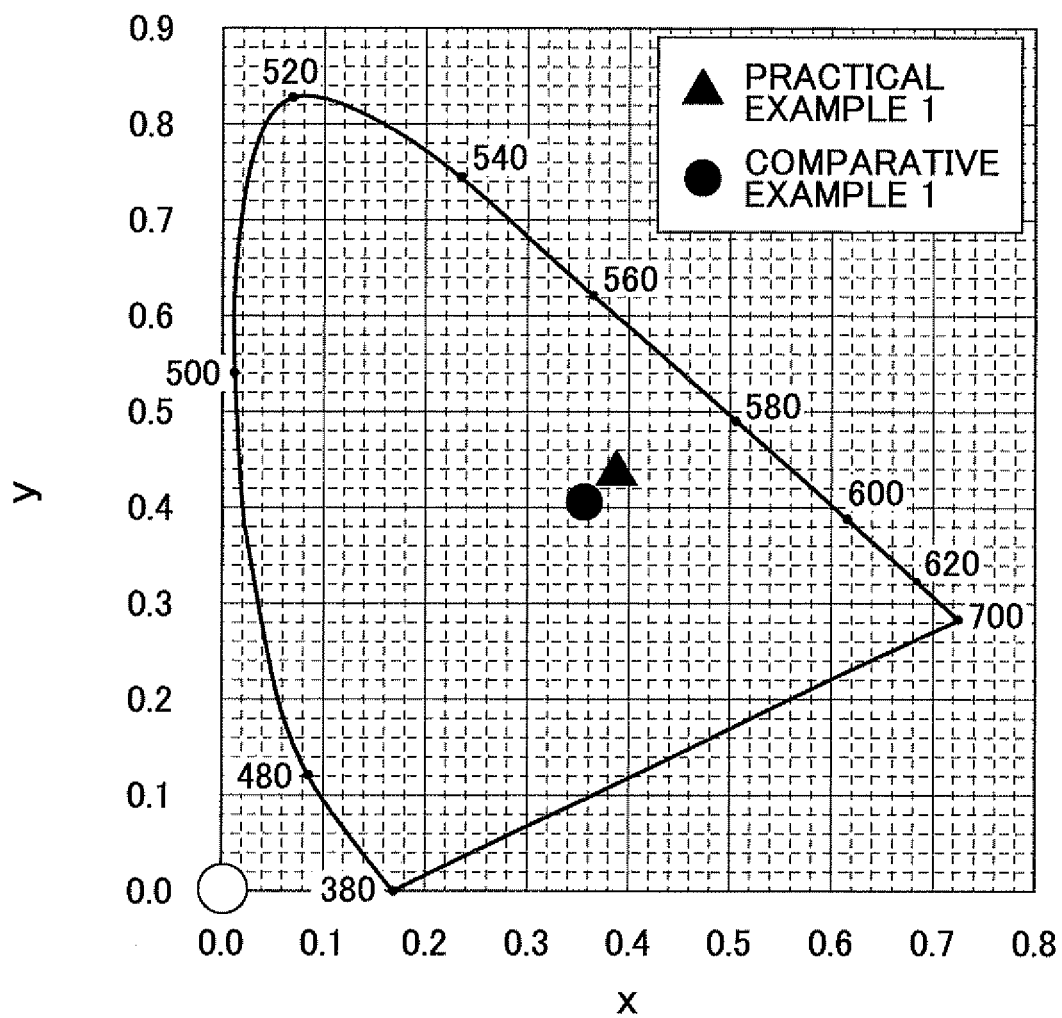
FIG. 36 is a graph illustrating a result of a coordinate transformation of spectra of electrochromic display elements manufactured in practical example 4-1 and comparative example 4-1 at the time of color erasing thereof into a CIE color specification system.
Figure 37:
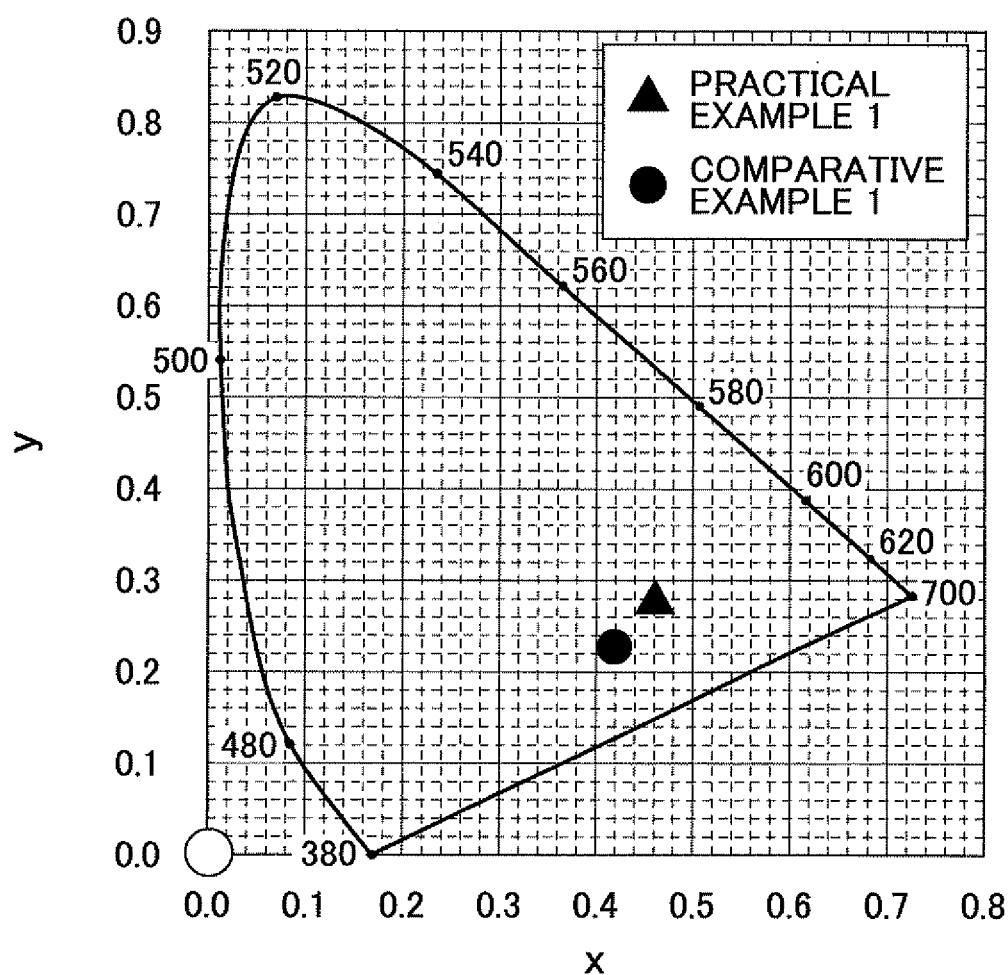
FIG. 37 is a graph illustrating a result of a coordinate transformation of spectra of electrochromic display elements manufactured in practical example 4-1 and comparative example 4-1 at the time of color development thereof into a CIE color specification system.

FIG. 34 illustrates a reflection spectrum at the time of color erasing. Furthermore, FIG. 35 illustrates a reflection spectrum at the time of color development. Moreover, FIG. 36 and FIG. 37 illustrate results of a coordinate transformation of these spectra into a CIE color specification system.

From FIG. 34, FIG. 35, FIG. 36, and FIG. 37, it could be confirmed that the electrochromic compound in practical example 4-1 exhibited less coloring at the time of color erasing than the structure of comparative example 4-1 and provided clear magenta color development at the time of color development.

Furthermore, a color development state in practical example 4-1 was retained after application of a color development voltage (3.0 V, 1 second) and at 300 seconds after power-off. That is, it was possible to provide magenta color development and further a very excellent image retention characteristic in practical example 4-1.

The display electrode on which the electrochromic display layer manufactured in each of practical example 4-1 and comparative example 4-1 was formed was put in a quartz cell, and the inside of the cell was filled with an electrolyte liquid in which 20 wt % of tetrabutylammonium perchlorate was dissolved in dimethyl sulfoxide (DMSO), while a platinum electrode as a counter electrode and a Ag/Ag$^+$ electrode RE-7 (produced by BAS Corporation) as a reference electrode were used. When this quartz cell was irradiated with deuterium tungsten halogen light (DH-2000 produced by Ocean Optics Inc.) and transmitted light was detected by a spectrometer (USB4000 produced by Ocean Optics Inc.), an absorption spectrum was measured.

Figure 38:
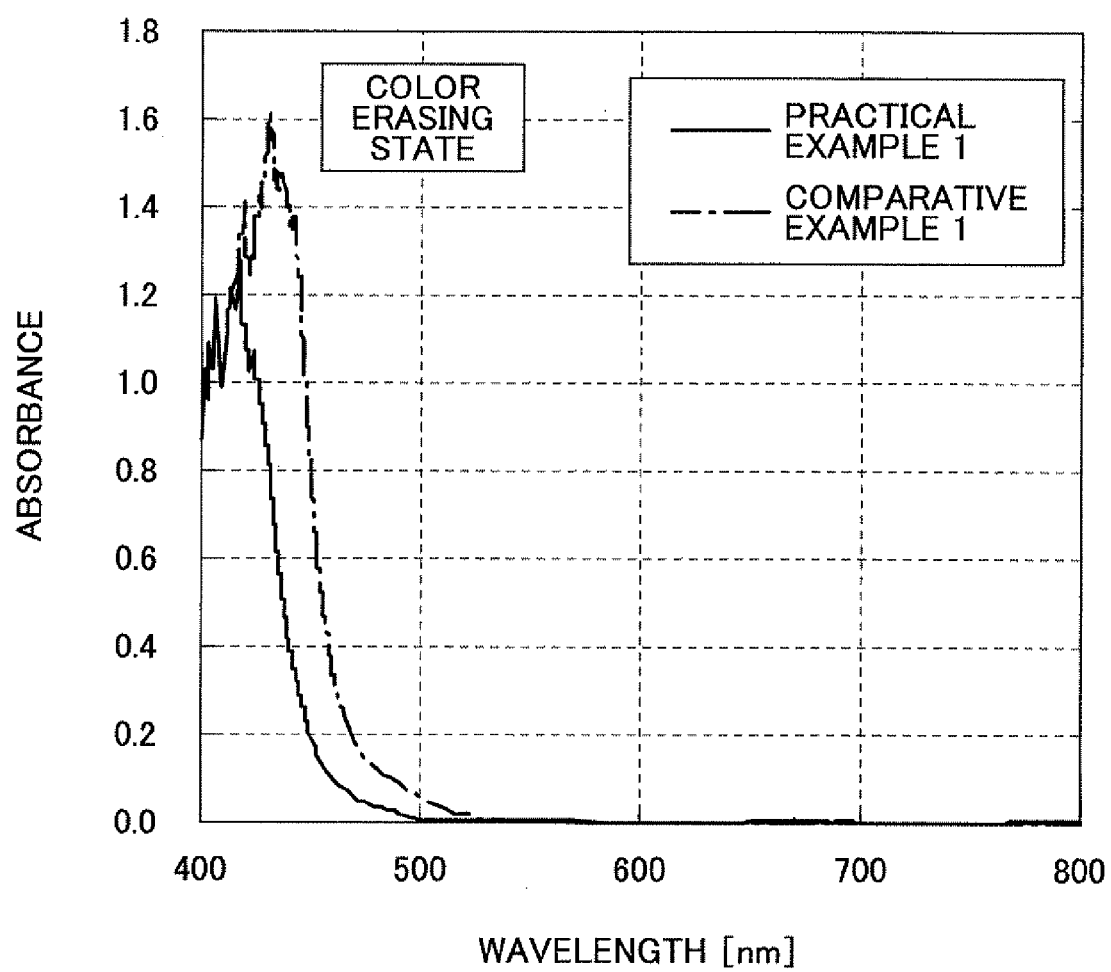
FIG. 38 is a diagram illustrating absorption spectra of electrochromic display layers manufactured in practical example 4-1 and comparative example 4-1 before application of a voltage thereto.
Figure 39:
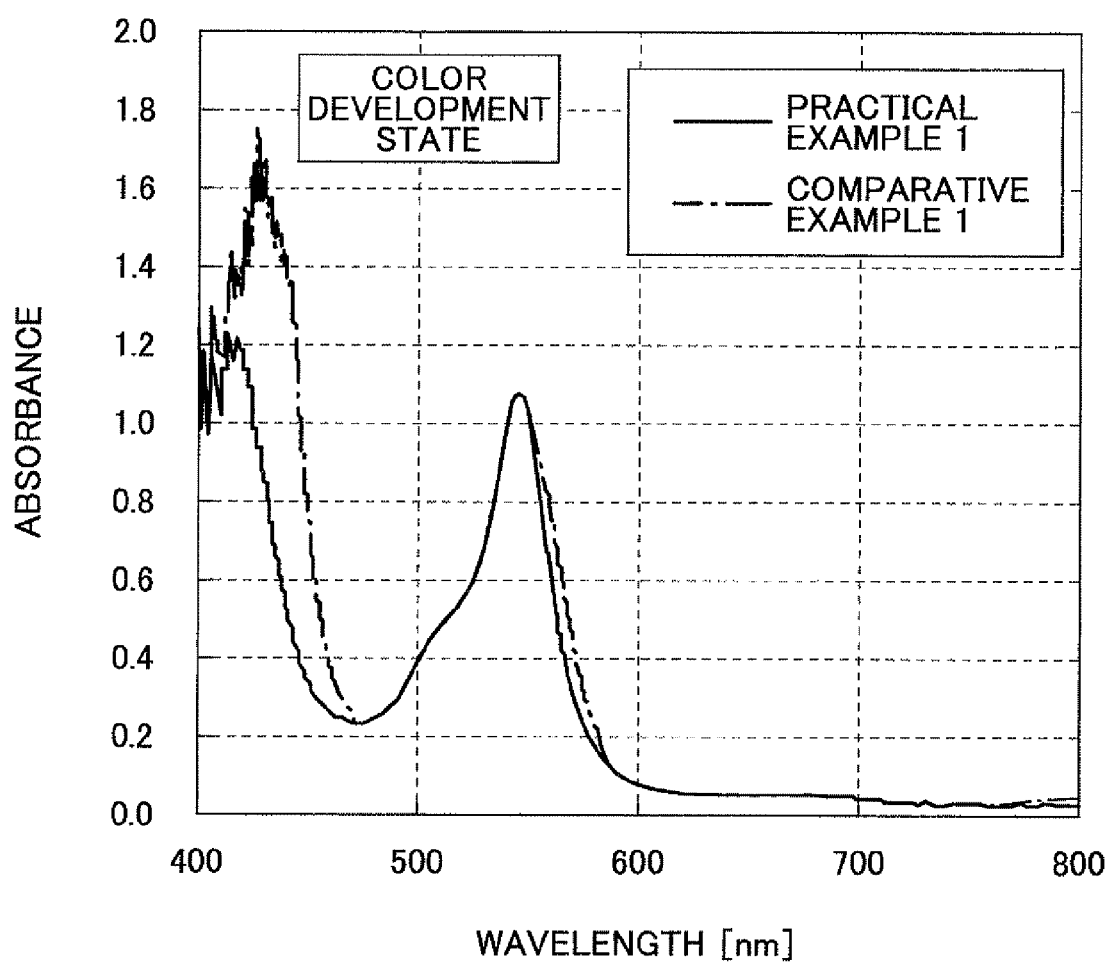
FIG. 39 is a diagram illustrating absorption spectra of electrochromic display layers manufactured in practical example 4-1 and comparative example 4-1 after application of a voltage thereto.

FIG. 38 illustrates an absorption spectrum at a color erasing state before application of a voltage. It is found that an absorption band of the electrochromic display layer in practical example 4-1 was present at only 500 nm or less whereas an absorption band of the electrochromic display layer in practical example 4-1 extended to about 550 nm. Furthermore, it is also found that the electrochromic display layer in comparative example 4-1 had a higher absorbance from 400 nm to 500 nm and coloring at the time of color erasing was considerably different. When a voltage of −1.5V was applied by using a potentiostat (ALS-660C produced by BAS Corporation), a maximum absorption wavelength was 550 nm (FIG. 39) and magenta color development was provided.

Practical Example 4-2

(A) Electrochromic Compound 10: Synthesis of Intermediate 4-10 of the Chemical Formula (4-10)

1) Synthesis of Intermediate 4-10-1

After 10 ml of a 1 mol/L solution of zinc chloride in ether, 0.36 g of diethylamine, 0.35 g of tert-butylalcohol, and 7.5 ml of toluene were charged into a reaction flask and the inside of the reaction flask was substituted with nitrogen, this mixture was agitated at room temperature for 1.5 hours. Then, 1.4 g of 2-bromo-1-(4-bromophenyl)ethanone and 1.5 g of 4'-bromoacetophenone were added thereto, and agitation was conducted at room temperature for 42 hours. A crystal precipitated by discharging a reaction mixture into water and making it weak-acidic with a diluted sulfuric acid was filtered, collected, washed with toluene and then methanol/water, and subsequently dried to obtain 0.67 g of intermediate 4-10-1.

2) Synthesis of Intermediate 4-10-1.

1.0 g of intermediate 4-10-1, 0.5 g of aniline, and 13 ml of acetic acid were charged into a reaction flask and this mixture was agitated at 80° C. for 12 hours. After standing to cool, a precipitated crystal was filtered, collected, washed with acetone, and dried to obtain 0.92 g of intermediate 4-10-2.

3) Synthesis of Intermediate 4-10-1

0.90 g of intermediate 4-10-2, 0.56 g of 4-pyridineboronic acid, 0.63 g of sodium carbonate, 14 ml of 1,4-dioxane, and 4 ml of water were charged into a reaction flask and the inside of the reaction flask was substituted with argon. 0.14 g of dichlorobis(triphenylphosphine)palladium (II) was added thereto and agitation was conducted at 80 to 90° C. for 4 hours. After standing to cool, a reaction mixture was discharged into a mixture of water and chloroform and treated with activated carbon, fractionation of a chloroform layer and drying with anhydrous sodium sulfate were conducted and subsequently chloroform was distilled out. An obtained solid was purified by silica gel column chromatography with an eluent of toluene/acetone (volume ratio; 4/1) to obtain 0.32 g of intermediate 4-10. When this LC/MS measurement was conducted, a molecular ion peak was provided at M=450.

A flow of synthesis of the above-mentioned intermediate 4-10 will be described below.

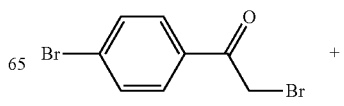

-continued

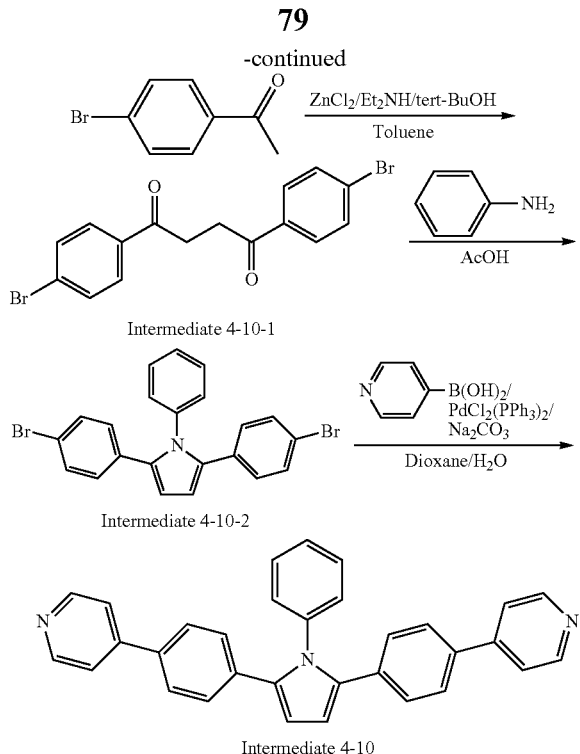

Intermediate 4-10-1

Intermediate 4-10-2

Intermediate 4-10

(4-B) Formation of Display Electrode and Electrochromic Display Layer

A dispersion liquid (SP210 produced by Showa Titanium Corporation) of titanium oxide nano-particles was applied by a spin-coat method onto a part of a 30 mm×30 mm glass substrate with FTO and annealing was conducted at 120° C. for 15 minutes to form a titanium oxide particle film. The thickness of the titanium oxide film was about 1.5 μm.

A 0.2 wt % solution of 3-bromopropyltrichlorosilane in toluene was prepared and the glass substrate with FTO on which the above-mentioned titanium oxide film was applied was dipped therein for 30 minutes, whereby 3-bromopropylsilane was bonded to a surface of the titanium oxide film. After a 1 wt % solution of intermediate 4-10 of chemical formula 4-10 synthesized in (4-A) in toluene was prepared and the above-mentioned substrate was dipped therein, reflux was conducted at 120° C. for 2 hours to react intermediate 4-10 with 3-bromopropylsilane.

(4-C) Manufacturing of Electrochromic Display Device

An opposing electrode and an electrochromic display device were manufactured by a method similar to that of practical example 4-1.

(4-D) Color Development/Erasing Test

An evaluation of color development/erasing of the manufactured electrochromic display element was conducted similar to practical example 4-1.

When a negative electrode and a positive electrode were connected to the display electrode and opposing electrode of the display element, respectively, and a voltage of 3.0 V was applied for 1 second, the display element provided magenta color development. Furthermore, when a reverse voltage of −2.0 V was applied for 1 second, a white color was recovered.

Practical Example 4-3

Two equivalent of ethyl bromide was reacted with intermediate 4-4-2 synthesized in practical example 4-1 whereby electrochromic compound 4-2 was synthesized. Then, a solution of water/2,2,3,3-tetrafluoropropanol (10 wt %) was prepared and 1 wt % of electrochromic compound 4-2 was dissolved therein to provide an electrochromic compound solution. 50 wt % of the electrochromic compound solution was added into an electrolyte liquid in which 20 wt % of tetrabutylammonium perchlorate was dissolved in dimethyl sulfoxide, and 30 mm×30 mm glass substrates with an electrically conductive film made of $SnO_2$ (produced by AGC Fabritech Co., Ltd.) as a display substrate and an opposing substrate were bonded via a 75 μm spacer and enclosed in a cell, whereby an electrochromic display element 10 was manufactured.

When a voltage of 2.5 V was applied to the manufactured display element for 2 seconds, the display element provided magenta color development. Furthermore, when a reverse voltage of −1.5 V was applied for 1 second, color erasing was provided and a transparency was recovered.

APPENDIX

Embodiment (1)

An electrochromic compound represented by a general formula of

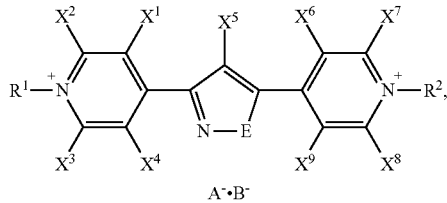

wherein
each $X^1$, $X^2$, $X^3$, $X^4$, $X^5$, $X^6$, $X^7$, $X^8$, and $X^9$ is independently a hydrogen atom, a halogen group, a hydroxyl group, a nitro group, a cyano group, a carboxyl group, a substituted or non-substituted alkoxycarbonyl group, a substituted or non-substituted aryloxycarbonyl group, a substituted or non-substituted alkylcarbonyl group, a substituted or non-substituted arylcarbonyl group, an aminocarbonyl group, a substituted or non-substituted monoalkylaminocarbonyl group, a substituted or non-substituted dialkylaminocarbonyl group, a substituted or non-substituted monoarylaminocarbonyl group, a substituted or non-substituted diarylaminocarbonyl group, a sulfonate group, a substituted or non-substituted alkoxysulfonyl group, a substituted or non-substituted aryloxysulfonyl group, a substituted or non-substituted alkylsulfonyl group, a substituted or non-substituted arylsulfonyl group, an aminosulfonyl group, a substituted or non-substituted monoalkylaminosulfonyl group, a substituted or non-substituted dialkylaminosulfonyl group, a substituted or non-substituted monoarylaminosulfonyl group, a substituted or non-substituted diarylaminosulfonyl group, an amino group, a substituted or non-substituted monoalkylamino group, a substituted or non-substituted dialkylamino group, a substituted or non-substituted alkyl group, a substituted or non-substituted alkenyl group, a substituted or non-substituted alkynyl group, a substituted or non-substituted aryl group, a substituted or non-substituted alkoxy group, a substituted or non-substituted aryloxy group, a substituted or non-substituted alkylthio group, a substituted or non-substituted arylthio group, or a substituted or non-substituted heterocyclic group, each of $R^1$ and $R^2$ is independently a substituted or non-substituted alkyl group, a substituted or non-substituted alkenyl group, a substituted or non-substituted alkynyl group, or a substituted or non-substituted aryl group, E is an oxy group, a thio group, or a seleno group, each of $A^-$ and $B^-$ is independently a monovalent anion, and $R^1$ and/or $R^2$ may be substituted with one or more kinds of functional groups selected from the group consisting of a sulfonate group, a phosphonate group, a phosphate group, and a carboxyl group.

Embodiment (2)

The electrochromic compound as described in embodiment (1), wherein each of $R^1$ and $R^2$ is independently a substituted or non-substituted alkyl group with a carbon number of 2 or more and 20 or less or a substituted or non-substituted aryl group.

Embodiment (3)

An electrochromic composition, comprising the electrochromic compound as described in embodiment (I) being bonded or adsorbed to an electrically conductive or semi-conductive nano-structure.

Embodiment (4)

Art electrochromic composition obtained by reacting with an electrically conductive or semi-conductive nano-structure a compound represented by a general formula of

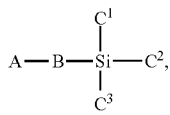

wherein

A is a halogen group,

B is an alkylene group, $C^1$ is a halogen group or an alkoxy group, and each of $C^2$ and $C^3$ is independently a halogen group, an alkoxy group, or an alkyl group, and subsequently reacting therewith a compound represented by a general formula of

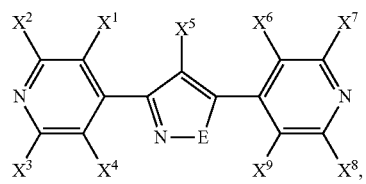

wherein each of $X^1$, $X^2$, $X^3$, $X^4$, $X^5$, $X^6$, $X^7$, $X^8$, and $X^9$ is independently a hydrogen atom, a halogen group, a hydroxyl group, a nitro group, a cyano group, a carboxyl group, a substituted or non-substituted alkoxycarbonyl group, a substituted or non-substituted aryloxycarbonyl group, a substituted or non-substituted alkylcarbonyl group, a substituted or non-substituted arylcarbonyl group, an aminocarbonyl group, a substituted or non-substituted monoalkylaminocarbonyl group, a substituted or non-substituted dialkylaminocarbonyl group, a substituted or non-substituted monoarylaminocarbonyl group, a substituted or non-substituted diarylaminocarbonyl group, a sulfonate group, a substituted or non-substituted alkoxysulfonyl group, a substituted or non-substituted aryloxysulfonyl group, a substituted or non-substituted alkylsulfonyl group, a substituted or non-substituted arylsulfonyl group, an aminosulfonyl group, a substituted or non-substituted monoalkylaminosulfonyl group, a substituted or non-substituted dialkylaminosulfonyl group, a substituted or non-substituted monoarylaminosulfonyl group, a substituted or non-substituted diarylaminosulfonyl group, an amino group, a substituted or non-substituted monoalkylamino group, a substituted or non-substituted dialkylamino group, a substituted or non-substituted alkyl group, a substituted or non-substituted alkenyl group, a substituted or non-substituted alkynyl group, a substituted or non-substituted aryl group, a substituted or non-substituted alkoxy group, a substituted or non-substituted aryloxy group, a substituted or non-substituted alkylthio group, a substituted or non-substituted arylthio group, or a substituted or non-substituted heterocyclic group, and E is an oxy group, a thio group, or a seleno group.

Embodiment (5)

A display element comprising a display electrode an opposing electrode provided to oppose and separate from the display electrode with a predetermined space, and an electrolyte interposed between the display electrode and the opposing electrode, wherein a display layer containing the electrochromic compound as described in embodiment (1) is formed on a surface of the display electrode at an opposing electrode side.

Embodiment (6)

A display device comprising the display element as described in embodiment (5) and a part configured to drive the display element.

Embodiment (7)

An electrochromic compound represented by a general formula of

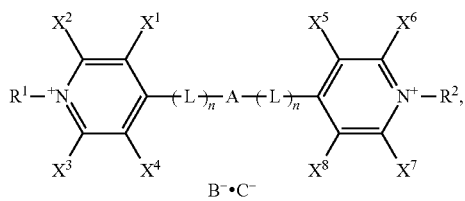

wherein
each of $X^1, X^2, X^3, X^4, X^5, X^6, X^7$, and $X^8$ is independently a hydrogen atom, a halogen group, a hydroxyl group, a nitro group, a cyano group, a carboxyl group, a substituted or non-substituted alkoxycarbonyl group, a substituted or non-substituted aryloxycarbonyl group, a substituted or non-substituted alkylcarbonyl group, a substituted or non-substituted arylcarbonyl group, an aminocarbonyl group, a substituted or non-substituted monoalkylaminocarbonyl group, a substituted or non-substituted dialkylaminocarbonyl group, a substituted or non-substituted monoarylaminocarbonyl group, a substituted or non-substituted diarylaminocarbonyl group, a sulfonate group, a substituted or non-substituted alkoxysulfonyl group, a substituted or non-substituted aryloxysulfonyl group, a substituted or non-substituted alkylsulfonyl group, a substituted or non-substituted arylsulfonyl group, an aminosulfonyl group, a substituted or non-substituted monoalkylaminosulfonyl group, a substituted or non-substituted dialkylaminosulfonyl group, a substituted or non-substituted monoarylaminosulfonyl group, a substituted or non-substituted diarylaminosulfonyl group, an amino group, a substituted or non-substituted monoalkylamino group, a substituted or non-substituted dialkylamino group, a substituted or non-substituted alkyl group, a substituted or non-substituted alkenyl group, a substituted or non-substituted alkynyl group, a substituted or non-substituted aryl group, a substituted or non-substituted alkoxy group, a substituted or non-substituted aryloxy group, a substituted or non-substituted alkylthio group, a substituted or non-substituted arylthio group, or a substituted or non-substituted heterocyclic group, each of $R^1$ and $R^2$ is independently a substituted or non-substituted alkyl group, a substituted or non-substituted alkenyl group, a substituted or non-substituted alkynyl group, or a substituted or non-substituted aryl group, A is a substituted or non-substituted 5-membered heterocyclic ring group containing one or more of N, O, S, or Se and containing C bonding to L, L is a substituted or non-substituted arylene group,
each of $B^-$ and $C^-$ is independently a monovalent anion,
n is 1, 2, or 3, and
$R^1$ and/or $R^2$ may be substituted with one or more kinds of functional groups selected from the group consisting of a sulfonate group, a phosphonate group, a phosphate group, and a carboxyl group.

Embodiment (8)

The electrochromic compound as described in embodiment (7), wherein each of $R^1$ and $R^2$ is independently a substituted or non-substituted alkyl group with a carbon number of 2 or more and 20 or less or a substituted or non-substituted aryl group.

Embodiment (9)

An electrochromic composition comprising the electrochromic compound as described in embodiment (7) being bonded or adsorbed to an electrically conductive or semi-conductive nano-structure.

Embodiment (10)

An electrochromic composition obtained by reacting with an electrically conductive or semi-conductive nano-structure a compound represented by a general formula of

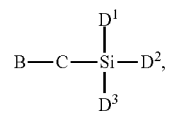

wherein
B is a halogen group,
C is an alkylene group,
$D^1$ is a halogen group or an alkoxy group,
each of $D^2$ and $D^3$ is independently a halogen group, an alkoxy group, or an alkyl group, and
subsequently reacting therewith a compound represented by a general formula of

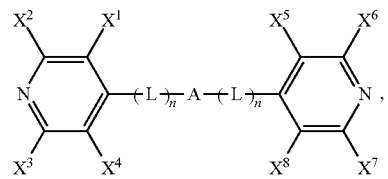

wherein
each of $X^1, X^2, X^3, X^4, X^5, X^6, X^7$, and $X^8$ is independently a hydrogen atom, a halogen group, a hydroxyl group, a nitro group, a cyano group, a carboxyl group, a substituted or non-substituted alkoxycarbonyl group, a substituted or non-substituted aryloxycarbonyl group, a substituted or non-substituted alkylcarbonyl group, a substituted or non-substituted arylcarbonyl group, an aminocarbonyl group, a substituted or non-substituted monoalkylaminocarbonyl group, a substituted or non-substituted dialkylaminocarbonyl group, a substituted or non-substituted monoarylaminocarbonyl group, a substituted or non-substituted diarylaminocarbonyl group, a sulfonate group, a substituted or non-substituted alkoxysulfonyl group, a substituted or non-substituted aryloxysulfonyl group, a substituted or non-substituted alkylsulfonyl group, a substituted or non-substituted arylsulfonyl group, an aminosulfonyl group, a substituted or non-substituted monoalkylaminosulfonyl group, a substituted or non-substituted dialkylaminosulfonyl group, a substituted or non-substituted monoarylaminosulfonyl group, a substituted or non-substituted diarylaminosulfonyl group, an amino group, a substituted or non-substituted monoalkylamino group, a substituted or non-substituted dialkylamino group, a substituted or non-substituted alkyl group, a substituted or non-substituted alkenyl group, a substituted or non-substituted alkynyl group, a substituted or non-substituted aryl group, a substituted or non-substituted alkoxy group, a substituted or non-substituted aryloxy group, a substituted or non-substituted alkylthio group, a substituted or non-substituted arylthio group, or a substituted or non-substituted heterocyclic group, A is a substituted or non-substituted 5-membered heterocyclic ring group containing one or more of N, O, S, or Se and containing C bonding to L, L is a substituted or non-substituted arylene group, and n is 1, 2, or 3.

Embodiment (11)

A display element comprising a display electrode, an opposing electrode provided to oppose and separate from the display electrode with a predetermined space, and an electrolyte interposed between the display electrode and the opposing electrode, wherein a display layer containing the electrochromic compound as described in embodiment (7) is formed on a surface of the display electrode at an opposing electrode side.

Embodiment (12)

A display device comprising the display element as described in embodiment (11) and a part configured to drive the display element.

Embodiment (13)

An electrochromic compound represented by the following general formula [3-1]

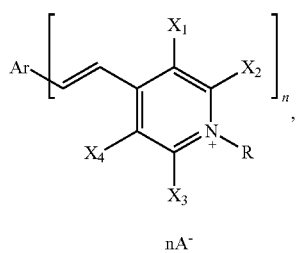

[3-1]

wherein each of $X_1$, $X_2$, $X_3$, and $X_4$ independently represents a hydrogen atom or a monovalent substitute, each of R independently represents a monovelent ubstitute, n represents an integer of 1 to 6, Ar represents a benzene ring with or without a substituent if n is 1 to 5 and simply represents a benzene ring if n is 6, and $A^-$ represents a monovalent anion.

Embodiment (14)

The electrochromic compound as described in embodiment (13), comprising a structure represented by the following general formula [3-2]

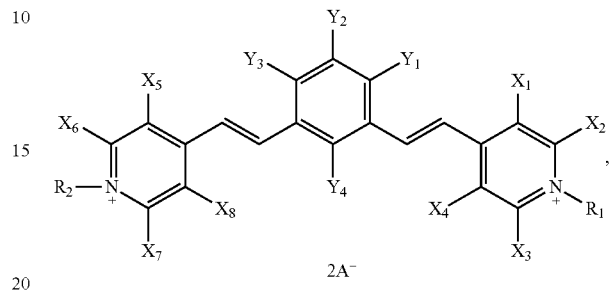

[3-2]

wherein each of $X_1$, $X_2$, $X_3$, $X_4$, $X_5$, $X_6$, $X_7$, $X_8$, $Y_1$, $Y_2$, $Y_3$, and $Y_4$ independently represents a hydrogen atom or a monovalent substituent, each of $R_1$ and $R_2$ independently represents a monovalent substitutent, and $A^-$ represents a monovalent anion.

Embodiment (15)

The electrochromic compound as described in embodiment (13), comprising a structure represented by the following general formula [3-3]

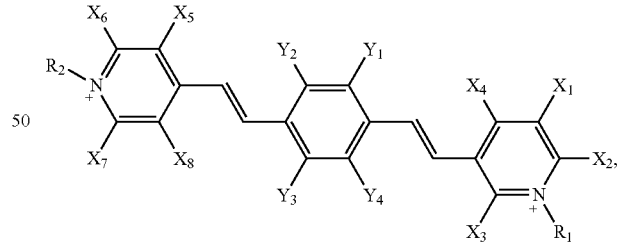

[3-3]

wherein each of $X_1$, $X_2$, $X_3$, $X_4$, $X_5$, $X_6$, $X_7$, $X_8$, $Y_1$, $Y_2$, $Y_3$, and $Y_4$ independently represents a hydrogen atom or a monovelent substituent, each of $R_1$ and $R_2$ independently represents a monovelent substitutent, and $A^-$ represents a monovalent anion.

Embodiment (16)

The electrochromic compound as described in embodiment (15), comprising a structure represented by the following general formula [3-4]

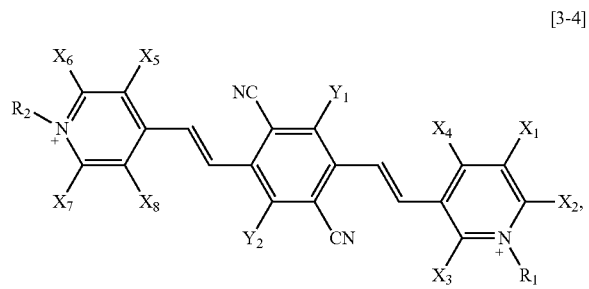

[3-4]

wherein
each of $X_1$, $X_2$, $X_3$, $X_4$, $X_5$, $X_6$, $X_7$, $X_8$, $Y_1$, and $Y_2$ independently represents a hydrogen atom or a monovelent substituent,
each of $R_1$ and $R_2$ independently represents a monovelent substitutent, and
$A^-$ represents a monovalent anion.

Embodiment (17)

The electrochromic compound as described in embodiment (13), wherein at least one of R or at least one of $R_1$ and $R_2$ is a functional group capable of bonding to a hydroxyl group directly or indirectly.

Embodiment (18)

An electrochromic composition comprising an electrically conductive or semi-conductive nano-structure and the electrochromic compound as described in embodiment (17) being bonded or adsorbed to the nano-structure.

Embodiment (19)

A display element comprising a display electrode, an opposing electrode provided to oppose and separate from the display electrode, and an electrolyte arranged between the display electrode and the opposing electrode, and having a display layer provided on a surface of the display electrode and opposing the opposing electrode, characterized in that the display layer contains at least the electrochromic compound as described in embodiment (13),

Embodiment (20)

An electrochromic compound characterized by being represented by the following structural formula [4-1]

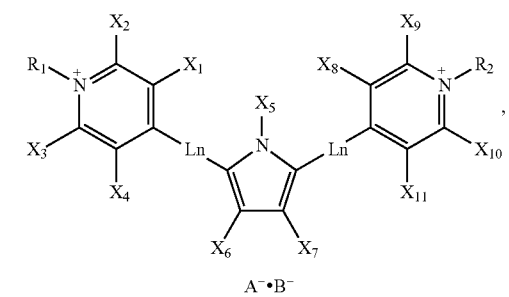

[4-1]

$A^- \cdot B^-$ wherein
each of $X_1$-$X_4$ and $X_6$-$X_{11}$ independently a hydrogen atom or a monovalent substituent,
$X_5$ represents an aryl group with or without a substituent or a heterocyclic group with or without a substituent,
each of $R_1$ and $R_2$ independently represents a monovelent substituent,
L represents an aromatic hydrocarbon group with or without a substituent,
n is an integer of 0 to 3, and
each of $A^-$ and $B^-$ independently represents a monovelent anion.

Embodiment (21)

The electrochromic compound as described in embodiment (20), wherein at least one of $R_1$ and $R_2$ is a functional group capable of bonding to a hydroxyl group directly or indirectly.

Embodiment (22)

An electrochromic composition comprising an electrically conductive or semi-conductive nano-structure and the electrochromic compound as described in embodiment (21) being bonded or adsorbed to the nano-structure.

Embodiment (23)

A display element comprising a display electrode, an opposing electrode provided to oppose and separate from the display electrode, and an electrolyte arranged between the display electrode and the opposing electrode, and having a display layer provided on a surface of the display electrode and opposing the opposing electrode, wherein the display layer contains at least the electrochromic compound as described in embodiment (20).

Although the illustrative embodiments and/or specific examples of the present invention have been described above with reference to the accompanying drawings, the present invention is not limited to any of the illustrative embodiments and specific examples and the illustrative embodiments and specific examples may be altered, modified, or combined without departing from the scope of the present invention.

The present application claims the benefit of its priority based on Japanese Patent Application No. 2009-238879 filed on Oct. 16, 2009 in Japan, Japanese Patent Application No.

2009-238880 filed on Oct. 16, 2009 in Japan, Japanese Patent Application No. 2009-239891 filed on Oct. 16, 2009 in Japan, Japanese Patent Application No. 2009-239892 filed on Oct. 16, 2009 in Japan, Japanese Patent Application No. 2010-172094 filed on Jul. 30, 2010 in Japan, Japanese Patent Application No. 2010-172866 filed on Jul. 30, 2010 in Japan, and Japanese Patent Application No. 2010-172867 filed on Jul. 30, 2010 in Japan, the entire contents of which are hereby incorporated by reference herein.

The invention claimed is:

1. An electrochromic compound represented by a general formula of

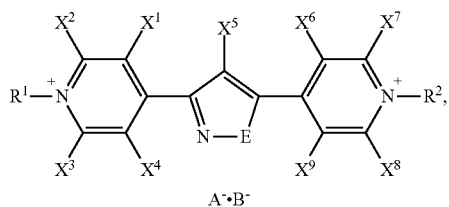

A⁻·B⁻ wherein
each of $X^1$, $X^2$, $X^3$, $X^4$, $X^5$, $X^6$, $X^7$, $X^8$, and $X^9$ is independently a hydrogen atom, a halogen group, a hydroxyl group, a nitro group, a cyano group, a carboxyl group, a substituted or non-substituted alkoxycarbonyl group, a substituted or non-substituted aryloxycarbonyl group, a substituted or non-substituted alkylcarbonyl group, a substituted or non-substituted arylcarbonyl group, an aminocarbonyl group, a substituted or non-substituted monoalkylaminocarbonyl group, a substituted or non-substituted dialkylaminocarbonyl group, a substituted or non-substituted monoarylaminocarbonyl group, a substituted or non-substituted diarylaminocarbonyl group, a sulfonate group, a substituted or non-substituted alkoxysulfonyl group, a substituted or non-substituted aryloxysulfonyl group, a substituted or non-substituted alkylsulfonyl group, a substituted or non-substituted arylsulfonyl group, an aminosulfonyl group, a substituted or non-substituted monoalkylaminosulfonyl group, a substituted or non-substituted dialkylaminosulfonyl group, a substituted or non-substituted monoarylaminosulfonyl group, a substituted or non-substituted diarylaminosulfonyl group, an amino group, a substituted or non-substituted monoalkylamino group, a substituted or non-substituted dialkylamino group, a substituted or non-substituted alkyl group, a substituted or non-substituted alkenyl group, a substituted or non-substituted alkynyl group, a substituted or non-substituted aryl group, a substituted or non-substituted alkoxy group, a substituted or non-substituted aryloxy group, a substituted or non-substituted alkylthio group, a substituted or non-substituted arylthio group, or a substituted or non-substituted heterocyclic group, each of $R^1$ and $R^2$ is independently a substituted or non-substituted alkyl group, a substituted or non-substituted alkenyl group, a substituted or non-substituted alkynyl group, or a substituted or non-substituted aryl group, E is an oxy group, a thio group, or a seleno group,
each of A⁻ and B⁻ is independently a monovalent anion, and
$R^1$ and/or $R^2$ may be substituted with one or more kinds of functional groups selected from the group consisting of a sulfonate group, a phosphonate group, a phosphate group, and a carboxyl group.

2. The electrochromic compound as claimed in claim 1, wherein each of $R^1$ and $R^2$ is independently a substituted or non-substituted alkyl group with a carbon number of 2 or more and 20 or less or a substituted or non-substituted aryl group.

3. An electrochromic composition, comprising the electrochromic compound as claimed in claim 1 being bonded or adsorbed to an electrically conductive or semi-conductive nano-structure.

4. An electrochromic composition obtained by
reacting with an electrically conductive or semi-conductive nano-structure a compound represented by a general formula of

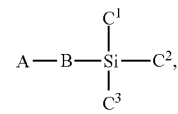

wherein
A is a halogen group,
B is an alkylene group,
$C^1$ is a halogen group or an alkoxy group, and
each of $C^2$ and $C^3$ is independently a halogen group, an alkoxy group, or an alkyl group, and
subsequently reacting therewith a compound represented by a general formula of

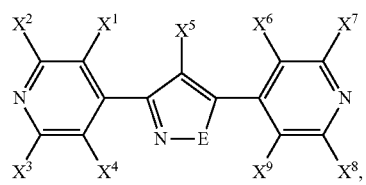

wherein
each of $X^1$, $X^2$, $X^3$, $X^4$, $X^5$, $X^6$, $X^7$, $X^8$, and $X^9$ is independently a hydrogen atom, a halogen group, a hydroxyl group, a nitro group, a cyano group, a carboxyl group, a substituted or non-substituted alkoxycarbonyl group, a substituted or non-substituted aryloxycarbonyl group, a substituted or non-substituted alkylcarbonyl group, a substituted or non-substituted arylcarbonyl group, an aminocarbonyl group, a substituted or non-substituted monoalkylaminocarbonyl group, a substituted or non-substituted dialkylaminocarbonyl group, a substituted or non-substituted monoarylaminocarbonyl group, a substituted or non-substituted diarylaminocarbonyl group, a sulfonate group, a substituted or non-substituted alkoxysulfonyl group, a substituted or non-substituted aryloxysulfonyl group, a substituted or non-substituted alkylsulfonyl group, a substituted or non-substituted arylsulfonyl group, an aminosulfonyl group, a substituted or non-substituted monoalkylaminosulfonyl group, a substituted or non-substituted dialkylaminosulfonyl group, a substituted or non-substituted monoarylaminosulfonyl group, a substituted or non-substituted diarylaminosulfonyl group, an amino group, a substituted or non-substituted monoalkylamino group, a substituted or non-substituted dialkylamino group, a substituted or non-substituted alkyl group, a substituted or non-substituted alkenyl group, a substituted or non-substituted alkynyl group, a substituted or non-substituted aryl group, a substituted or non-substituted alkoxy group, a substituted or non-substituted aryloxy group, a substituted or non-substituted alkylthio group, a substituted or non-substituted arylthio group, or a substituted or non-substituted heterocyclic group, and E is an oxy group, a thio group, or a seleno group.

5. A display element comprising a display electrode, an opposing electrode provided to oppose and separate from the display electrode with a predetermined space, and an electrolyte interposed between the display electrode and the opposing electrode, wherein a display layer containing the electrochromic compound as claimed in claim 1 is formed on a surface of the display electrode at an opposing electrode side.

6. A display device comprising the display element as claimed in claim 5 and a part configured to drive the display element.

* * * * *